(12) United States Patent
Freeman et al.

(10) Patent No.: US 10,426,963 B2
(45) Date of Patent: *Oct. 1, 2019

(54) ESTIMATING SHOCK SUCCESS BY MONITORING CHANGES IN SPECTRAL DATA

(71) Applicant: ZOLL Medical Corporation, Chelmsford, MA (US)

(72) Inventors: Gary A. Freeman, Waltham, MA (US); Weilun Quan, Dracut, MA (US); Ulrich Herken, Medford, MA (US); Christopher Luke Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 194 days.

This patent is subject to a terminal disclaimer.

(21) Appl. No.: 15/281,539

(22) Filed: Sep. 30, 2016

(65) Prior Publication Data

US 2017/0120063 A1 May 4, 2017

Related U.S. Application Data

(60) Provisional application No. 62/249,123, filed on Oct. 30, 2015.

(51) Int. Cl.
*A61N 1/39* (2006.01)
*A61B 5/0402* (2006.01)
(Continued)

(52) U.S. Cl.
CPC .......... *A61N 1/3925* (2013.01); *A61B 5/0402* (2013.01); *A61B 5/04012* (2013.01); (Continued)

(58) Field of Classification Search
CPC .. A61N 1/3925; A61B 5/04012; A61B 5/0402
See application file for complete search history.

(56) References Cited

U.S. PATENT DOCUMENTS 5,091,341 A 3/1992 Retell
9,186,521 B2 * 11/2015 Quan ................... A61N 1/3987
(Continued)

OTHER PUBLICATIONS

International Search Report & Written Opinion PCT/US2015/35174, dated Sep. 17, 2015, 13 pages.
(Continued)

*Primary Examiner* — Catherine M Voorhees
*Assistant Examiner* — Roland Dinga
(74) *Attorney, Agent, or Firm* — Fish & Richardson P.C.

(57) ABSTRACT

This document presents a system for managing treatment for an emergency cardiac event. The system includes memory, one or more electronic ports for receiving ECG signals, and a treatment module executable on one or more processing devices. The module is configured to perform a number of transformation on portions of an ECG signal into frequency domain data, obtain one or more previous values derived from one or more time segments of the ECG, and determine, based on the frequency domain data a first value and a second value, determine a probability of therapeutic success. The module is further configured to cause one or more output devices to present an indication of the probability of therapeutic success.

21 Claims, 28 Drawing Sheets

(51) Int. Cl.
*A61B 5/04* (2006.01)
*A61B 5/00* (2006.01)

(52) U.S. Cl.
CPC ........ *A61N 1/39044* (2017.08); *A61B 5/4848* (2013.01); *A61B 5/7275* (2013.01); *A61N 1/3993* (2013.01)

(56) References Cited

U.S. PATENT DOCUMENTS

| | | |
|---|---|---|
| 9,592,139 B2 | 3/2017 | Davidson et al. |
| 9,592,402 B2 | 3/2017 | Quan et al. |
| 10,086,210 B2 * | 10/2018 | Quan ................. H01L 23/53238 |
| 2011/0295127 A1 | 12/2011 | Sandler et al. |
| 2012/0226178 A1 | 9/2012 | Freeman et al. |
| 2013/0138168 A1 | 5/2013 | Quan et al. |
| 2013/0190634 A1 | 7/2013 | Phillips |
| 2014/0277225 A1 * | 9/2014 | Quan ................... A61N 1/3987 607/6 |

OTHER PUBLICATIONS

Office Action in U.S. Appl. No. 15/281,539, dated Jun. 29, 2018, 12 pages.

\* cited by examiner

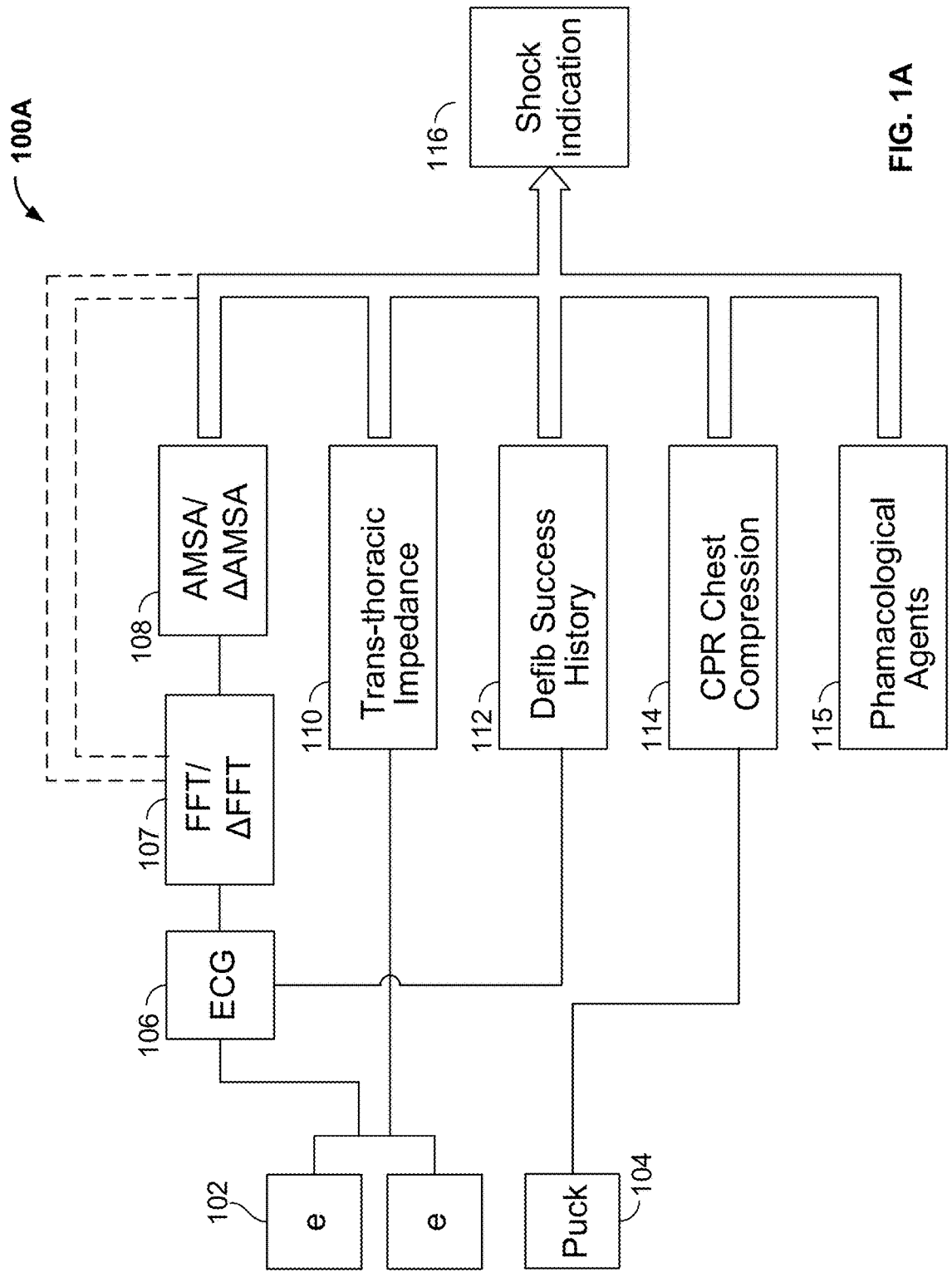

|  | 1st vs 2nd DF | 2nd vs 3rd DF | 3rd vs 4th DF | 4th vs 5th DF |
|---|---|---|---|---|
| AMSA changes between DFs | 12.24+0.62 vs. 9.94+0.48* | 8.60+0.34 vs. 9.41+0.58# | 9.47+0.91 vs. 8.58+0.62# | 8.35+0.73 vs. 9.04+0.90# |

| Selected AMSA thresholds | Events of correct prediction of 'non successful' DF | % of correct prediction overall 'non successful' DF |
|---|---|---|
| First DF (n=609) | | |
| 5 | 101 (N=102) | 99 |
| 5.5 | 124 (N=126) | 98.4 |
| 6 | 147 (N=153) | 96.1 |
| 6.5 | 175 (N=184) | 95.1 |
| 7 | 198 (N=213) | 93 |
| 7.5 | 213 (N=229) | 93 |
| Subsequent DFs (n=662) | | |
| 5 | 165 (N=168) | 98.2 |
| 5.5 | 205 (N=210) | 97.6 |
| 6 | 245 (N=254) | 96.5 |
| 6.5 | 272 (N=283) | 96.1 |
| 7 | 301 (N=317) | 95 |
| 7.5 | 328 (N=346) | 95 |

DF, defibrillation; *p<0.0001, #p>0.1

FIG. 1D

| 0 Shocks | 1 Shock | 2 Shocks | 3 Shocks | Success? |
|---|---|---|---|---|
| 100 | 90 | 80 | 70 | 90% |
| 90 | 80 | 70 | 60 | 80% |
| 80 | 70 | 60 | 50 | 70% |
| 70 | 60 | 50 | 40 | 60% |
| 60 | 50 | 40 | 30 | 50% |

| AMSA mV-Hz | Sensitivity % | Specificity % | PPV % | NPV % | Accuracy % |
|---|---|---|---|---|---|
| 1 | 100 | 1 | 27 | 100 | 28 |
| 2 | 100 | 5 | 28 | 100 | 31 |
| 3 | 100 | 11 | 29 | 100 | 35 |
| 4 | 99 | 18 | 31 | 99 | 40 |
| 5 | 99 | 27 | 34 | 99 | 47 |
| 6 | 99 | 40 | 38 | 99 | 56 |
| 7 | 96 | 49 | 41 | 97 | 62 |
| 8 | 87 | 59 | 44 | 93 | 67 |
| 9 | 83 | 65 | 47 | 91 | 70 |
| 10 | 73 | 72 | 49 | 88 | 72 |
| 11 | 67 | 76 | 51 | 86 | 74 |
| 12 | 60 | 80 | 53 | 84 | 75 |
| 13 | 53 | 82 | 52 | 83 | 74 |
| 14 | 48 | 84 | 53 | 81 | 75 |
| 15 | 42 | 87 | 54 | 80 | 75 |
| 16 | 37 | 91 | 59 | 79 | 76 |
| 17 | 31 | 92 | 60 | 78 | 76 |
| 18 | 23 | 93 | 54 | 77 | 74 |
| 19 | 21 | 94 | 55 | 76 | 74 |
| 20 | 21 | 95 | 58 | 76 | 75 |
| 25 | 10 | 97 | 53 | 74 | 73 |
| 30 | 3 | 99 | 50 | 73 | 73 |
| 40 | 2 | 100 | 78 | 74 | 74 |
| 50 | 1 | 100 | 100 | 74 | 74 |

|  | Refractory VF (n=543) | Recurrent VF (n=139) |
|---|---|---|
| Mean AMSA, mV-Hz | 7.6 ± 0.2 | 16.2 ± 0.9* |
| AMSA prior to successful DFs, mV-Hz | 12.7 ± 1 | 16.8 ± 1 |
| AMSA prior to failing DFs, mV-Hz | 7 ± 0.2 # | 13.8 ± 1.8 |
| Successful DFs, % (n) | 9.2 (50/543) | 79.1 (110/139) |

DFs, defibrillation attempts; VF, ventricular fibrillation; Mean ± SEM;
* $p < 0.0001$ vs. refractory VF; # $p < 0.0001$ vs. successful DFs

| AMSA mV-Hz | Sensitivity % | Specificity % | PPV % | NPV % | Accuracy % |
|---|---|---|---|---|---|
| 1 | 98 | 0 | 9 | 50 | 9 |
| 2 | 96 | 1 | 9 | 75 | 10 |
| 3 | 96 | 3 | 9 | 89 | 12 |
| 4 | 94 | 11 | 10 | 95 | 19 |
| 5 | 94 | 32 | 12 | 98 | 38 |
| 6 | 90 | 49 | 15 | 98 | 53 |
| 7 | 86 | 63 | 19 | 98 | 65 |
| 8 | 82 | 72 | 23 | 98 | 73 |
| 9 | 68 | 80 | 25 | 96 | 79 |
| 10 | 58 | 86 | 30 | 95 | 84 |
| 11 | 50 | 90 | 34 | 95 | 87 |
| 12 | 42 | 92 | 34 | 94 | 87 |
| 13 | 34 | 94 | 36 | 93 | 88 |
| 14 | 32 | 96 | 42 | 93 | 90 |
| 15 | 30 | 96 | 45 | 93 | 90 |
| 16 | 28 | 97 | 49 | 93 | 91 |
| 17 | 26 | 97 | 50 | 93 | 91 |
| 18 | 22 | 98 | 50 | 93 | 91 |
| 19 | 16 | 98 | 50 | 92 | 91 |
| 20 | 10 | 98 | 39 | 92 | 90 |
| 25 | 4 | 100 | 50 | 91 | 91 |
| 30 | 2 | 100 | 33 | 91 | 91 |
| 40 | 0 | 100 | 100 | 91 | 91 |

|  | Grp 1 | Grp 2 | p-value |
|---|---|---|---|
| AMSA | | | |
|    Start of ECC | 12.7±1.3 | 7.9±1.3 | 0.001 |
|    End of ECC | 11.6±1.8 | 11.6±1.9 | 0.9 |
|    Prior to $1^{st}$ Shock | 8.6±1.3 | 12.2±2.2 | 0.04 |
| LADrf prior to $1^{st}$ shock | 0.1±0.08 | 0.3±0.1 | 0.07 |
| Failed Shocks Before $1^{st}$ Shock Success (N) | 3±0.8 | 0.74±0.9 | 0.01 |
| Time to $1^{st}$ Shock Success (sec) | 837±45 | 721±77 | 0.05 |

Mean ± SD. LADrf, Blood flow in LAD relative to baseline LAD blood flow.

FIG. 1L

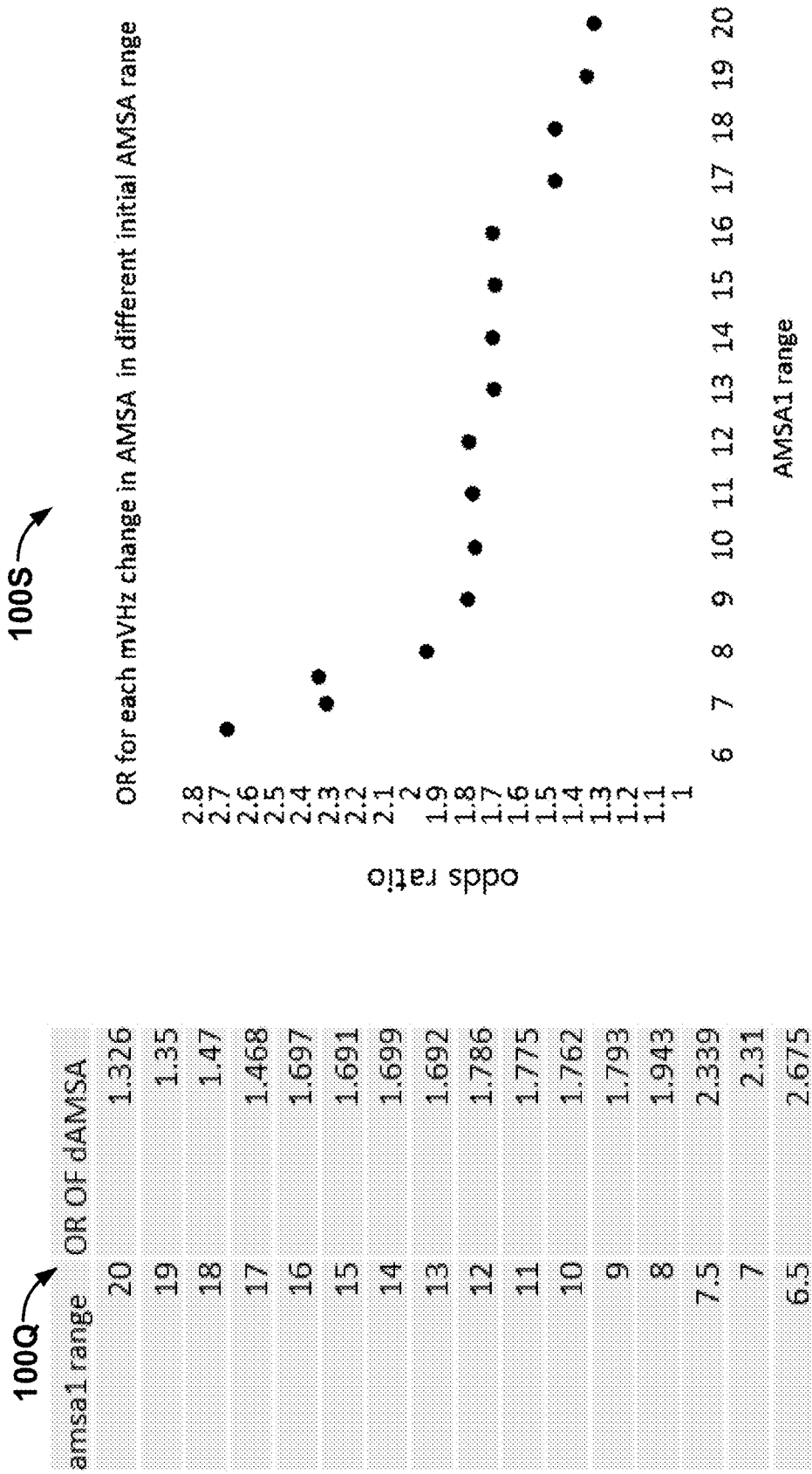

ESTIMATING SHOCK SUCCESS BY MONITORING CHANGES IN SPECTRAL DATA

CROSS-REFERENCE TO RELATED APPLICATION

This application claims benefit of priority to U.S. Provisional Application Ser. No. 62/249,123, filed on Oct. 30, 2015, the entire contents of which is hereby incorporated by reference.

TECHNICAL FIELD

This document relates to cardiac resuscitation systems and techniques.

BACKGROUND

Heart attacks are a common cause of death. A heart attack occurs when a portion of the heart tissue loses circulation and, as a result, becomes damaged (e.g., because of blockage in the heart vasculature). Heart attacks and other abnormalities can lead to ventricular fibrillation (VF), which is an abnormal heart rhythm (arrhythmia) that causes the heart to lose pumping capacity. If such a problem is not corrected quickly—typically within minutes—the rest of the body loses oxygen and the person dies. Therefore, prompt care of a person undergoing ventricular fibrillation can be key to a positive outcome for such a person.

One common way to treat ventricular fibrillation is through the use of an electrical defibrillator that delivers a relatively high voltage shock to the heart in order to restore a healthy and regular, rhythm associated with strong myocardial contractility. People who have had previous problems with ventricular fibrillation can be implanted with an automatic defibrillator that constantly monitors the condition of their heart and applies a shock when necessary. Other such people can be provided with a wearable defibrillator in the form of a vest such as the LIFEVEST product from ZOLL Medical Corporation. Other people can be treated using an external defibrillator, such as in a hospital or via an automatic external defibrillator (AED) of the kind that is frequently seen in airports, public gymnasiums, and other public spaces. Defibrillation can be delivered in coordination with cardiopulmonary resuscitation, which centers on the provision of repeated compressions to a victim's chest. For example, a rescuer can press downward repeatedly with the palms of the hands, or via a mechanical compression device such as the AUTOPULSE non-invasive cardiac support pump from ZOLL Medical Corporation.

People undergoing ventricular fibrillation can be more receptive to a defibrillating shock in some instances compared to others. For example, research has determined that an indication of whether a shock that is delivered would likely result in successful defibrillation can be obtained using a computation of amplitude spectrum area (AMSA), or other computational methods that use either time-based or spectrum-based analytic methods to calculate, from an electrocardiogram (ECG), a prediction of defibrillation shock success.

SUMMARY

This document describes systems and techniques that can be used to help determine when an electric shock delivered to a person suffering from VF can likely be successful, i.e., restore healthy cardiac rhythm. Such systems and techniques can also be used to estimate how long a person has been suffering from cardiac arrest or fibrillation, and use the time estimate to select the appropriate treatment (e.g., defibrillating shock, CPR). Systems and methods described herein provide for a spectral analysis that can result in a recommendation for a patient to be treated with an electric shock earlier than would otherwise be the case. For example, values output from a spectral analysis (e.g., AMSA, frequency transform) can be used in determining the appropriate treatment therapy for a patient at any given time, however, trends in values output from the spectral analysis can also be used as an additional factor in making the treatment determination. By using this additional information (e.g., considering changes in the spectral analysis in addition to absolute values output from the analysis) in calculating the probability of shock success, suitable therapeutic intervention(s) (e.g., electric shock in place of CPR) can be administered sooner than later. Techniques for making such predictions more accurately are also described herein.

Such determinations can be used to guide a person (e.g., a physician, EMT, or lay rescuer) who is performing rescue operations on the person suffering of VF (also referred to here as a patient or victim). The guidance can be provided by a portable defibrillator providing an audio-video indication, such as on a graphical display of the defibrillator or another device. The guidance can include a recommendation that a shock should or should not be provided, or that chest compressions of a particular type should be given instead of a shock. Also, a device can display an estimated time since the fibrillations began so as to provide further information to a rescuer. In implementations described below, for example, such systems and techniques can take into account the success or lack of success in prior attempts to defibrillate the person (e.g., where there has been recurrent or refractory VF—where recurrent VF results after a successful prior defibrillating shock and refractory VF results after an unsuccessful prior defibrillating shock), among other factors, such as a current AMSA value for the person and trans-thoracic impedance level of the person.

Such systems can also take into account a current AMSA value, an AMSA value over a different period of time, a trend in AMSA value over time, a change of AMSA value, a change rate of AMSA value and/or a myocardial viability indicator for recommending chest compressions or deliverance of a defibrillation shock. AMSA is a value calculated by taking a Fast Fourier Transform (FFT) of the VF waveform. While FFTs are generally premised on an assumption of an infinitely long time series, relatively short time series (e.g., less than 4 seconds and more preferably close to 1 second) can be better for predicting a likelihood of defibrillation. Short windows are generally improper for the operation of an FFT. As described below, a tapered window, such as a Tukey window, can be used to lessen edge effects from the windowing of ECG data that is collected for performing the AMSA calculation, which can permit the relative benefits of using a smaller window while lessening the dis-benefits of using the smaller window.

As one example of using AMSA values to make a determination of the likelihood that a currently-delivered shock with result in successful defibrillation, a threshold AMSA value can be set, at which level the shocking ability of a defibrillator is made available to a rescuer, or at which a likelihood of success that is displayed to the rescuer can change (e.g., AMSA values between X and Y can show a likelihood of m percent, while AMSA values between Y and Z can show a likelihood value of n percent) based on whether prior successful defibrillating shocks that have been given to a patient have been successful. For example, the relevant AMSA threshold for generating a particular output or action of a defibrillator (such as the display to the user just mentioned) can be adjusted based on determinations about the success of prior shocks and on the trans-thoracic impedance.

Thus, for example, an AMSA value or values can be computed from incoming ECG signals from the person, and decisions can be made by comparing the computed AMSA value to stored thresholds, where the thresholds can change based on the other factors, or the AMSA value can be adjusted using the other factors and then be compared to thresholds that do not change. Generally, there is no practical difference between changing the value and making static the thresholds against which it is compared versus changing the thresholds and leaving the value set.

Such adjustments, when based on determinations about the success or lack of success of prior defibrillation efforts, can be made in a variety of ways. For example, AMSA threshold values (which are reduced for recurrent VF) associated with future successful defibrillation have been determined to decrease substantially when there has been a prior successful defibrillation during an emergency with a particular patient. (Unless indicated otherwise, all values that are collected, computed, and compared here are for a single adverse cardiac event for a patient.)

Such correlations can be determined by analysis of historical defibrillation activity (e.g., collected by portable defibrillators deployed in the field for actual cardiac events), and can be used to produce a mapping between observed past likelihood of success for various AMSA values and levels of prior successful defibrillations. Such data can be used, for example, to generate a look-up table or similar structure that can be loaded on other deployed (e.g., via network and/or wireless data updates) or to-be-deployed defibrillators, which can be consulted in the future during other cardiac events. For example, the number of prior successful defibrillations for an event can be along one axis of a table, and an AMSA score can be along another, and those other defibrillators can employ both values for a victim, with the table producing an indication of a likelihood of a to-be-applied shock being successful. The table or other data structure can also have additional dimensions, such as a dimension that identifies trans-thoracic impedance, and dimensions that identify other variables whose values that have been determined to be relevant to whether an applied shock can likely be successful.

As noted, a tapering function can be applied to the ECG data, so as to improve the accuracy of the FFT applied to the data, by preventing the data from jumping immediately from a zero value up the measured values, and then back down immediately to a zero value at the end of a measured window. Various parameters for the tapering function can also be applied, such as coefficients to define the slops of the starting and ending edges of the function. The particular type of tapering function used and the coefficients applied to it can be determined by analysis of ECG data and shock outcomes from prior rescue efforts that have been sensed and stored by on-site monitors (e.g., as part of portable defibrillators), and analyzed after-the-fact as a group to identify correlations between particular AMSA values, window sizes, window shapes, and defibrillation outcomes.

In some implementations, multiple different tapering functions can be applied to the same data essentially simultaneously, and the resulting AMSA value from one of the functions can be selected, or an AMSA value can be generated that is a composite from multiple different tapering functions. The window function that is used, the length of the window, and the coefficients for the window can also be adjusted dynamically, so that one or more of them change during a particular incident, or deployment, with a particular patient. For example, it can be determined from analysis of prior data that a particular window shape, size, and/or coefficients are better earlier in an episode of VF than later, so that a defibrillator can be programmed to change such parameters over the course of an event. Such changes can be tied to an initial determination about how long the patient has been in VF, which can be a function of user input (e.g., when the emergency call was made) and parameters measured by the defibrillator. Also, changes to the window type, size, and coefficients can be made from readings dynamically made from the patient under treatment. For example, AMSA values in a particular range can be measured better by a particular window type, size, or range of coefficients, so that an AMSA measurement made at time n that shows such a value, can be measured using the other parameters known to work best with that AMSA value at time n+1. Other techniques for dynamically adjusting the window type, window size, and/or coefficients can also be employed. The shape of the window can be asymmetric. For instance, the edge of the window that is "older" in time can have a window shape that results in a greater level of attenuation that the "newer" portion of the windowed data.

Upon a defibrillator making a determination of a likelihood of future success for defibrillating a patient, the defibrillator can provide an indication to a rescuer about such a determination. For example, the defibrillator can only allow a shock to be performed when the indication is sufficiently positive (e.g., over a set percentage of likelihood of success)—and can only provide a "ready for shock" light or other indication in such a situation. Also, a defibrillator can provide a display—such as a graphic that shows whether defibrillation can likely succeed (e.g., above a predetermined threshold level of likelihood of success) or provide a number (e.g., a percentage of likelihood of success) or other indication (e.g., a grade of A, B, C, D, or F) so that the rescuer can determine whether to apply a shock. In some situations, the AMSA value can serve merely to provide a recommendation to the user, with the user able to apply a shock at any time; in other situations (e.g., especially for AEDs to be used by lay rescuers), the AMSA value can be used to disable or enable the ability to deliver a shock.

The device (e.g., defibrillator) can also change the indication it presents in different situations, e.g., a dual-mode defibrillator could simply indicate whether defibrillation is advised (and can refuse to permit delivery of a shock when it is not advised) when the defibrillator is in AED mode, and can provide more nuanced information when the defibrillator is in manual mode, and thus is presumably being operated by someone who can better interpret such nuanced information and act properly on it.

With respect to indications of where a victim is in the process of a VF episode—e.g., how many minutes since the victim's episode has started—an average AMSA value can be determined over a time period so as to identify more generalized changes in the victim's AMSA values, rather than AMSA at a particular point in time or small slice of time. For example, AMSA values can be computed for particular points in time or particular windows in time and those values can be saved (e.g., in memory of a patient monitor or defibrillator). After multiple such measurements and computations have been made, an average can be computed across multiple such values. Because AMSA generally decreases (on average) over time in an episode, if the average for a particular number of readings (e.g., a moving average) decreases below a particular value or decreases below the value over a minimum time period (so as to indicate the general AMSA condition of the victim rather than just a transient reading), the device can provide additional feedback to a rescuer.

These general phases of cardiac arrest or VF can be identified, in one representation, as three separate phases (though there can be some overlap at the edges of the phases): electrical, circulatory, and metabolic. The electrical phase is the first several minutes of an event, and marks a period during which electric shock can be particularly effective in defibrillating the victim's heart and returning the victim to a relative satisfactory condition. The circulatory phase appears to mark a decrease in effectiveness for electric shock in defibrillating the victim, and particularly in the absence of chest compressions performed on the victim. As a result, a device such as a portable defibrillator can be programmed to stop advising shocks during such a phase (or can advise a shock only when other determinations indicate that a shock would be particularly likely to be effective) and can instead advise forceful CPR chest compressions. Such forceful compressions can maximize blood flow through the heart tissue and other parts of the body so as to extend the time that the victim can survive without lasting or substantial damage.

In the metabolic phase, chest compressions can be relatively ineffective as compared to the circulatory phase. For example, where tissue has become ischemic, such as in circulatory phase, the tissue can react favorably to the circulation of blood containing some oxygen, but where tissue has become severely ischemic, such as in metabolic phase, the introduction of too much oxygen can be harmful to the tissue. As a result, more gentle compressions for the first period, such as 32 seconds, can be advised in the metabolic phase before the rescuer (or a mechanical chest compressor controlled to provide appropriate levels of compression following the points addressed here) uses a full force.

Other treatments that can be useful in the metabolic phase include extracorporeal circulation and cooling, either alone, in combination with each other, or in combination with other pharmacological treatments. In any event, observation of elapsed time since an event has begun and/or observation of the phase in which a victim is in, can be used to control a device or instruct a rescuer to switch from a first mode of providing care to a second mode of providing care in which the parameters of the provided care differ (e.g., speed or depth of chest compressions can change, temperature-based therapy can be provided or stopped, or pharmaceuticals can be administered).

In some implementations, such systems and techniques can provide one or more advantages. For example, determinations of whether a shock should be provided or what advice to provide a rescuer based on the phase a victim is in can be made from values that are already being measured for a patient (e.g., trans-thoracic impedance can already be used by a defibrillator to affect the shape of the voltage of the waveform that is provided to the patient). For example, determinations about shocks can be improved compared to simply measuring AMSA, and can thus result in better performance for a system and better outcomes for a patient. In particular, a defibrillator can cause a rescuer to wait to provide a defibrillating shock until a time at which the shock is more likely to be effective. As a result, the patient can avoid receiving an ineffective shock, and then having to wait another cycle for another shock (which can end up being equally ineffective). And a system can guide the rescuer in providing a shock, versus providing deep chest compressions, versus providing progressive chest compressions (or can cause a device to provide such actions automatically), throughout the course of a cardiac event. Such a process may, therefore, result in the patient returning to normal cardiac function more quickly and with less stress on his or her cardiac system, which can generally lead to better patient outcomes.

The use of particular type, duration, and coefficients for making AMSA readings can result in more accurate instructions being given to a human or mechanical rescuer, or in enabling or disabling functionality of a medical device. In particular, the feedback provided can result in determinations about whether to shock or not shock, or to provide chest compressions, can be more closely aligned with a likelihood of a positive outcome (e.g., defibrillation) for a particular patient, and can be customized to the present situation of the patient (e.g., as indicated by AMSA readings for the patient).

In one implementation, a system for managing treatment for an emergency cardiac event, includes memory and one or more electronic ports for receiving signals from sensors for obtaining indications of an electrocardiogram (ECG) for a patient. The system also includes a patient treatment module executable on one or more processing devices, wherein the patient treatment module is configured to generate transform values for a time segment of ECG. The transform values represent magnitudes of two or more frequency components of the ECG. The patient treatment module is also configured to obtain one or more previous values derived from one or more earlier time segments of the ECG, determine, based on the generated transform values, and the one or more previous values, at least one of: a) a future therapeutic action for treating the emergency cardiac event, or b) a phase of the cardiac event. The patient treatment module is further configured to cause one or more output devices to present an indication of at least one of the therapeutic action or the phase of the cardiac event.

In another aspect, a system for treating a patient in cardiac arrest includes memory, and one or more electronic ports for receiving signals from sensors for obtaining indications of an electrocardiogram (ECG) for the patient. The system also includes a patient treatment module executable on one or more processing devices. The patient treatment module is configured to generate transform values that represent magnitudes of two or more frequency components of the ECG, generate a time series from a plurality of the transform values, and determine, based on the time series, a future therapeutic action for treating the cardiac arrest.

In another aspect, a system for managing treatment for an emergency cardiac event includes memory, and one or more electronic ports for receiving signals from sensors for obtaining indications of an electrocardiogram (ECG) for a patient. The system also includes a patient treatment module executable on one or more processing devices. The patient treatment module is configured to generate transform values for a time segment of ECG, wherein the transform values represent magnitudes of two or more frequency components of the ECG. The patient treatment module is also configured to obtain one or more previous transform values derived from one or more earlier time segments of the ECG, determine, based on the generated transform values, and the one or more previous transform values, an indication of a likelihood of success from delivering a defibrillating shock, and cause one or more output devices to present the indication of a likelihood of success from delivering a defibrillating shock.

In another aspect, this document features one or more machine-readable storage devices having encoded thereon machine readable instructions for causing one or more processors to perform various operations. The operations include receiving, signals indicative of an electrocardiogram (ECG) of a patient, and generating transform values for a time segment of the ECG, wherein the transform values represent magnitudes of two or more frequency components of the ECG. The operations also include obtaining one or more previous values derived from one or more earlier time segments of the ECG, determining, based on the generated transform values, and the one or more previous values, a future therapeutic action for treating an emergency cardiac event in the patient, and causing one or more output devices to present an indication of at least one of the therapeutic action or the phase of the cardiac event.

In another aspect, this document features one or more machine-readable storage devices having encoded thereon machine readable instructions for causing one or more processors to perform various operations that include receiving signals indicative of an electrocardiogram (ECG) of a patient, and generating transform values. The transform values represent magnitudes of two or more frequency components of the ECG. The operations also include generating a time series from a plurality of the transform values, and determining, based on the time series, a future therapeutic action for treating a cardiac arrest of the patient.

In another aspect, this document features one or more machine-readable storage devices having encoded thereon machine readable instructions for causing one or more processors to perform various operations that include receiving, signals indicative of an electrocardiogram (ECG) of a patient, and generating transform values. The transform values represent magnitudes of two or more frequency components of the ECG. The operations also include obtaining one or more previous transform values derived from one or more earlier time segments of the ECG, determining based on the generated transform values, and the one or more previous transform values, an indication of a likelihood of success from delivering a defibrillating shock, and causing one or more output devices to present the indication of a likelihood of success from delivering a defibrillating shock.

Implementations of the above aspect can include one or more of the following features.

The patient treatment module can include an ECG analyzer for generating an amplitude spectrum area (AMSA) value using the transform values. The previous values can be derived from one or earlier time segments of the ECG are AMSA values. The transform values can be updated at a rate of 0.1-10 Hz. The length of the time segment can be in the range between about 1 and 4 seconds. The one or more processing devices can generate the transform values for the time segment of ECG using a tapered window. The tapered window can be one of: a Tukey window, a Hann window, a Blackman-Harris window, or a Flat Top window. The future therapeutic action can be determined based at least in part on comparing a value obtained from the generated transform values to a threshold. The transform can include at least one of: Fourier, fast Fourier, discrete Fourier, Hilbert, discrete Hilbert, wavelet, and discrete wavelet methods. The therapeutic action can include computing an average based on the one or more previous values. The average can be also based on a value obtained from the generated transform values.

The one or more previous values can be generated via processing of multiple earlier time segments of the ECG. The processing can be performed two or more times during the cardiac event. The one or more output devices can present an audible or visual feedback of at least one of the indication of the therapeutic action or the phase of the cardiac event. The therapeutic action can include delivering a defibrillating shock to the patient. The therapeutic action can include initiating or continuing cardiopulmonary resuscitation (CPR). The therapeutic action can include adjusting a cardiopulmonary resuscitation (CPR) technique. The phase can be one of: an electrical phase, a circulatory phase, or a metabolic phase. The one or more output devices can present a visual or audible feedback based on the generated transform values and the previous values. The feedback includes an indication of a likelihood of success from delivering a defibrillating shock. The future therapeutic action or the phase of the cardiac event can be generated based on one or more additional parameters. The one or more additional parameters can include at least one of: trans-thoracic impedance (TTI), levels of prior successful defibrillations, and a trend in AMSA values over time.

The transform values can include amplitude spectrum area (AMSA) values. The therapeutic action can be determined based on determining a trending of the transform values in the time series. The transform values can include normalized transform values. The transform can include a Fast Fourier Transform. The transform can include one or more of: Fourier, discrete Fourier, Hilbert, discrete Hilbert, wavelet, and discrete wavelet methods. The transform can be a transform that uses zero crossing analysis.

In one implementation, a system for managing care of a person receiving emergency cardiac assistance is disclosed. The system comprises one or more capacitors for delivering a defibrillating shock to a patient; one or more electronic ports for receiving signals from sensors for obtaining indications of an electrocardiogram (ECG) for the patient; and a patient treatment module executable on one or more computer processors to provide a determination of a likelihood of success from delivering a future defibrillating shock to the person with the one or more capacitors, using (a) information about a prior defibrillating shock, and (b) a value that is a function of current ECG signals from the patient. The system can also include an output mechanism arranged to indicate, to a user of the system, an indication regarding the likelihood of success from delivering a defibrillating shock to the person with the one or more capacitors. The output mechanism can include a visual display, and the system can be programmed to display to the user one of multiple possible indications that each indicate a degree of likelihood of success. Alternatively or in addition, the output mechanism can comprise an interlock that prevents a user from delivering a shock unless the determined likelihood of success exceeds a determined value.

In some aspects, the patient treatment module comprises an ECG analyzer for generating an amplitude spectrum area (AMSA) value, wherein the patient treatment module uses the information about the level of success from the prior defibrillating shock to adjust the AMSA value. Moreover, the patient treatment module can comprise an ECG analyzer for generating indications of heart rate for the patent, heart rate variability for the patent, ECG amplitude for the patent, and/or first or second derivatives of ECG amplitude for the patent. The indication of ECG amplitude can comprise, for example, an RMS measurement, measure peak-to-peak, peak-to-trough, or an average of peak-to-peak or peak-to-trough over a specified interval In other aspects, the patient treatment module is programmed to determine whether a prior defibrillation shock was at least partially successful, and based at least in part on the determination of whether the prior defibrillation was at least partially successful, modify a calculation of the likelihood of success from delivering the future defibrillating shock. Moreover, determining a likelihood of success from delivering a future defibrillating shock to the person can depend on a determination of whether one or more prior shocks delivered to the person were successful in defibrillating the person. In addition, determining a likelihood of success from delivering a future defibrillating shock can comprise performing a mathematical transform on the ECG data. The mathematical transform can be selected from a group consisting of Fourier, discrete Fourier, Hilbert, discrete Hilbert, wavelet, and discrete wavelet methods. In some implementations, the determination of the likelihood of success can include a zero-crossing based analysis, an example of which is described in Kedem, *Spectral Analysis and Discrimination by Zero-Crossings*, Proceedings of the IEEE, Vol. 74, No 11, November 1986. Zero-crossing counts in filtered time series can be referred to as higher order crossings. In addition, determining a likelihood of success from delivering a future defibrillating shock comprises performing a calculation by an operation selected from a group consisting of logistic regression, table look-up, neural network, and fuzzy logic.

In yet another example, the patient treatment module is programmed to determine the likelihood of success from delivering a future defibrillating shock using at least one patient-dependent physical parameter separate from a patient ECG reading. The patient treatment module can also be programmed to determine the likelihood of success from delivering a future defibrillating shock using at a measure of trans-thoracic impedance of the person.

In another implementations, a method for managing care of a person receiving emergency cardiac assistance is disclosed, and comprises monitoring, with an external defibrillator, electrocardiogram (ECG) data from a person receiving emergency cardiac assistance; determining whether a prior defibrillation shock occurred; determining a likelihood of future defibrillation shock success using at least the ECG data; based at least in part on the determination of whether the prior defibrillation occurred, modifying the calculation of the chance of defibrillation shock success; and affecting control of the external defibrillator based on the identification of whether a present defibrillation shock can likely be effective. Determining a likelihood of future defibrillation shock success can comprise determining a value that is a function of electrocardiogram amplitude at particular different frequencies or frequency ranges. Determining a likelihood of future defibrillation shock success can comprise determining an amplitude spectrum area (AMSA) value for the ECG data, and can also comprise adjusting the determined AMSA value using information about the prior defibrillation shock. In addition, the method can comprise determining whether the adjusted AMSA value exceeds a predetermined threshold value.

In some implementations, the method comprises providing to the rescuer a visual, audible, or tactile alert that a shockable situation exists for the person, if the adjusted AMSA value is determined to exceed the predetermined threshold value. The method can also include determining whether a prior defibrillation shock was at least partially successful, and based at least in part on the determination of whether the prior defibrillation was at least partially successful, modifying a calculation of the likelihood of success from delivering the future defibrillating shock. The determining of a likelihood of success from delivering a future defibrillating shock can comprise performing a mathematical transform on the ECG data, and the mathematical transform can be selected from a group consisting of Fourier, discrete Fourier, Hilbert, wavelet, and discrete wavelet methods. Also, determining a likelihood of success from delivering a future defibrillating shock can comprise performing a calculation by an operation selected from a group consisting of logistic regression, table look-up, neural network, and fuzzy logic. Moreover, the likelihood of success from delivering a future defibrillating shock can be determined using at least one patient-dependent physical parameter separate from a patient ECG reading.

In some implementations, the additional physiologic parameter is trans-thoracic impedance of the person receiving emergency cardiac care, and the indication of trans-thoracic impedance can be determined from signals sensed by a plurality of electrocardiogram leads that also provide the EGC data. The method can also include cyclically repeating the actions of monitoring, determining, identifying and providing the indication. The method also can comprise identifying compression depth of chest compressions performed on the person, using a device on the person's sternum and in communication with the external defibrillator, and providing feedback to a rescuer performing the chest compressions regarding rate of compression, depth of compression, or both.

In yet another implementation, there is disclosed a system for managing care of a person receiving emergency cardiac assistance that comprises one or more capacitors for delivering a defibrillating shock to a patient; one or more electronic ports for receiving signals from sensors for obtaining indications of an electrocardiogram (ECG) for the patient; and a patient treatment module executable on one or more computer processors to identify an phase in which a patient being monitored by the system is in relative to a time at which an adverse cardiac event for patient began. The phase in which the patient being monitored by the system is in can includes an elapsed time since the adverse cardiac event for the patient began, and a phase selected from an electrical, circulatory, and metabolic phase. The system can also comprise an output mechanism arranged to indicate, to a user of the system, an indication regarding the phase in which the patient is in. The output mechanism can comprise a visual display, and the system can be programmed to display to the user one indication of multiple possible indications, wherein the one indication indicates to the user the phase in which the patient is in.

In some implementations, the system is programmed to display instructions for the user to care for the patient, the instructions selected to correspond to the phase in which the patient is in. Also, the output mechanism can include an interlock that prevents a user from delivering a shock unless a determined likelihood of success of a shock reviving the patient exceeds a determined value. In other aspects, the patient treatment module comprises an ECG analyzer for generating an amplitude spectrum area (AMSA) value, an indication of heart rate for the patent, an indication of heart rate variability for the patent, or an indication of ECG amplitude for the patent.

In yet other aspects, the indication of ECG amplitude comprises an RMS measurement, measured peak-to-peak, peak-to-trough, or an average of peak-to-peak or peak-to-trough over a specified interval. Also, the patient treatment module can include an ECG analyzer for generating an indication of a first derivative of ECG amplitude for the patent, or an indication of a second derivative of ECG amplitude for the patent. Moreover, the patient treatment module can be programmed to determine whether a defibrillation shock, prior to a future defibrillation shock being consider for delivery, was at least partially successful, and based at least in part on the determination of whether the prior defibrillation shock was at least partially successful, modifying a calculation of a likelihood of success for delivering the future defibrillation shock.

In another implementation, a method for managing care of a person receiving emergency cardiac assistance is disclosed and comprises monitoring, with an external defibrillator, electrocardiogram (ECG) data from a person receiving emergency cardiac assistance; performing a mathematical transform of the ECG data from a time domain to a frequency domain using a tapered window in the time domain; determining a likelihood of future defibrillation shock success using at least the mathematical transformation; and affecting control of the external defibrillator based on the identification of whether a present defibrillation shock can likely be effective. The tapered window can comprise a Tukey window, and can be between about one second and about 2 seconds wide. The tapered window can be selected from a group consisting of Tukey, Hann, Blackman-Harris, and Flat Top, and the mathematical transform can comprise a Fast Fourier Transform.

In some implementations, determining a likelihood of future defibrillation shock success comprises determining a value that is a function of electrocardiogram amplitude at particular different frequencies or frequency ranges. It can also comprise determining an amplitude spectrum area (AMSA) value for the ECG data. Also, determining a likelihood of future defibrillation shock success can further comprise adjusting the determined AMSA value using information about a prior defibrillation shock. Moreover, the method can additionally include determining whether the adjusted AMSA value exceeds a predetermined threshold value. In some aspects, the method also includes providing to a rescuer a visual, audible, or tactile alert that a shockable situation exists for the person receiving emergency cardiac assistance, if the adjusted AMSA value is determined to exceed the predetermined threshold value.

In yet other aspects, the method comprises determining whether a prior defibrillation shock was at least partially successful, and based at least in part on the determination of whether the prior defibrillation was at least partially successful, modifying a calculation of the likelihood of success from delivering the future defibrillating shock. In some implementations, determining a likelihood of success from delivering a future defibrillating shock comprises performing a calculation by an operation selected from a group consisting of logistic regression, table look-up, neural network, and fuzzy logic. The likelihood of success can also be determined using at least one patient-dependent physical parameter separate from a patient ECG reading, and the additional patient-dependent parameter can comprise an indication of trans-thoracic impedance of the person receiving emergency cardiac care.

In additional aspects, the indication of trans-thoracic impedance is determined from signals sensed by a plurality of electrocardiogram leads that also provide the EGC data. The method can also comprise cyclically repeating the actions of monitoring, determining, identifying and affecting the control, and can also or alternatively include identifying compression depth of chest compressions performed on the person receiving emergency cardiac assistance, using a device on the person's sternum and in communication with the external defibrillator, and providing feedback to a rescuer performing the chest compressions, the feedback regarding rate of compression, depth of compression, or both. Also, the affecting control can include preventing a user from delivering a shock unless the determination of whether a shock can be effective exceeds a determined likelihood level, and/or electronically displaying, to a user, an indicator of the determined indication of whether a shock can be effective. In addition, displaying an indicator can include displaying a value, of multiple possible values in a range that indicates a likelihood of success. Moreover, the calculation of the likelihood of current shock success can be determined or modified using a determination of a value of trans-thoracic impedance of the person.

In some implementations, a system is provided that includes one or more electronic ports for receiving signals from sensors for obtaining a time domain electrocardiogram (ECG) of the patient, and a patient treatment module comprising an ECG analyzer and a non-transitory computer-readable storage medium encoded with a computer program comprising instructions that, when executed, cause one or more processors to perform a number of operations. The operations can include performing at least one transformation of at least a portion of the time domain ECG signal from the patient into frequency domain data, determining a first frequency-based value over a first evaluation period based on the at least one transformation, determining a second frequency-based value representing a trend over a second evaluation period based on the at least one transformation, determining a probability of therapeutic success based at least in part on the first frequency-based value and the second frequency-based value, and providing an indication of the probability of therapeutic success.

Other features and advantages will be apparent from the description and drawings, and from the claims.

DESCRIPTION OF DRAWINGS

FIG. 1A shows schematically the combination of various types of data in making a determination about likely effectiveness of a defibrillating shock.

FIG. 1D is a table showing examples relating AMSA to predicted likelihood of failure in defibrillating a victim who has or has not been previously defibrillated.

FIG. 1E is a schematic diagram of an example data structure for correlating AMSA and defibrillation success to predicted outcomes for shocking a victim.

FIG. 1F is an example table showing predictions of successful defibrillation for different AMSA threshold values in the instances of $1^{st}$ defibrillation attempts.

FIG. 1G is an example table showing AMSA prior defibrillation for refractory and recurrent VF.

FIG. 1H is an example table showing prediction of successful defibrillation for increasing AMSA threshold values in the instances of refractory VF.

FIG. 1L is a chart of AMSA values and statistics.

FIG. 1O is another example display including an AMSA representation.

FIG. 1Q is an example table showing prediction of successful defibrillation for each mVHz change in AMSA.

FIG. 1S is an example graphical representation showing prediction of successful defibrillation for each mVHz change in AMSA.

DETAILED DESCRIPTION

Figure 1B:
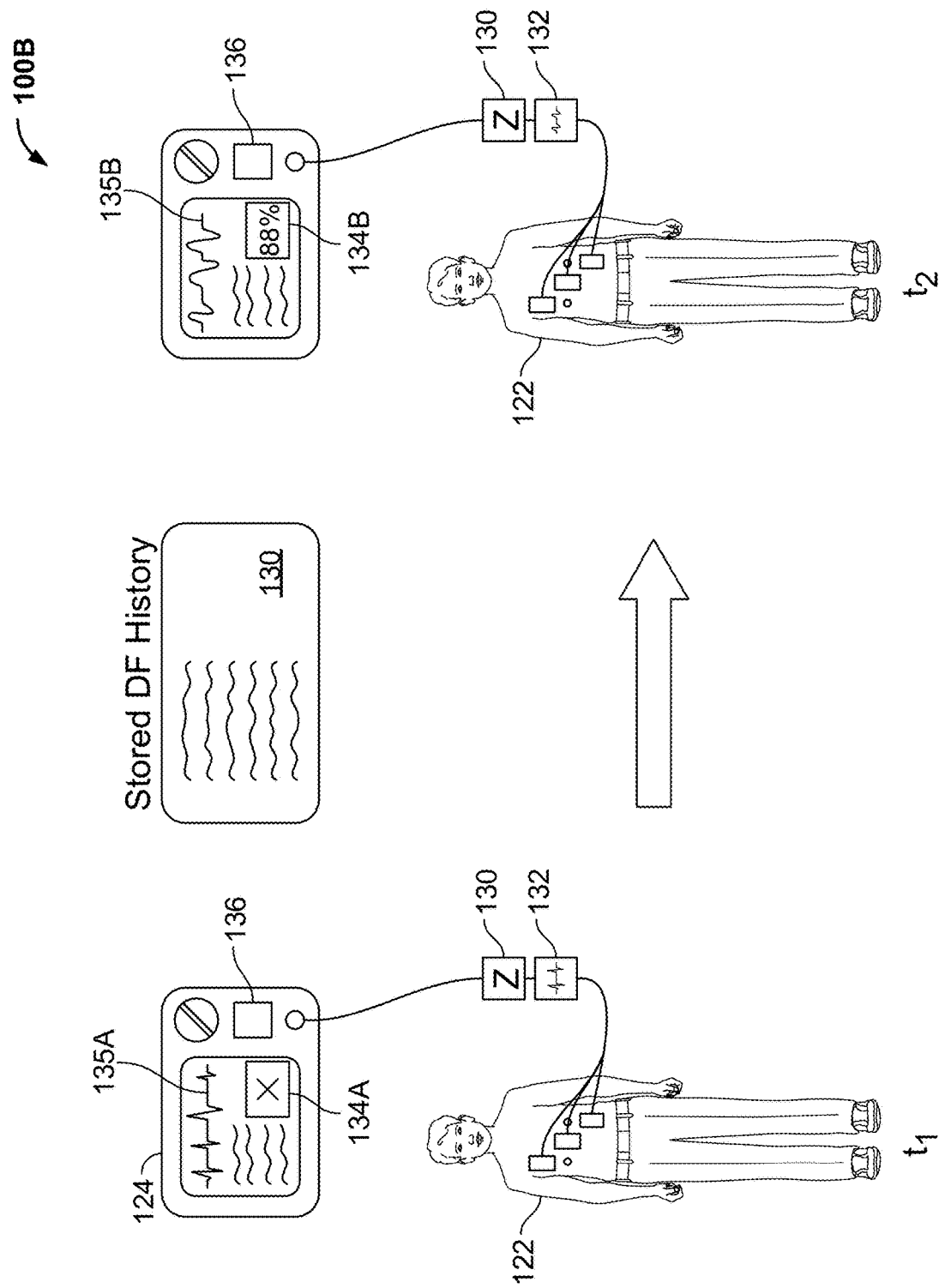
FIG. 1B shows a victim of a cardiac event being treated with an example portable defibrillator.

The present disclosure generally relates to the use of changes or trends in spectral frequency (e.g., AMSA, FFT) in evaluating the likelihood that an electrical shock will lead to a successful therapeutic result (e.g., defibrillation). For example, when the AMSA or other frequency-based data is greater than a certain threshold, the percentage of shock success can be sufficiently high such that a caregiver or medical apparatus can make a decision to administer an electrical shock. Alternatively, for relatively low values of AMSA or other frequency-based data, observed changes in frequency-based data can be a substantial contributor to the overall percentage of shock success. Changes in spectral frequency of an ECG can provide further information (in addition to the actual values of the spectral frequency analysis), which can beneficially lead to a therapeutic shock at an earlier time, for example, as compared to a case where only the actual values of the spectral frequency are taken into account. Accordingly, by implementing systems and methods described herein, patients can be able to receive life-saving therapies quickly and effectively.

In some implementations, a therapeutic system can be configured to perform a number of operations. For example, the therapeutic system can include a processor configured to receive signals from sensors to obtain a time domain ECG of a patient, and can further analyze the time domain ECG. Such analysis can include performing a number of time-frequency transformations of multiple portions of the time domain ECG signal from the patient into frequency domain data. Based on the time-frequency transformation(s), the processor can determine a first frequency-based value (e.g., FFT of the ECG data or an AMSA value) over a first evaluation period, and a second frequency-based value representing a trend over a second evaluation period (e.g., upward trend in FFT of the ECG data or in AMSA), where the two evaluation periods can or cannot overlap. Based on these two frequency-based values, the processor can then calculate or otherwise determine (e.g., based on a logistic regression, a threshold based determination, or any other appropriate method) a probability that a particular type of therapy can lead to a successful patient outcome.

The system can then provide an indication of the probability of success to an operator and/or treatment apparatus, for making a decision of whether or not to administer the therapy.

In general, defibrillation is a common treatment for various arrhythmias, such as VF. However, the deliverance of an electrical shock can generate several side effects (e.g., heart tissue damage, skin burns, etc.). Electric shock therapy can require interruptions of chest compressions during the deliverance of the shock. Additionally, the effectiveness of defibrillation can decrease over the elapsed time of an episode—where an episode can be measured from the time when a victim first starts feeling symptoms of a cardiac event (e.g., VF) or loses consciousness. Generally, the time from onset of a VF episode and unconsciousness is relatively short, in the order of tens of seconds. For any given period of time during a cardiac event, it is desirable to predict whether defibrillation can be successful in restoring a regular heartbeat following the onset of an arrhythmic episode, so that suitable levels of shock are administered at appropriate times. It can also be helpful to determine how long it has been since a cardiac event started or in which metabolic stage the patient is in (e.g., a first, second, or third metabolic stage or phase). The techniques described in this document can be used to better predict when a defibrillation shock can be successful and whether to administer treatment at earlier times than recommended by standard, non-personalized protocol. Because the window of time is typically very short, a personalized treatment including the identification of an optimal moment to generate a defibrillation shock can increase the probability that the person experiencing arrhythmia will survive.

Such predictions can each be referred to as an "indicator of success" or, equivalently, a "success indication" within the context of the present disclosure. The determined prediction can be associated with a myocardial viability metric, where myocardium is considered to be viable if during a cardiac event (e.g., VF) it has the potential to recover its function. The prediction can be used so that a defibrillating shock is not provided when the chance of successful defibrillation is low (e.g., the myocardium is not viable), and instead defibrillation is postponed until the chance of successful defibrillation increases to an acceptable level; until such a time, a rescuer can be instructed to provide other care such as regular chest compressions, forceful chest compressions, or other cardiac assistance procedures.

Such a determination about likelihood of successful shock can be used to enhance personalized care in an automatic and/or manual defibrillation procedure. In an automatic procedure, a defibrillator can be designed to condition the generation of defibrillation shocks based on a predetermined threshold of a success metric. In a manual procedure, the success indication can be shown to a rescuer, and the rescuer can determine whether to apply a shock or not based on the indication, or the system can provide other information to the rescuer. For example, the indication of success can show a percentage likelihood for a shock to succeed, or can be a less specific indicator, such as an indication of which phase (e.g., of three phases discussed above and below) the victim is currently in, so that the rescuer can immediately understand, from experience and training related to those phases, that defibrillation attempts are likely to be successful or not.

Additional information provided to a rescuer can take the form of instructions, such as instructions to perform chest compressions or some other action, where the action is selected from among a plurality of possible treatments based on the current phase for the victim. A system can also integrate both (e.g., locking out the ability to provide a shock until a threshold level is reached, and then showing the relative likelihood of success above that value). The likelihood or probability of success can be provided in various manners, such as quantitatively (e.g., by showing an actual percentage), or qualitatively (e.g., showing two or more of a low, medium, or high likelihood of success on an electronic display of a defibrillator).

In certain implementations described herein, the present disclosure is directed to systems and methods for predicting whether defibrillation can be effective using amplitude spectrum area (AMSA) or any other appropriate Shock Prediction Algorithms (SPA) using analysis of ECG data, and adjusting such SPA predictions based on either the existence of prior defibrillation shocks as well as observations of a patient's reaction to those defibrillating shocks. In particular, it has been observed that victims of cardiac fibrillation can successfully defibrillate for lower AMSA threshold values if they have been previously successfully defibrillated during the same rescue session. Thus, rather than treating each shock as a discrete event in analyzing the probability of success, the techniques described here take into account prior shock deliveries, and an observed response of the patient to those deliveries, in determining an AMSA value or other value that can indicate that a shock currently applied to the patient can likely be successful (or not) in defibrillating the patient. Such a determination can also be combined with determinations about trans-thoracic impedance (trans-thoracic impedance) of the patient, as discussed more fully below.

To obtain better predictive value for the AMSA values, the time window from which the ECG data for an AMSA determination is taken can be made relative small (e.g., between 3 and 4 seconds, between 2 and 3 seconds, and between 1 and 2 seconds), which can place the data as close to the current status of the patient as possible. Smaller windows can suffer from edge effects more-so than larger windows, so the shape and coefficients for the windows can also be selected to maximize predictive power of the method. For example, a Tukey window having appropriate coefficients, such as about 0.2, can be employed.

FIG. 1A shows schematically an example combination 100A of various types of data in determining the probability of a defibrillating shock success. In a particular implementation one of the data types can be used alone, or multiple data types can be combined to generate a composite myocardial viability metric (e.g., by giving a score to each type and a weight, and combining them all to generate a weighted composite score for a likelihood). In this example, a shock indication 116 is the outcome of a decision process that can be performed by a defibrillator alone or in combination with one or more pieces of ancillary equipment (e.g., a computing device such as a smartphone carried by a healthcare provider). The shock indication 116 can be provided to a part of the defibrillator (e.g., via an analog or digital signal that represents the indication, so that the receiving part of the defibrillator can cause a shock feature to be executed or to cause it to be enabled so that it can be manually executed by an operator of the defibrillator). The shock indication can also or alternatively be provided to a rescuer (e.g., can be displayed by a defibrillator) so as to indicate that a defibrillating shock can be delivered. In the context of this disclosure, a defibrillating shock is an electrical shock designed to cause cardiac defibrillation, independent of whether it causes a successful defibrillation or not.)

The relevant inputs can obtain at least some of their data from signals generated by a pair of electrodes 102 that can be adhered to a patient's torso—above one breast and below the other, for example, in a typical manner. The electrodes can include leads for obtaining ECG data and providing such data for analysis for a number of purposes. In addition, a CPR puck 104 can be placed on a patient's sternum and can deliver signals indicative of acceleration of the puck, and thus of up-down acceleration of the patient's sternum, which can be integrated so as to identify a depth of compression by the rescuer (and can also be used to identify whether the patient is currently receiving chest compressions or not).

In some implementations, the shape of the window can be asymmetric. For instance, the edge of the window that is "older" in time can have a window shape that results in a greater level of attenuation that does the "newer" portion of the windowed data. Other asymmetric shapes can also be used, as appropriate, to generate data that best represents an accurate prediction of shock success.

The electrodes 102 can be electrically connected to an ECG unit 106, which can be part of a portable defibrillator and can combine data from different leads (e.g., 8 leads) in a familiar manner to construct a signal that is representative of the patient's ECG pattern. Such an ECG signal is often used to generate a visual representation of the patient's ECG pattern on a screen of the defibrillator. The ECG-related data can also be analyzed in various ways to learn about the current condition of the patient, including in determining what sort of shock indication to provide to control the defibrillator or to display to a rescuer.

As one such example, ECG data can be transformed from the time domain into frequency domain data, for example by using FFT module 107. The FFT module 107 can nearly continuously and repeatedly compute a set of frequency-based values, a numeric value or a similar indicator that represents a frequency amplitude at particular different times and/or frequency ranges corresponding to changes during a particular time interval. The frequency domain data can be used to generate a myocardial viability metric and/or it can be used as an input for AMSA analyzer 108. AMSA analyzer 108 can nearly continuously and repeatedly compute an AMSA number, a change in AMSA over time, a change in rate of AMSA relative to time and/or a similar indicator that represents ECG amplitude at particular different frequencies and/or frequency ranges in an aggregated form (e.g., a numeral that represents a value of the amplitude across the frequencies). Generally, the goal is to identify a waveform in which amplitude of the VF signals is large, and in particular, relatively large in the higher frequency ranges. Similarly, power spectrum area can be measured and its change over time can also be used as an input that is alternative to, or in addition to, a change over time in AMSA value for purposes of making a shock indication. As described in more detail above and below, a current AMSA value and/or a change over time in AMSA value can be used to determine whether a shock is likely to be successful. A plurality of combined AMSA values, such as a running average computed several times during a particular time interval (and each covering a time period longer than the time period for the first AMSA value) using a moving window can indicate how much time has elapsed since a cardiac event began. The estimation of the onset of the cardiac event can indicate which phase, of multiple metabolic phases during a VF event, the victim is in. Each metabolic phase is associated with a different most-effective treatment sub-protocol. Also, when rescuers first arrive on a scene, several seconds of ECG data can be used to provide them an initial indication of the time since the event started and/or the phase in which the victim currently is in (e.g., by displaying a number of elapsed minutes or the name of one of multiple phases on a display screen of a medical device such as a monitor or defibrillator/monitor).

The AMSA analyzer 108 can be programmed to perform the analysis of the ECG, and perhaps other, inputs so as to maximize the predictive value of the AMSA value, whether by affecting inputs to the AMSA determination, and/or making an AMSA determination and then adjusting the AMSA value that is generated from that determination. As one example, the size of the window from which ECG data is taken in making the calculation can be set to maximize the predictive value, such as by being about 1 second to about 1.5 seconds long. As another example, the shape of the window can be tapered, such as by being in the form of a Tukey or Hann window, rather than having vertical edges like a boxcar window. Similarly, the coefficients for the window, such as Chi2 and p can be set to maximize the expected predictive value of the calculation. The AMSA analyzer can also be programmed to change such values dynamically over the course of a particular VF incident, either by moving the values progressively as time elapses so as to make the values match known expected values for maximizing the predictive effect of the calculation, or to respond to particular readings, e.g., to use particular window length, form, or coefficients when an AMSA value is in a pre-defined range.

A trans-thoracic impedance module 110 can also obtain information from sensors provided with the electrodes 102, which indicates the impedance of the patient between the locations of the two electrodes. The impedance can also be a factor in determining a shock indication as described in more detail below.

A defibrillation history success module 112 tracks the application of defibrillating shocks to the patient and whether they were successful in defibrillating the patient, and/or the level to which they were successful. For example, the module 112 can monitor the ECG waveform in time windows of various sizes for a rhythm that matches a profile of a "healthy" heart rhythm, and if the healthy rhythm is determined to be established for a predetermined time period after the application of a defibrillating shock, the module 112 can register the existence of a successful shock. If a shock is applied and a healthy rhythm is not established within a time window after the delivery of the shock, the module 112 can register a failed shock. In addition to registering a binary value of success/fail, the module can further analyze the ECG signal to determine the level of the success or failure and may, for example, assign a score to the chance of success of each shock, such as a normalized score between 0 (no chance of success) and 1 (absolute certainty).

A CPR chest compression module 114 can receive signals about the motion of the puck 104 to determine whether chest compressions are currently being applied to the patient, and to determine the depth of such compressions. Such information can be used, for example, in giving a rescuer feedback about the pace and depth of the chest compressions (e.g., the defibrillator could generate a voice that says "push harder"). The presence of current chest compression activity can also signal the other components that a shock is not currently advisable, or that ECG data should be analyzed in a particular manner so as to remove residual artifacts in the ECG signal from the activity of the chest compressions.

Information about pharmacological agents 115 provided to a patient can also be identified and taken into account in providing a shock indication to a rescuer. Such information can be obtained manually, such as by a rescuer entering, via a screen on a defibrillator or on a tablet computer that communicates with the defibrillator, identifiers for the type of agent administered to a patient, the time of administration, and the amount administered. The information can also be obtained automatically, such as from instruments used to administer the particular pharmacological agents. The device that provides a shock indication can also take that information into account in identifying the likelihood that a shock can be successful if provided to the patient (e.g., by shifting up or down an AMSA threshold for measuring shock success likelihood), and for other relevant purposes.

One or more of the particular factors discussed here can then be fed to a shock indication module 116, which can combine them each according to an appropriate formula so as to generate a binary or analog shock indication. For example, any of the following appropriate steps can be taken: a score can be generated for each of the factors, the scores can normalized (e.g., to a 0 to 1 or 0 to 100 scale), a weighting can be applied to each of the scores to represent a determined relevance of that factor to the predictability of a shock outcome, the scores can be totaled or otherwise combined, and an indication can be determined such as a go/no go indication, a percentage of likely success, and other such indications.

In this manner then, the system 100 can take into account one or a plurality of factors in determining whether a shock to be delivered to a patient is likely to be successful. The factors can take data measured from a plurality of different inputs (e.g., ECG, trans-thoracic impedance, delivered agents, etc.), and can be combined to create a likelihood indication, such as a numerical score that is to be measured against a predetermined scale (e.g., 0 to 100% likelihood or A to F grade). Such determination can then be used to control an automatically-operated system (e.g., that delivers chest compressions mechanically), to limit operation of a manually-operated system (e.g., by enabling a shock that is triggered by a user pressing a button), or by simply providing information to a system whose shock is determined solely by a rescuer (e.g., for manual defibrillators in which the operator is a well-trained professional).

FIG. 1B shows an example of a configuration 100B including a victim 122 of cardiac arrest being cared for by a rescuer using a defibrillator 124. The defibrillator 124 includes an electrode package 126 and a compression puck 128 generally coupled thereto. An example of such a defibrillator includes the AED PLUS automated external defibrillator or the AED PRO automated external defibrillator, both from ZOLL Medical Corporation of Chelmsford, Mass. Other embodiments of the defibrillator 124 are possible.

In the pictured example, the victim 122 is rendered prone due to an arrhythmic episode, and the electrode package 126 and the compression puck 128 are positioned on the torso of the victim 122 in an appropriate and known arrangement. In accordance with the present disclosure, the defibrillator 124, in tandem with one or both of the electrode package 126 and the compression puck 128, is configured to determine whether a defibrillation shock can be an effective measure to terminate the arrhythmic episode. The determination is generally based on prior success or failure of defibrillating shocks, one or more trans-thoracic impedance measurements, and one or more calculated changes in AMSA value over time. As shown in the figure, the patient 122 is shown at two points in time—(a) point $t_1$ at which the patient has been defibrillated and is shown with his eyes open and a healthy ECG pattern 135A to indicate such successful defibrillation, and (b) at a later time $t_2$, when the patient has refibrillated and is shown with closed eyes to represent such a state, and with an erratic ECG trace 135B.

The defibrillator 124 is configured to acquire and manipulate both a trans-thoracic impedance signal 130 and an ECG signal 132 via the electrode package. As described in further detail below, a trans-thoracic impedance measurement ($\Omega$) is a parameter derived from the trans-thoracic impedance signal 130 that represents, among other things, thoracic fluid content. An AMSA value (mVHz) is a parameter calculated by integrating the Fourier transform of the ECG signal 132 over a finite frequency range. The AMSA value is one form of calculation that represents a value of an ECG signal from a victim, while other SPA values can likewise be computed.

The defibrillator 124 is further configured to display an indicator 134A/B based on the defibrillating history (determined from ECG data), trans-thoracic impedance measurement(s) and AMSA value(s) obtained from the ECG signal 132, trans-thoracic impedance signal 130 and an ECG signal 132, respectively. The indicator 134A/B generally provides a perceptible cue that suggests whether or not a particular defibrillation event can likely terminate the arrhythmic episode of the victim 122. For example, for the victim 122 at time t1, the indicator 134A displays an X to indicate that no shock should be delivered to the victim 122. In contrast, at time t2, the indicator 134B displays a success indication of "88%," so a rescuer (not shown) can be instructed "Press to Shock," so as to apply a shock to the victim 122 via actuation of a control 137 (e.g., a button that the user can actuate).

In this situation, the indication of an 88% likelihood of success was made by consulting data structure 130, which can be stored in memory of defibrillator 124 upon analysis that occurred around the time of t1, and applying an appropriate calculation to data from the data structure 130. In particular, the defibrillator can analyze ECG data and an indicator provided by shock delivery circuitry in order to determine that a shock was delivered, and at a time soon after, the patient's heart rhythm entered a normal pattern, such that the defibrillator 123 can determine that the shock was a success at time t1. Upon making such a determination, the defibrillator can update data structure 130 to indicate that a successful defibrillation event has occurred during the rescue attempt. Other shocks can also be delivered, and the data structure 130 can be updated to reflect such events, and the success or failure of such events.

Data structure 130 or another data structure can also store information about prior AMSA readings for the victim during the particular VF episode. For example, a separate AMSA measurement and calculation can be made periodically (e.g., multiple times each second, once each second, or once every several seconds) and at least some past calculated AMSA values can be stored in data structure 130. Such values can be combined, and determinations can be made about general values (with low variability because of the combining) and trends in AMSA values, where such determination can indicate information such as the progress of the victim through phases that are generally indicative of the likelihood of success of particular actions taken on the victim by a rescuer. Moreover, such information can be used to generate an indication to a rescuer of the elapsed time (approximate) since the victim entered VF, or an indication of the phase the victim is currently in, among other things.

Embodiments other than those that display percentage likelihood for a shock indication are possible for the one likelihood indication discussed here. For example, it can be appreciated that a success indication can be implemented as any appropriate type of perceptible feedback (e.g., haptic, audio, etc.) as desired. Two simultaneous indications can also be provided, where both can be the same style of indication (e.g., visual display) or different types (e.g., visual display for one and haptic for the other)—e.g., the phase in which a victim is currently located can be displayed on a screen of a defibrillator, while a current AMSA value indicating a relatively high chance of success can be communicated by vibration of or display on a puck on which the rescuer has placed his hands (so as to encourage the rescuer to back-off and provide the shock).

In some implementations, the defibrillator 124 can make the determination of a likelihood of success without expressly notifying the rescuer, and can simply use the determination to determine when to tell the rescuer that a shock can be delivered, or to provide other instructions to a rescuer. In other situations, the defibrillator 124 can explicitly indicate the likelihood of success, such as by showing a percentage likelihood, by showing less discrete gradients for success (e.g., poor, good, very good, and excellent), or by displaying a range of colors (e.g., with red indicating a poor chance and green indicating a good chance). The type of indication that is displayed can also differ based on a mode in which the defibrillator 124 is operating—for example, in a professional mode, more detailed information can be provided, whereas in an AED mode, simpler information (a "go"/"no go" choice) can be presented.

In such manner then, the defibrillator can conduct a number of relatively complex calculations and can combine multiple factors in determining whether to allow a shock to be provided to a patient, or to encourage the application of such a shock by a rescuer.

Figure 1C:
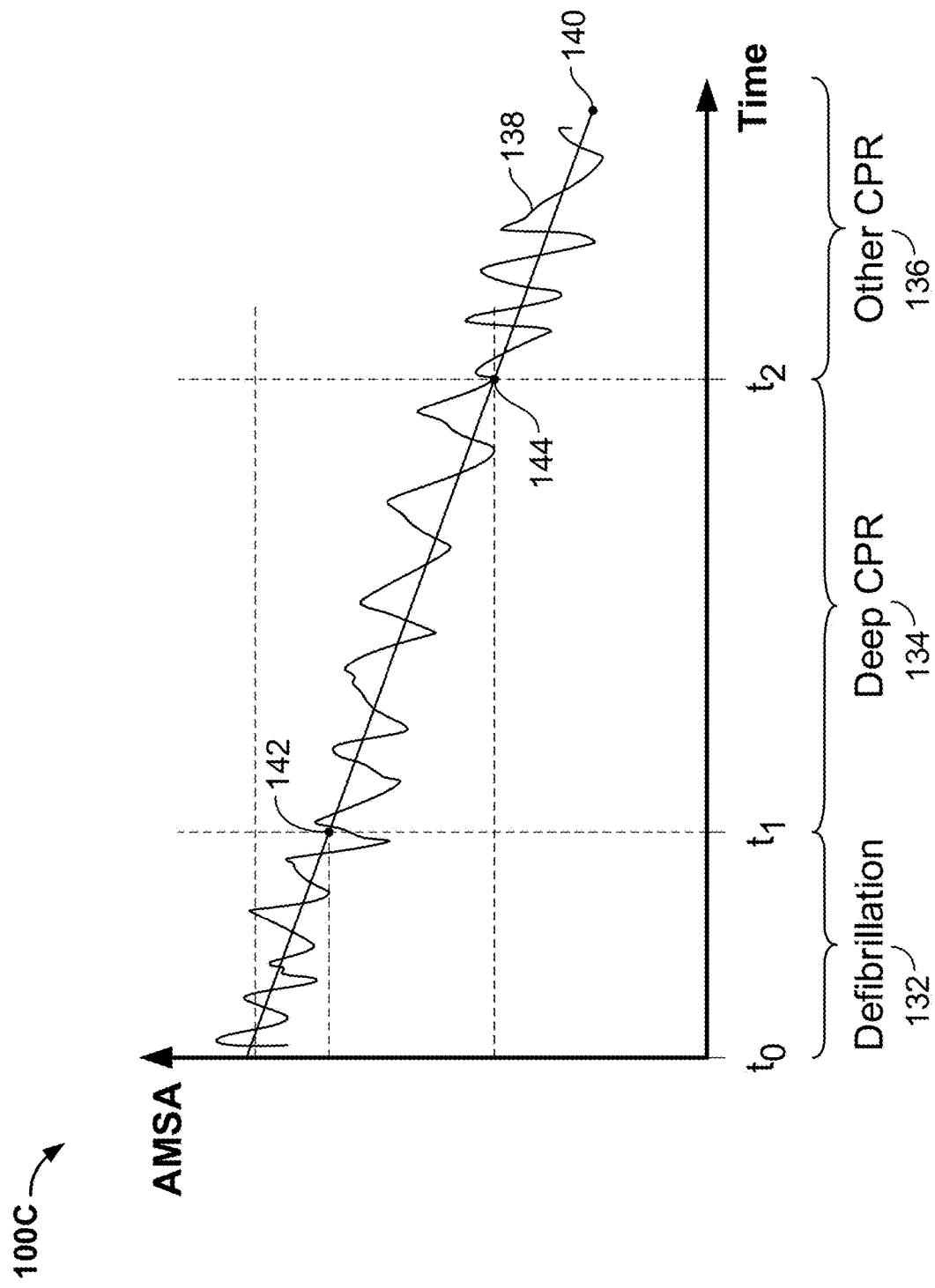
FIG. 1C is a graph that represents example changes in AMSA during an event correlated to phases in the event.

FIG. 1C is a graph 100C that represents changes in AMSA during a VF event correlated to phases in the event. In general, the graph 130 shows how AMSA varies along with variations in a patient ECG, and varies more generally over a longer time period by decreasing over time after the event has started.

The time across this graph can be, for example, about 15 minutes. The time is broken into three phases. A defibrillation phase 133 can represent about the first 4 minutes (plus or minus one minute) of the event. A deep CPR phase 134 can run from about four minutes to about 10 minutes after onset of the event. And an Other CPR phase 136 can represent the remainder of the event, assuming the victim has not been revived by that time.

Line 138 is represented as being drawn through all of the AMSA values computed periodically throughout the time of the event. The line is shown as linearly decreasing for clarity, though AMSA generally decreases exponentially. If AMSA were graphed for a rescuer, it could be shown as an exponential curve, as a line on an exponential scale, and/or with error bars showing statistical variation in the readings.

As can be seen, the AMSA values vary up and down (with a general downward trend over time), and such variation represents changes in the victim's ECG where the changes can represent changes in likelihood that a shock, currently delivered, can be successful. But although there is relatively large variation over short time periods, the variation is less over longer time windows, such as over 10 or more seconds. Thus, for example, AMSA values can be computed periodically over a short time period, and more general values can be computed by averaging or otherwise combining the individual measurements. A running average is represented by line 140. Line 140 can simply represent the average of past computations, and can also be extended into the future in some implementations, such as by linear regression or other appropriate statistical techniques. For purposes of clarity, the overall AMSA value is shown here as decreasing linearly with time, though the actual variation can differ from what is shown here.

In this example, two points on line 140 are particularly relevant, points 142 and 144. These points represent locations at which the combined AMSA value measurement (e.g., averaged over a window of time) decrease below a predetermined value. For example, the value for point 142 can have been selected from observations of ECG data, and corresponding AMSA values from data captured for actual real-world resuscitation events with real victims, and such data can indicate that resuscitation from shock decreases below an acceptable value and/or decreases off more quickly upon passing below a particular AMSA value. Such AMSA value can be selected as a cut-off point that defines the line between the first phase and the second phase. Similarly, such data can indicate that chest compressions or a particular type of chest compressions, such as forceful chest compressions, fell below a particular level of effectiveness or changed relatively rapidly in their effectiveness past another AMSA value. As such, point 144 can represent an AMSA value determined from such data analysis to correspond to such changes as observed across the large population of VF events. The points 142, 144 are mapped to the determined values with horizontal dotted lines, and a defibrillator or other device can monitor the combined AMSA value as an event progresses so as to identify when the predetermined AMSA value is reached. A similar monitoring can be employed with respect to identifying the existence of point 144.

Each of the points 142, 144 is also mapped to the time axis, representing the time at which the particular victim was determined to have transitioned from one phase to another. Generally, the times can be relatively similar as between different victims and different cardiac events, where the changes are driven in large part by ischemic effects that the event has on the heart tissue. At such points in time for the particular victim represented by this graph, the behavior of a medical device such as a defibrillator that is treating the victim can change in the ways discussed above and below.

As such, the device can determine an estimated time since the VF event began using AMSA values and/or other information, where particular AMSA values from a studied population have been determined to correspond to particular times since collapse or other instantiation of the VF event. Such information can be displayed in real-time or stored, such as to determine response times, and to perform studies on effectiveness of rescuers as a function of the time since initiation of the event when a defibrillator is first connected and operable for the victim.

EXAMPLE A

As for particular AMSA values for use in defining points 142 and 144, one example can be instructive. Data from an Utstein-compliant registry along with electronic ECG records were collected on consecutive adult non-traumatic OHCA patients treated by 2 EMS agencies over a 2 year period. Patients with bystander witnessed CA and with VF as initial CA rhythm were included (n=41). AMSA was calculated in earliest pause without compression artifacts, using a 2 second ECG with a Tukey (0.2) FFT window. VF duration was calculated as the sum of the time interval from collapse to defibrillator on and the time interval from defibrillator on to first CPR interruption for defibrillation delivery.

VF duration ranged between 6.5 and 29.6 min (11.3+4.1 min), with a corresponding AMSA between 2.1 and 16.4 mVHz (9.4+4.2 mVHz). AMSA measured in the circulatory phase (N=19) was significantly higher than that in the metabolic phase (N=22) (8.14+3.17 vs. 5.98+2.88, p=0.03). Linear regression revealed that AMSA decreased in the analyzed population by 0.22 mVHz for every min of VF. AMSA was able to predict circulatory phase with an accuracy of 0.7 in ROC area. An AMSA threshold of 10 mVHz was able to predict the circulatory phase with sensitivity of 30%, specificity of 95%, PPV of 86%, NPV of 62%, and overall accuracy of 66%.

FIG. 1D is a table 100D showing examples that relate AMSA to predicted likelihood of failure in defibrillating a victim who has or has not been previously defibrillated. The data was generally analyzed to determine the correlation between AMSA values and prior defibrillation success or failure with respect to success of subsequent defibrillation attempts.

The table shows the results of analysis of 1291 quality defibrillation events from 609 patients. AMSA was calculated for each such set of data based on a 1024 point ECG window that ended 0.5 seconds before each defibrillation. In the data, defibrillation was deemed successful when a spontaneous rhythm existed equal to or greater than 40 bpm and starting within 60 seconds from the shock, and also lasting for more than 32 seconds. A range of AMSA thresholds was calculated and evaluated for the data. The actual results shown in the other tables use the same or similar data.

In summary of the data, where no prior defibrillation had occurred, the mean AMSA for successful shocks was 16.8 mVHz, while the mean for unsuccessful shocks was 11.4 (p<0.0001). For subsequent shocks, the mean AMSA value fell to 15.0 for successful shocks and 7.4 for unsuccessful shocks.

Referring more specifically to the table itself, examples of data from defibrillation events were binned according to different AMSA values applied to the data as AMSA thresholds that would be used to determine whether to apply a subsequent shock. The first column of the table shows the different assigned AMSA values, while the second column shows the number of events that the particular chosen AMSA value correctly predicted, as compared to data indicating whether a defibrillation that was then applied was successful. The last column shows percentages with which the relevant AMSA value would have resulted in an accurate prediction if it had been used in the situations represented by the test data.

The upper section shows statistics for a first defibrillation attempt for each patient, while the lower section shows data for subsequent defibrillation attempts. The data indicates that lower AMSA values can provide more accurate predictions for subsequent defibrillations than for earlier defibrillations.

The upper portion of the table shows a comparison of aggregate mean AMSA values of first versus second shock, second versus third shock, etc. As the data indicates, such AMSA values generally decrease from the first defibrillation attempt to the second, and to a lesser amount generally for each additional defibrillation attempt.

FIG. 1E is a schematic diagram 100E of a data structure for correlating AMSA and prior defibrillation shocks to predicted outcomes for shocking a victim. The data structure here is greatly simplified in an effort to show how AMSA values and determinations about a number of prior shocks (successful or unsuccessful) can be used to predict whether another shock can succeed. This particular table shows correlations for prior shocks generally, though additional tables can be used for identifying correlation for prior successful or unsuccessful shocks.

The table is shown in a format, by which a program or human user could enter at one side of the table to select the value of one input variable, and then move across to the value of another variable, and obtain for an output a percentage likelihood of success, For example, the number of prior shocks are listed across the x-axis at the top of the table, while the percentage likelihood of success is shown along the right edge on the y-axis. The values in the body of the table are AMSA values that have been normalized to a 0 to 100 scale. The actual values are not intended to represent any actual outcome or actual numbers, but simply to indicate the interaction of the various values in coming to a conclusion about a likelihood of success.

Thus, for example, if a patient has received two defibrillating shocks, one would move to the third column of the table and then move down to a measured AMSA number— say 60. One would then move to the right edge to see the percentage likelihood of success—here, 70%. Values between those shown in the cells of the table can be rounded or interpolated or otherwise handled so as to provide likelihoods between each 10% value shown in the data structure.

The likelihood of success identified from the data structure can then be used in various ways to implement the likelihood determination, such as providing the number for the determined likelihood to a microprocessor that can use it to determine whether to enable the shocking capability of a defibrillator and/or to display the value or a related value on the defibrillator for review by a rescuer. Where additional factors (e.g., trans-thoracic impedance) are to be considered, the table can take on additional dimensions, multiple tables can be used, or other techniques for generating a likelihood that is a composite of multiple different factors can be used.

FIG. 1F is a table 100F showing predictions of successful defibrillation for different AMSA threshold values for instances of first defibrillation attempts. The threshold values are listed in the first column, and the cells to the right of each AMSA value indicate particular outcomes for shocks delivered at those AMSA values for initial shocks.

The particular values shown include sensitivity, specificity, positive predictive value (PPV), negative predictive value (NPV), and accuracy, which are statistical measures of the performance of AMSA prediction for shock outcome. Sensitivity indicates the proportion of actual shock successes that were correctly identified. For example, if there were 100 shock successes, and 60 of the 100 were identified by an AMSA threshold of 10 mVHz, then the sensitivity is 0.6 using 10 mVHz as the AMSA threshold. Specificity represents the proportion of shock failures that were correctly identified by the particular AMSA value. PPV is the shock success rate. For example, if 10 mVHz was used as the AMSA threshold to deliver shocks and 100 shocks were delivered with 60 defibrillation successes, PPV=0.6. NPV is the shock failure rate. For example, if 10 mVHz was used as the AMSA threshold for the 100 cases, with AMSA<10 failing to shock, there are 90 cases of failed shock, or NPV=0.9. Accuracy is the proportion of true results (correctly predicted as shock success and shock failure by AMSA) in the total patient population.

FIG. 1G is a table 100G showing AMSA prior defibrillation for refractory and recurrent VF. In particular, the table shows AMSA values that were measured before a defibrillating shock was delivered, and then correlated to whether the shock was successful or not. The first row shows the mean AMSA for all shocks, successful or unsuccessful, broken out by whether refractory VF was present or recurrent VF was present (where mean+/−SEM is shown for each of the values in the table). The second row shows the AMSA, for both refractory and recurrent VF, where the result of the shock was a successful defibrillation, while the third row shows corresponding values for shocks that did not successfully defibrillate. The final row shows the shocks that were successful in defibrillating the subject, both in terms of percentage and numbers. As can be seen, the level of success was much higher for recurrent VF than for refractory VF, and the AMSA was also higher.

FIG. 1H is a table 100H showing prediction of successful defibrillation for increasing AMSA threshold values in the instances of refractory VF. The parameters shown in the table are similar to those shown for FIG. 1E.

Figure 1I:
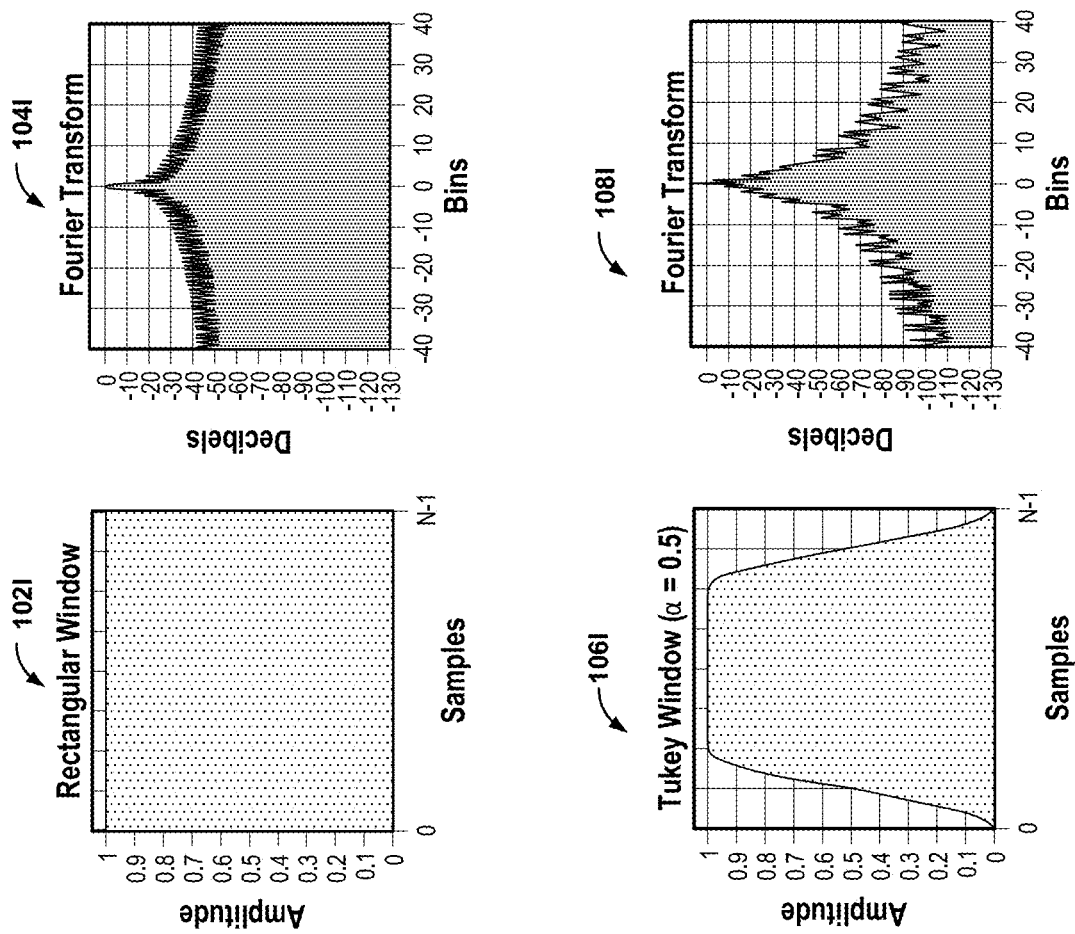
FIG. 1I shows examples of window functions and resulting FFTs from those functions.

FIG. 1I shows examples of window functions 100I and resulting FFTs from those functions. As noted above, window widths in the time domain of less than 4 second down to about one second, less than three seconds down to about one second, and less than two seconds down to about one second, can be used. The figure shows, at the top, a boxcar window that is not tapered and thus can have negative transitory effects introduced into the FFT that it produces. The figure shows, at the bottom, a Tukey window, which is tapered as a sine wave, and is capped at a maximum value before coming down on the back side according to the decreasing value for the sine wave. The window thus lessens the effect of transients cause by the sudden switching of the boxcar window.

Figure 1J:
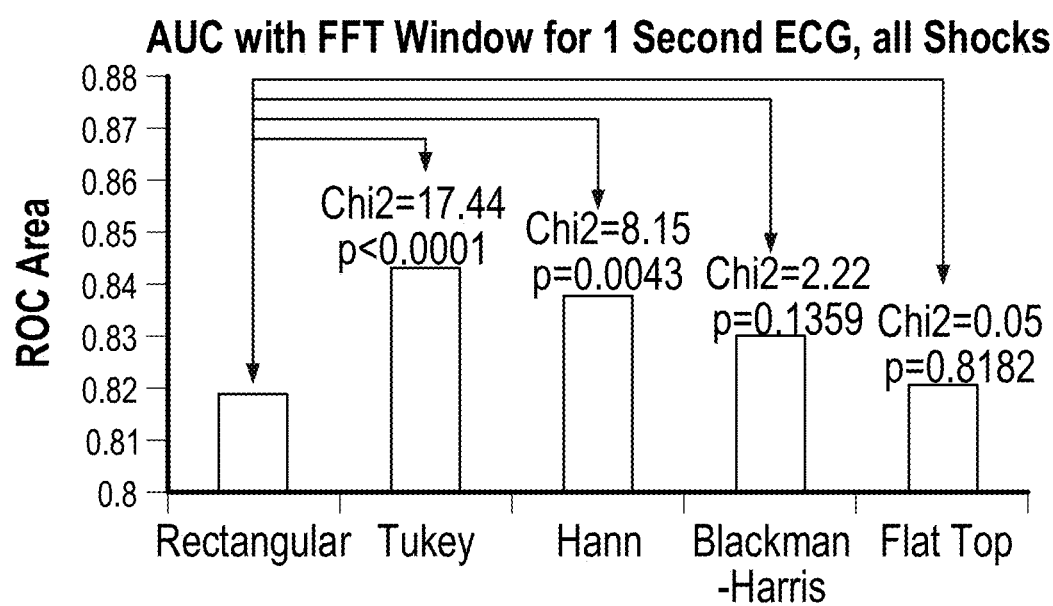
FIG. 1J is an example graph of area under curve for different windows.

FIG. 1J shows a diagram 100J including ROC (receiver operating characteristic) Area values for five different window functions applied to a one second window of ECG data. In this example, digitalized ECG recordings were collected from multiple emergency medical services in the U.S. through a regular field case submission program. The sampling rate of all the ECG data files was 250 Hz. An episode of 1.025 seconds (256 data points, sample rate 250 Hz) waveform ending at 0.5 seconds before each shock attempt were selected for analysis. Five windowing functions were used for analysis. Shock success was defined as an organized rhythm that was present for a minimum of 32 seconds, starting within 60 seconds after the shock, and that had a rate of 40 beats per minute or greater.

Some values shown in the figure have diagnostic value when used in combination with the methods discussed here. For example, when comparing one method of analysis to another, a "p-value" provides a measure of a difference between two groups of measurements, with lower p-values generally being better compared to higher p-values. By statistical convention, a value of $p<0.05$ is considered to be statistically significant. An Area under the Curve ("AUC") measures the area under the ROC curve. The "squarer" the ROC curve is, the greater the accuracy of the diagnostic in general; the AUC is greater for "squarer" curves. The Chi-square test is a simple statistical comparison of the probability distribution of two or more groups where the outcomes are binary.

A total of 1291 shocks (321 successful) from 609 patients with witnessed VF were included in the analysis. As shown in FIG. 1J, a Tukey window (R=0.2) resulted in significantly higher area under the ROC curve compared to other FFT windows.

Thus, as shown by this study, a defibrillator or other device as discussed above and below can be programmed to make AMSA determinations for purposes of predicting a likelihood of successful defibrillating shock using a Tukey window of a width of about 1 second. In other instances, it can be determined that one of the other three types of tapered windows is appropriate, or at least more appropriate than the non-tapered rectangular, or boxcar, window function. Similarly, multiple different window functions can be used for a particular patient, and an AMSA value can be generated from a combination of the different window function readings.

Each of these tables represent values that can be provided as parameters for the operation of a device that determines likelihood of success for a shock or provides other determinations for use in providing care to a patient suffering from VF. For example, the values determined from testing a large number of past events can be used as values that determine the likelihood values that a device correlates with a particular AMSA value at a particular time after VF starts. In this manner, then, data from observations of care provided to prior patients can be used to program a system for providing better case to future patients, particularly with respect to providing guidance on when a shock is likely to be successful in defibrillating the patient.

Referring to FIG. 1L, a chart 100L tabulates AMSA data from an investigation in which CPR was simulated by using extracorporeal circulation (ECC) on open-chest swine. During the investigation, VF was induced and each (of eight) swine were left untreated for eight minutes. After this eight-minute time period, the ECC was initiated and maintained for a ten minute period while the flow was adjusted to produce a coronary perfusion pressure (CPP) of 10 mmHg. After delivery of an initial defibrillation shock, the ECC flow was increased and titrated to secure a mean aortic pressure of 40 mmHg and additional electrical shocks were delivered at 60 second intervals. In this model, defibrillator shock success was defined as organized rhythm lasting more than 5 seconds. As represented in the chart, blood flow in the left anterior descending (LAD) coronary artery relative to baseline LAD blood flow was determined and represented as a quantity (identified as "LADrf"). Absent intervention, AMSA values generally decline in a progressive manner over time during VF. From collected data, based upon the completion of the ECC and prior to applying defibrillation shocks, the animals were assigned to one of two groups. In one group (represented in the chart of FIG. 1L as "Grp 1" and of which four animals were assigned), there was no change or a decrease in AMSA values (i.e., change in mean value being −1.1±1.2) over the time period of the start of ECC to end of ECC. For the second group (represented in FIG. 1L as "Grp 2"), which contained the remaining four animals, the data reported an increase in AMSA values (i.e., change in mean being+3.7±2.7) with all animals showing a progressive increase in AMSA over the period of start of ECC to end of ECC. Regarding the LADrf flow just prior to first shock being administered, the flow trended higher for the Group 2 animals, compared to the Group 1 animals. As such, the AMSA values and the LADrf flow quantities collected from the Group 2 animals have larger and thereby better levels than the corresponding quantities of the Group 1 animals. The chart also reports, for each group, the period of time to a successful defibrillation shock. In particular, in Group 2 animals a successful first shock was achieved in less time than in Group 1 animals (e.g., approximately 721 seconds for Group 2 versus 837 seconds for Group 1).

Based upon these quantities, in particular the AMSA values, the Group 2 animals have a better predicted likelihood of shock success compared to the Group 1 animals, which generally to achieve a successful first shock after a longer period of time. As such, from the chart data, AMSA values (calculated prior to defibrillation), temporal trends in the data, etc. can be used for treatment determinations. For example, for relatively flat or decreasing trends in AMSA values, CPR efforts can be recommended until the AMSA values change (e.g., increase, a positive trend is measured, etc.). Translated into clinical terms, if CPR is being performed on a patient and the AMSA values increase to show a positive trend, the likelihood of a successful shock can be considered higher than if it were a trend of little or no change, i.e. insignificant change, or a decreasing trend. For instance, the series of transform values, such as AMSA can be considered to have a trend of insignificant change (or a decreasing trend) if AMSA increases by less than 10% over the course of one minute of resuscitation treatment. Statistical analyses such as control charts, change point analysis, or other time series analyses can be employed to determine whether the series of transform values changes over a period of time to a threshold degree. Alternatively, the shape of the transform value trend can also be analyzed to determine if AMSA has stopped increasing, and/or is substantially flat. In some implementations, at the time when AMSA is at a maximum (or within a predetermined range of the maximum), but before being at the maximum (or within the predetermined range) for more than a threshold amount of time (e.g., 32 seconds), it can be desirable to deliver a shock. In some implementations, it could be desirable to deliver a shock before the transform value starts to decay. This can be indicated, for example, in the shape analysis of the trend as a zero-crossing of the first derivative (or the second derivative exceeding a negative value above a threshold). However, if the AMSA values remain relatively flat (or decrease) as CPR is being performed, the rescuer can be recommended to continue chest compressions, to provide a pharmacologic agent (i.e., epinephrine) to increase central blood pressures, to change their chest compression technique (e.g., perform deeper compressions, compressions of faster rate, etc.), or to perform another intervention technique to increase the AMSA values (and correspondingly increase the likelihood of a successful shock).

Figure 1K:
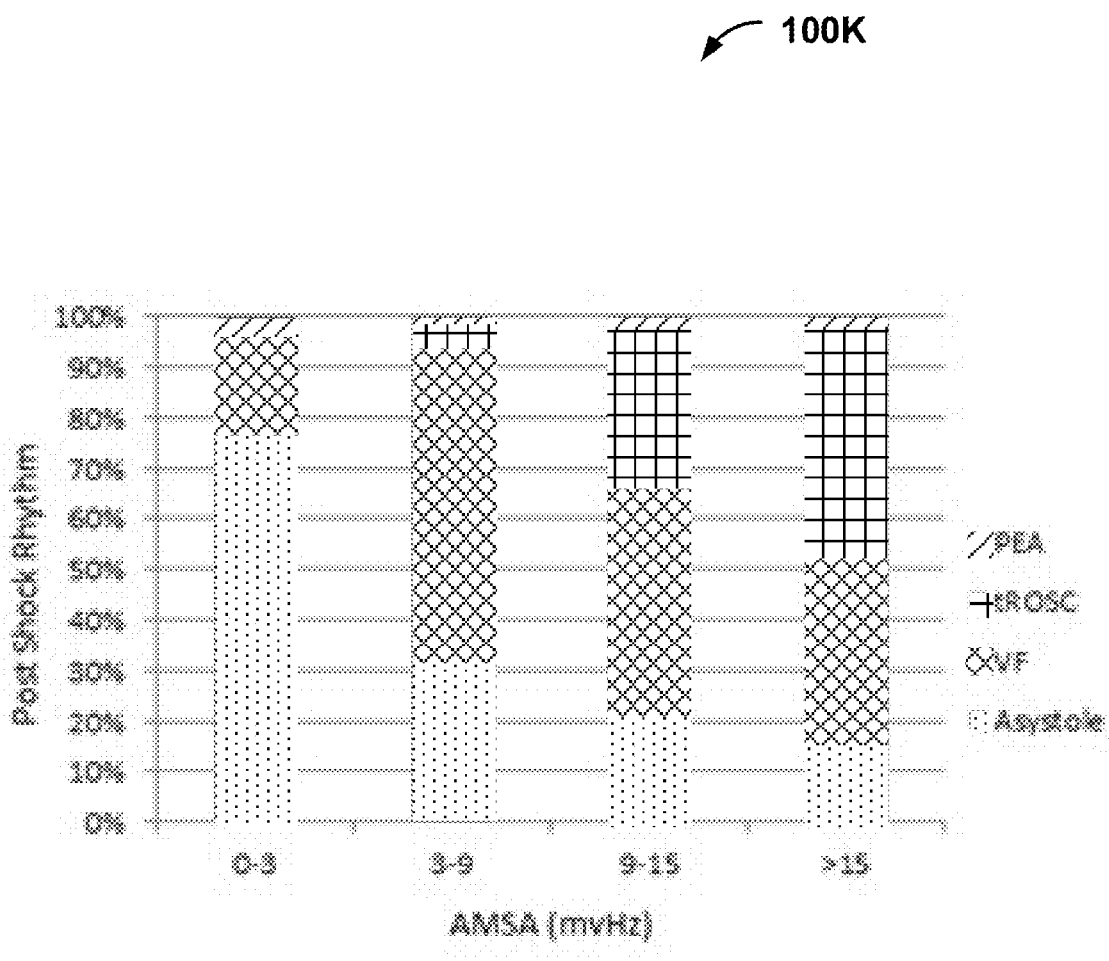
FIG. 1K is an example graph of post-shock rhythm for different AMSA ranges.
Figure 1M:
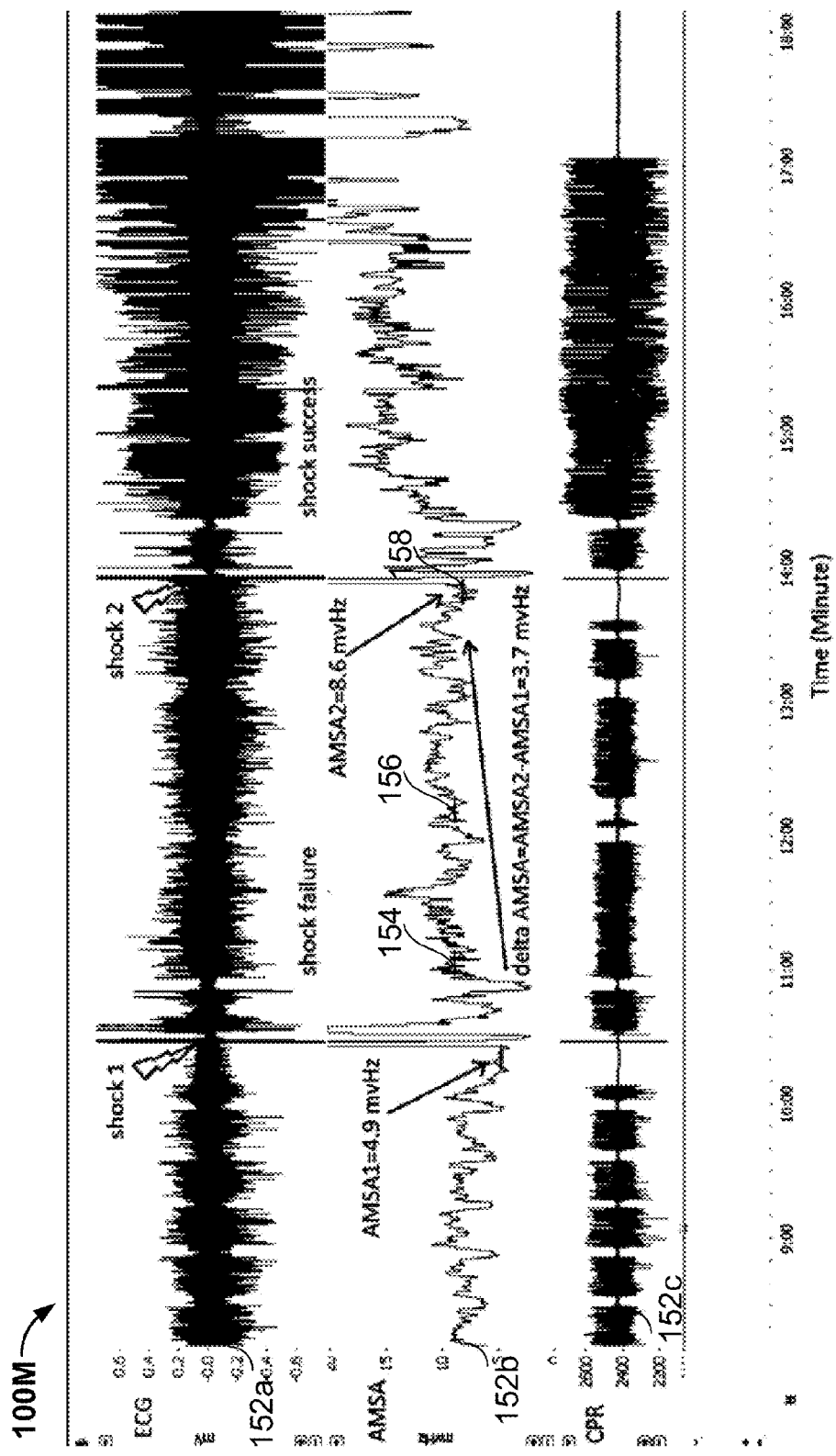
FIG. 1M is an example display including ECG, AMSA and CPR representations.

FIG. 1M is an example of a graphical representation 100M that can be displayed by a patient monitoring and/or treatment device. The example graphical representation 100M includes a parallel display of an ECG signal 152a, AMSA 152b, corresponding to the ECG signal, and a CPR signal 152c, recorded in parallel with the ECG signal. Line 152b is represented as AMSA values computed periodically throughout the allotted time period, including during cardiac treatment (e.g., CPR).

The example graphical representation 100M illustrates AMSA 152b in a patient suffering of VF, being treated with CPR according to standard protocol (e.g., completing 2 minutes of CPR between each single defibrillation attempt). In the illustrated example, two defibrillation shocks were delivered to the patient. The first shock, which failed, was delivered at around 10 minutes and the second shock, which succeeded, was delivered at around 13 minutes. The average AMSA value measured over a period of few seconds prior to the first shock (AMSA$_1$) was about 4.9 mVHz, which is below an early shock threshold, such as approximately 12 mVHz, approximately 13 mVHz, approximately 14 mVHz, approximately 15 mVHz, or another threshold value. The average AMSA value 158 measured over a period of few seconds prior to the second shock (AMSA$_2$) was about 8.6 mVHz. The general trend of AMSA 152b over time illustrates a generally increasing trend between AMSA$_1$ and AMSA$_2$, notably during CPR pauses.

In this example, three points on the AMSA line 152b are particularly relevant, corresponding to certain evaluation periods: points 154, 156 and 158, which were calculated during CPR pauses to avoid compression artifacts. These points represent evaluation periods at which the combined AMSA value measurement (e.g., mean or median value determined over a window of time) are below a predetermined value associated with defibrillation success, but the change from the first recorded AMSA value AMSA$_1$ (4.9 mVHz) to each of these three points can be used as indicators of defibrillation success. For example, referring to point 156 (taken at a time when there is a pause in CPR compressions, which can generally provide for more reliable AMSA values than when CPR compressions are being administered), the respective AMSA value is about 9 mVHz, which corresponds to a change in AMSA of approximately over 4 mVHz. Such a change in AMSA is indicative of a relatively high likelihood of shock success, at least comparable or greater than the AMSA value at point 158. Such data can indicate that analyzing AMSA in parallel with or in between CPR signals can assist a rescuer in providing successful defibrillation therapy at time intervals different than the standard protocol, defining a personalized treatment optimized for each patient, which can be materially different for different patients. For instance, as shown above, because the change in AMSA from the first recorded AMSA value AMSA$_1$ to point 156 is substantial, the system can provide a recommendation and/or decision for the patient to be treated with an electrical shock at a time (e.g., point 156) prior to the standard treatment protocol, rather than withholding shock treatment until point 158.

Figure 1N:
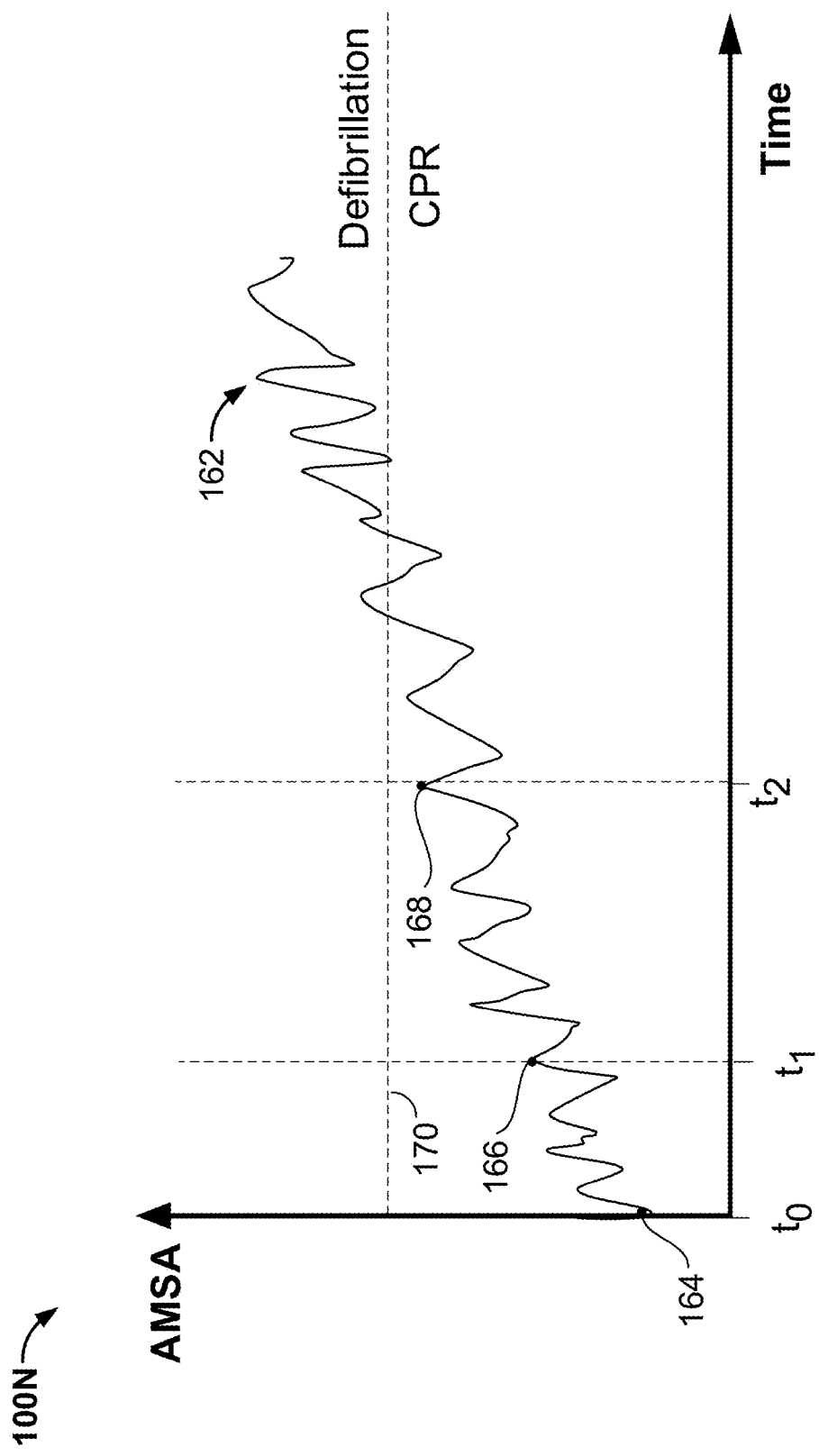
FIG. 1N is another example display including an AMSA representation.
Figure 10:
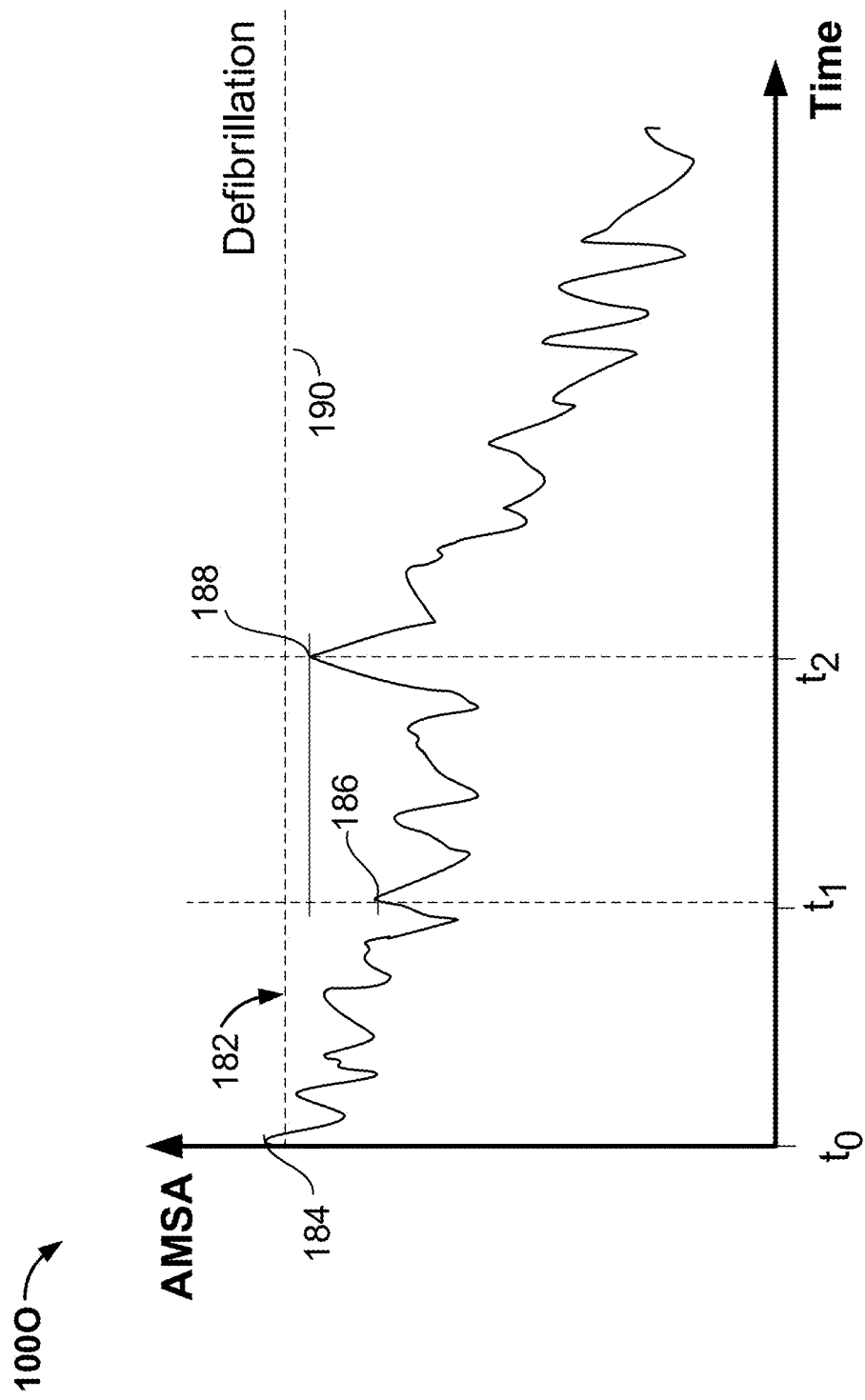

FIG. 1N is another example of a graphical representation 100N that can be displayed by a patient monitoring and/or treatment device. The example graphical representation 100N includes an AMSA trend 162 of a patient receiving cardiac therapy, such as CPR. Line 162 is represented as being drawn through a portion or all of the AMSA values computed periodically throughout the time of a cardiac treatment (e.g., CPR). As illustrated, AMSA values fluctuate over time, and such variation represents changes in the victim's ECG where the changes can represent changes in likelihood that a shock, currently delivered, can be successful. But although there is relatively large variation over short time periods, the variation is less over longer time windows, such as over 10 or more seconds.

For example, AMSA values can be computed periodically over a short time period, and more general values can be computed by averaging or otherwise combining the individual measurements. In some implementations, AMSA can be displayed as a running average. For example, line 162 can represent the average of past computations, and can also be extended into the future in some implementations, such as by linear regression or other appropriate statistical techniques.

Each of the points included in the AMSA trend 162 (e.g., points 164, 166 and 168) can be mapped to the time axis. The first determined AMSA value (e.g., point 164 measured at to) can be above or below a predetermined defibrillation threshold (e.g., 15 mVHz). Generally, the first determined AMSA value varies between different victims and different cardiac events, where the changes are driven in large part by ischemic effects that the event has on the heart tissue.

FIG. 1N further depicts a line 170 that indicates a threshold above which a defibrillating shock is advised. When the AMSA trend 162 exceeds this threshold, the overall percentage of shock success can be relatively high, in which a shock can be recommended. Though, when the AMSA trend 162 remains below this threshold, the change in AMSA can be more relevant to determining the overall percentage of shock success.

Figure 1P:
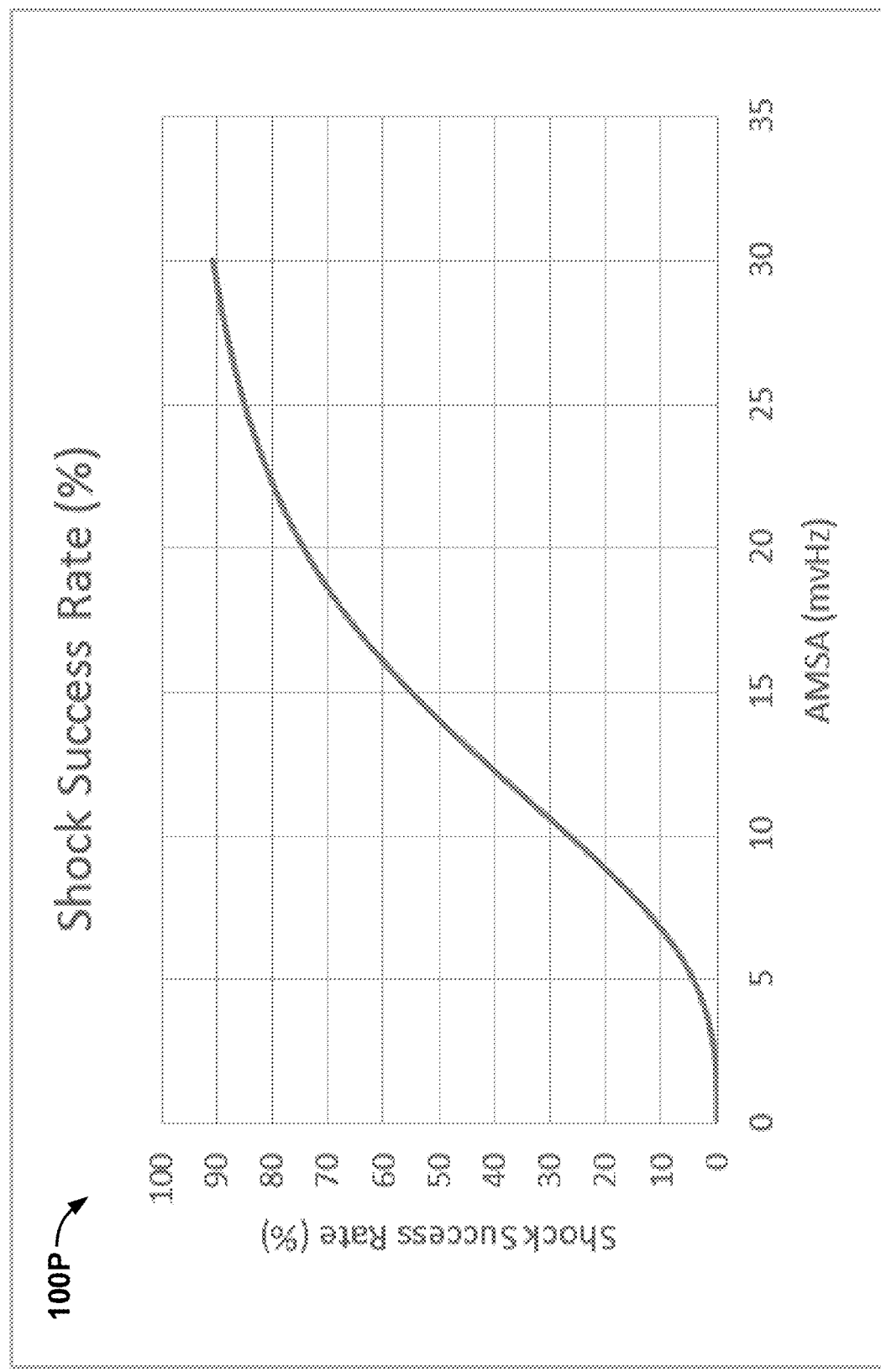
FIG. 1P is an example defibrillation dose-response curve.

As noted herein, the actions performed by a medical device, such as a defibrillator, can be guided or triggered by one or more AMSA values. For example, if initial AMSA value is above a predetermined defibrillation threshold (e.g., 15 mVHz corresponding to 60% probability of successful defibrillation) a defibrillation shock can be delivered. In some implementations, a lookup table or graph, such as the shock success rate to AMSA curve illustrated in FIG. 1P can be used to directly identify the probability of successful defibrillation corresponding to each measured initial AMSA value. The formula that describes the relationship between the initial AMSA value and the probability of successful defibrillation, shock success rate=$1/(1+(AMSA/Constant)^3)$ can also be used. The constant can be associated to one or more physical parameters, such as the energy of a defibrillation shock.

Figure 1R:
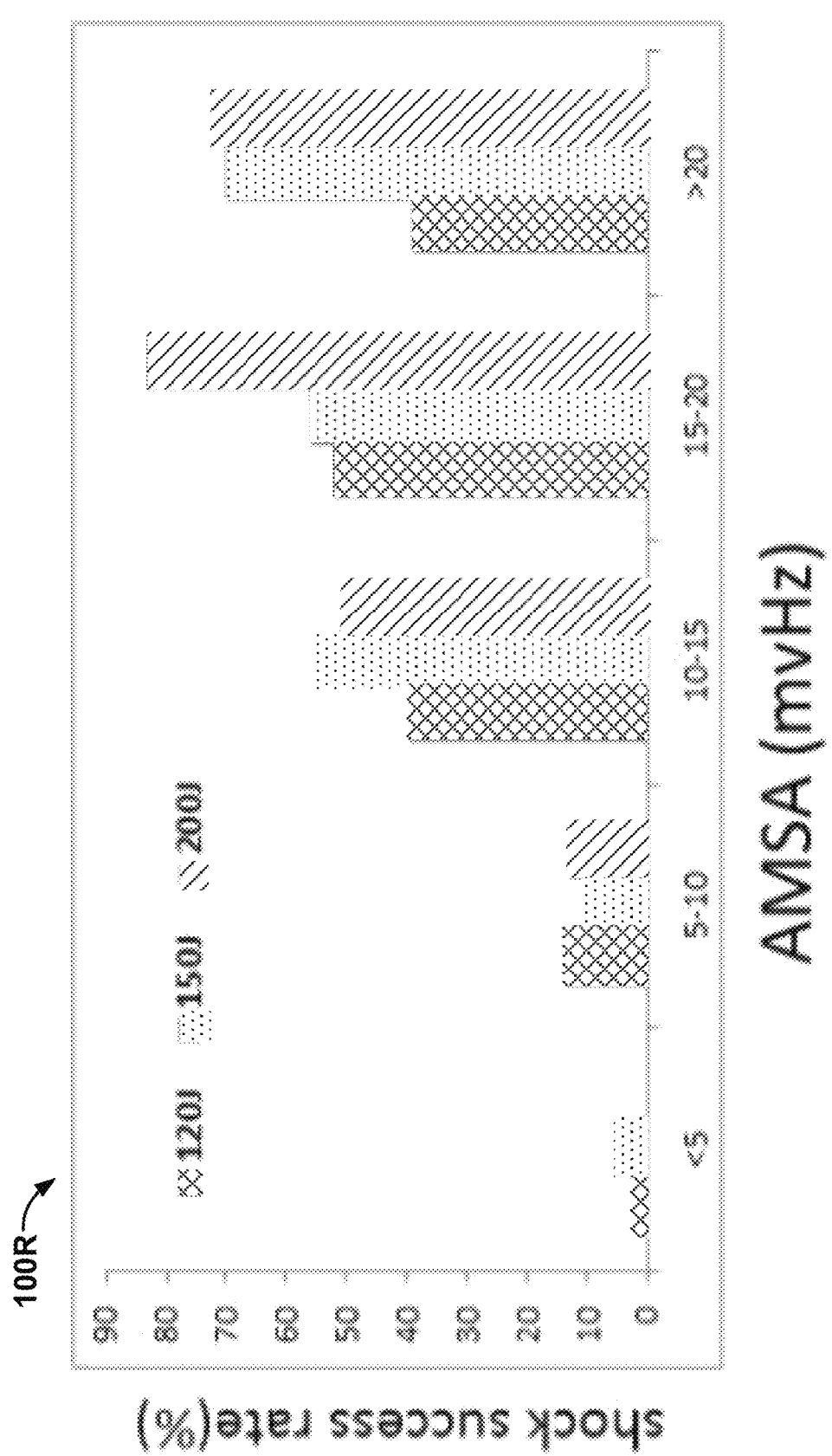
FIG. 1R is a representation of defibrillation success rate as function of AMSA.

In some implementations, experimental values such as the measurement results 100R illustrated in FIG. 1R can also be used as a guide to directly identify the probability of successful defibrillation corresponding to each measured initial AMSA value. The shock of success can vary as a function of AMSA and other parameters, such as the energy of the defibrillation shock. The medical device can automatically process the detected AMSA and use one of the described methods of determining shock success or any other methods appropriate for determining shock success to provide an indicator to the user of the medical device. The indicator can include a numerical display of the probability of success, a written recommendation and/or a visual display based on the graphs illustrated in FIGS. 1P and 1R.

If AMSA value is below the predetermined defibrillation threshold (e.g., 15 mVHz) AMSA value can be continuously monitored and the change in AMSA between times $t_1$ and $t_0$ or $t_2$ and $t_0$ can be used to determine when and if a defibrillation shock can be delivered. For a majority of patients with low initial AMSA (as illustrated in FIG. 1M), CPR cannot be able to generate an increase of AMSA to reach the early shock threshold, such as approximately 12 mVHz, approximately 13 mVHz, approximately 14 mVHz, approximately 15 mVHz, or another threshold value. In some implementations, an upward overall trend (e.g., linear, non-linear, average increase over time) in AMSA can be used as an indicator that defibrillation can be successful. For example, an absolute change in AMSA determined as the difference between an initial AMSA value 164 and a later AMSA value (e.g., 166 or 168) can be calculated. The change in AMSA value over time can be used in determining a probability of defibrillation success. In some implementations, each unit increase in AMSA, can be associated to a particular percentage increase of the odds of shock success, for example, as illustrated in FIGS. 1Q and 1S. The upward trend in AMSA (or other frequency-based value, as illustrated in FIG. 1S) over time can be determined over any suitable time period in which resuscitation and/or therapeutic activities are occurring. In some cases, the upward trend can occur for a short, fleeting period, leading to a short interval of opportunity in which the administration of a shock or other appropriate therapy is likely to be successful, despite a generally downward trend over a longer period. The change in AMSA, and, in particular the identification of an upward trend, can be calculated or otherwise determined via any suitable mathematical method. For example, the change in AMSA can be estimated based on calculating a slope of a line intersecting two or more AMSA points, by using a polynomial function, by implementing a non-linear function, calculating a spline estimation, by determining the derivative, by using regression analysis, by applying interpolation techniques, and/or other methods familiar to those of skill in the art.

In some implementations, a change in AMSA can be a more sensitive indicator for shock success in patients with low initial AMSA and a metric derived from the change in AMSA can be useful to guide CPR efforts, including timing of shock delivery. In some implementations, a table or an odds ratio-AMSA range curve can be used to directly identify the increase in defibrillation success for each mVHz change in AMSA, as illustrated in FIGS. 1Q and 1S, respectively.

FIG. 1O is another example of a graphical representation 100O that can be displayed by a patient monitoring and/or treatment device. The example graphical representation 100O includes an AMSA trend 182 of a patient who might not be responding at all times to the received cardiac therapy and a line 190 that indicates a threshold above which a defibrillating shock is advised. Line 182 is represented as being drawn through a portion or all of the AMSA values computed periodically throughout the time of a cardiac treatment (e.g., CPR). As illustrated, AMSA values fluctuate over time, and such variation represents changes in the victim's ECG where the changes can represent changes in likelihood that a shock, currently delivered, can be successful.

Each of the points included in the AMSA trend 182 (e.g., points 184, 186 and 188) can be mapped to the time axis. First AMSA value (e.g., point 184 measured at $t_0$) can be above a predetermined defibrillation threshold (e.g., 15 mVHz) and can quickly (e.g., within seconds) drop under the predetermined defibrillation threshold. Generally, the first determined AMSA value varies with the time from the onset of the cardiac event and it can also vary between different victims and different cardiac events.

As illustrated in FIG. 1O, AMSA values with a generally decreasing trend can include a temporary increase in AMSA value. For example, a patient can positively respond to applied CPR therapy, or another circulation-inducing therapy, for a limited period of time. The improvement in myocardial viability can be reflected by an increase in AMSA. In some patients AMSA value can increase above a predetermined defibrillation threshold (e.g., 15 mVHz), reaching a value at which a shock can be recommended. Or, for some patients, as illustratively shown in FIG. 1O, AMSA trend 182 can remain below this threshold, yet a change in AMSA (e.g., between AMSA point 186 measured at $t_1$ and AMSA point 188 measured at $t_2$) recorded during a short time interval can indicate an increase in the overall percentage of shock success.

In some implementations, an absolute change in AMSA determined as the difference between an initial AMSA value 184 and a later AMSA value (e.g., 186 or 188) can be calculated. The change in AMSA value over time can be used in determining a probability of defibrillation success. In some implementations, each unit increase in AMSA, can be associated to a particular percentage increase of the odds of shock success. A table or an odds ratio-AMSA range curve can be used to directly identify the increase in defibrillation success for each mVHz change in AMSA, as illustrated in FIGS. 1Q and 1S, respectively.

FIG. 1Q is a table 100Q showing predictions of successful defibrillation for different AMSA ranges for instances of first defibrillation attempts, corresponding to each mVHz change in AMSA. The initial AMSA values are listed in the first column and the cells to the right of each AMSA value indicate particular outcomes for shocks delivered at those AMSA values for initial shocks. FIG. 1S illustrates an example graph 100S depicting predictions of successful defibrillation for different AMSA ranges for instances of first defibrillation attempts, corresponding to each mVHz change in AMSA. In some implementations, the entire range of initial AMSA values that are lower than 6.5 can be associated to an odds ratio of 2.675. The initial AMSA values and the change in AMSA can be used to determine a probability of defibrillation success by using the following formula: shock success rate=odds of shock success/(odds of shock success+1). It can be appreciated that other methods of determining the odds of shock success, and ultimately the percentage of shock success, as a function of an initial (or other) AMSA value and/or trend of AMSA values can be employed.

As an illustrative example, a patient can present an initial AMSA value of 8.1 mVHz, which according to the dose-response graph 100P (illustrated in FIG. 1P) corresponds to approximately 20% of shock success rate. As indicated by FIGS. 1Q and 1S, for such a patient, each unit increase in AMSA corresponds to 20/80=25% increase in odds of shock success. After one minute CPR, if AMSA value steadily increased to 12 mVHz (4 units of increase in AMSA), the odds of shock success increased by 336%, corresponding to 1.04 in odds of shock success. This is equivalent to the probability of shock success, or shock success rate, of 1.04/(1+1.04)=51%, which could be a good indication for an early defibrillation. For such patients, even though AMSA value did not reach the preset threshold of 15 mVHz for the early shock, by using a sustained change in AMSA as an indicator, the patient could be identified as benefiting from an early shock. It should be appreciated that the above example is provided for illustratively purposes only and that other manners of calculation and calibration can be possible. For example, as discussed below, it can be possible to provide a robust statistical regression analysis with appropriate coefficients where the model takes two inputs of spectral frequency (e.g., AMSA value and change in AMSA over time, frequency value and change in frequency over time) and outputs an overall predictor (e.g., percentage) of shock success.

Figure 1T:
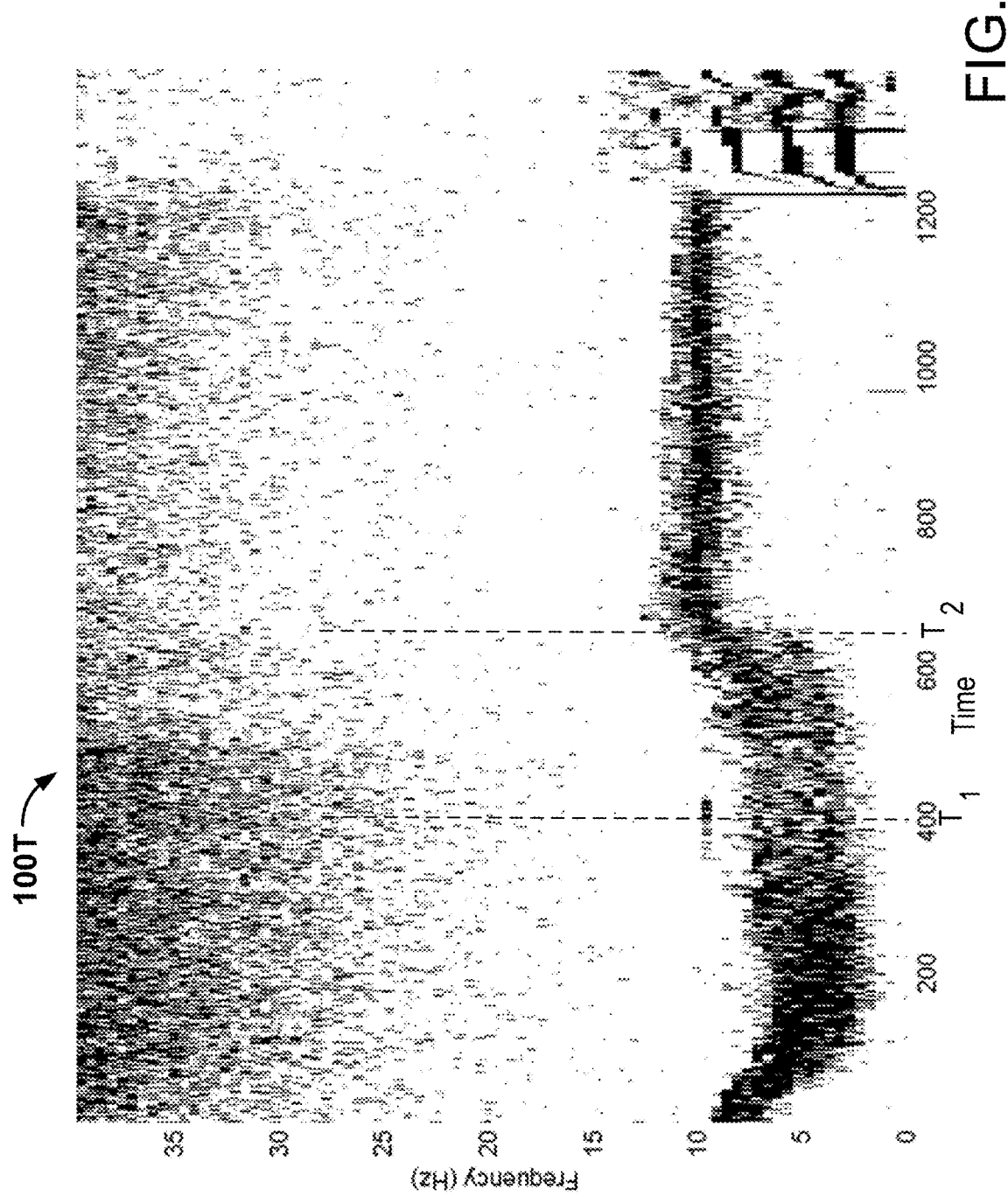
FIG. 1T is an example display including an FFT representation.

FIG. 1T is an example spectrogram 100T derived from an ECG signal corresponding to a heart presenting VF. The spectrogram can be used to derive AMSA values or other frequency-based data as a function of time and/or they can be used to directly derive a metric indicative of myocardial viability (e.g., without converting the frequency values to AMSA). The metric can be compared to a predetermined threshold to decide whether to apply a defibrillation shock or not or it can be used to evaluate a trend in frequency change. The illustrated example presents a VF that is initially treated by extracorporeal circulation, which is started at approximately 400 s. The spectrogram indicates a steady increase in frequency in response to the induced artificial circulation. In some implementations, an absolute peak value, a change in frequency or a change rate in frequency can be used to determine a metric that estimates the probability of successful defibrillation and to provide a recommendation for a defibrillation shock. In the illustrated example, the peak recorded at around 650 seconds and/or the change in frequency between 500 seconds and 600 seconds can be used as indicators of successful defibrillation.

EXAMPLE B

Figure 1U:
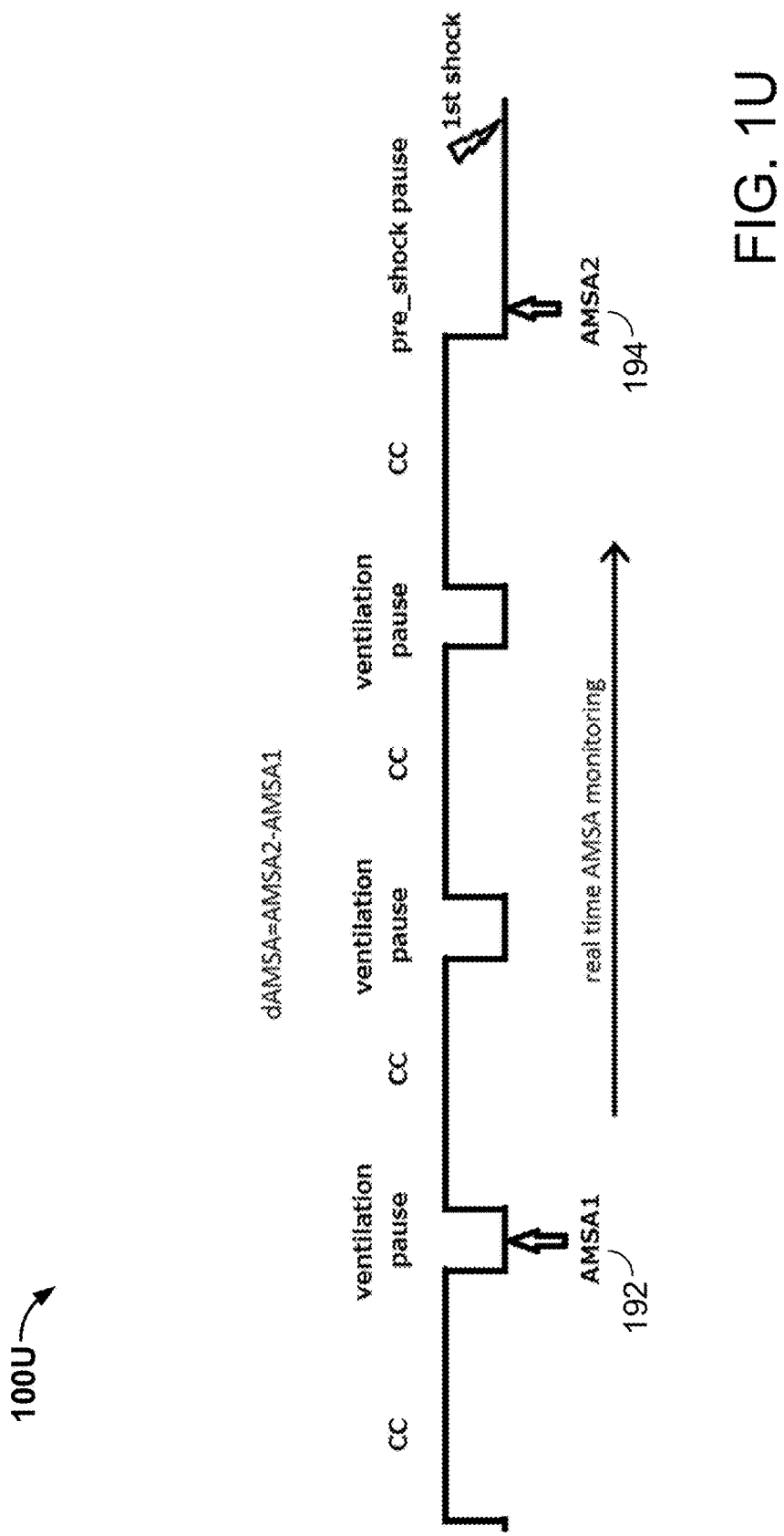
FIG. 1U is an example of where a change in AMSA is monitored during the course of CPR.

FIG. 1U illustrates a schematic diagram 100U of a method in an example that was used to investigate whether a positive change in AMSA in response to CPR would predict resuscitation outcome for return of spontaneous circulation (ROSC). In this example, the illustrated method was applied as a retrospective analysis of out-of-hospital cardiac arrest patients. A single centre database of electrocardiographic defibrillator records collected from 2007 until 2013 including 248 patients with bystander or emergency service (EMS) witnessed cardiac arrest and VF as first recorded rhythm was used for analysis. Accordingly, this study provides a greater level of confidence in the effectiveness of using an initial frequency-based value (e.g., initial AMSA) and a frequency-based trend (e.g., change in AMSA) as sufficient inputs in determining the probability of success from administering one or more therapeutic interventions (e.g., defibrillation shock, compressions, ventilation). In this example, a random sample of 82 records was extracted and analysed, excluding cases with missing data, no artefact free compression pauses, or less than 60 seconds of compressions between first compression pause and first shock. Initial AMSA ($AMSA_1$ 192) was measured during the first compression pause using a 2.1 second window. Post-CPR AMSA ($AMSA_2$ 194) was measured two seconds after the last chest compression before the first shock. Change in AMSA ($\Delta AMSA$) was calculated as $\Delta AMSA = AMSA_2 - AMSA_1$. Admission to emergency department with ROSC lasting for at least 60 seconds was used as the end point. In this example, ER admission was an indicator for shock success for the patient.

The overall emergency room (ER) admission rate was 78%. The univariable logistic regression results of all cases are included in table 1.

TABLE 1

| ER Admission | Odds Ratio | 95% CI | | p |
|---|---|---|---|---|
| $AMSA_1$ | 1.40 | 112 | 1.74 | 0.003 |
| $\Delta AMSA$ | 1.03 | 0.77 | 1.40 | 0.83 |

The univariable logistic regression results for $AMSA_1 < 7.5$ mVHz are included in table 2.

TABLE 2

| ER Admission | Odds Ratio | 95% CI | | p |
|---|---|---|---|---|
| $\Delta AMSA$ | 1.78 | 0.98 | 3.22 | 0.059 |

The multivariable logistic regression results of all cases are included in table 3.

TABLE 3

| ER Admission | Odds Ratio | 95% CI | | p |
|---|---|---|---|---|
| $AMSA_1$ | 159 | 1.21 | 2.09 | 0.001 |
| $\Delta AMSA$ | 155 | 1.002 | 2.41 | 0.049 |

Multivariable logistic regression showed that both $AMSA_1$ and $\Delta AMSA$ were independent predictors of ER admission with odds ratios of 1.59 (95% confidence interval CI 1.21-2.09, p<0.001) and 1.55 (95% confidence interval 1.002-2.41, p<0.049) for each mVHz increase in initial AMSA or $\Delta AMSA$, respectively.

In analysed VF patients, a high initial AMSA value predicted an increased likelihood of ER admission (i.e., shock success). An increase of AMSA in response to CPR also predicted a higher ER admission rate. Monitoring of AMSA during resuscitation therefore may be useful to guide CPR efforts, possibly including timing of shock delivery. The findings support the value of AMSA and/or other frequency-based calculations as indicator of myocardial viability and predictor of therapeutic success.

Figure 2:
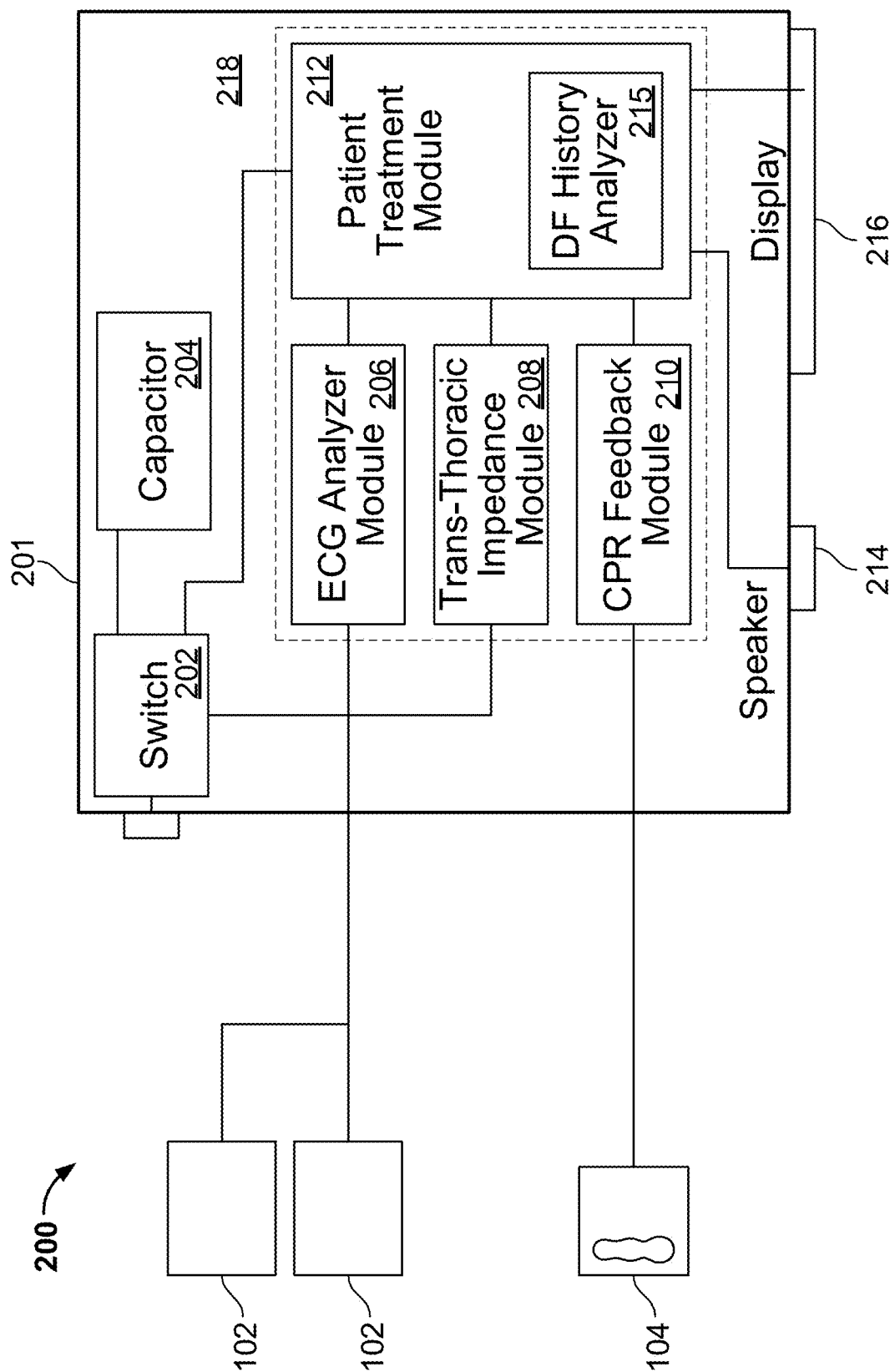
FIG. 2 is a schematic block diagram that shows a defibrillator with an electrode package and compression puck.

Referring now to FIG. 2, a schematic block diagram 200 shows an example defibrillator 201, along with the example electrode package 102 and compression puck 104, of FIG. 1A in more detail. In general, the defibrillator 201, and optionally one or more of the electrode package 102 and compression puck 104, defines an apparatus for administering care to a patient, subject, or individual (e.g., victim 122) who requires cardiac assistance.

The defibrillator 201 includes a switch 202 and at least one capacitor 204 for selectively supplying or applying a shock to a subject. The defibrillator 201 further includes an ECG analyzer module 206, a trans-thoracic impedance module 208, a CPR feedback module 210 that controls frequency and magnitude of chest compressions applied to a subject, a patient treatment (PT) module 212 (which includes a defibrillation history analyzer 215), a speaker 214, and a display 216. In this example, the ECG analyzer module 206, trans-thoracic impedance module 208, CPR feedback module 210, and patient treatment (PT) module 212 are grouped together as a logical module 218, which can be implemented by one or more computer processors. For example, respective elements of the logical module 218 can be implemented as: (i) a sequence of computer implemented instructions executing on at least one computer processor of the defibrillator 201; and (ii) interconnected logic or hardware modules within the defibrillator 201, as described in further detail below in connection with FIG. 9.

Similar to using individual AMSA values, multiple AMSA values can be used for making treatment determinations. For example, time series data of AMSA values, discernible trends of AMSA values, etc. can be used to define one or more conditions for which particular treatments, treatment adjustments, etc. should be employed. For example, AMSA time series data can be used for predicting the likelihood of successful defibrillation, indicating effective CPR, etc.

Similar to using AMSA values for estimating likelihood of defibrillation success, quantities calculated from AMSA values can be used for treatment determinations. Trending of AMSA values can be quantified (e.g., by differentiating portions of AMSA value time series), data can be normalized, weighting can be applied, various operations applied to the AMSA values, etc. to determine the likelihood of success or other quantities. In analyzing trends of AMSA values, the actual AMSA values (e.g., initial value) can factor in treatment determinations. For example, an AMSA value of 15.0 can be considered appropriate (e.g., large enough) to indicate a good likelihood of defibrillation success. Correspondingly, values near 15.0 can also be considered a good indication of a likelihood of defibrillation success. So even if a flat trend or a minimal positive trend is detected (e.g., AMSA values over time remain constant at 15.0 or only slightly increase to 16.0), the actual AMSA value (e.g., 15.0 or slightly larger) can govern and a good likelihood of a successful shock can be reported by the defibrillator. Alternatively for lower AMSA values, data trending can be heavily weighted. For example, due to CPR being applied a patient's AMSA value can significantly change from 5.0 to 12.0. Based upon such a positive trend in the AMSA values, a determination can report that the likelihood of shock success has increased and defibrillation can be administered.

To present the AMSA values, trend data, etc. (e.g., represented in the chart) to a rescuer or other individual, one or more techniques can be utilized. A graphical display incorporated into a defibrillator (such as the defibrillators described above and below) can present individual AMSA values, time averaged values, etc. in near real time to provide a numerical quantity of the patient's condition and the likelihood of defibrillation success (e.g., a value of "5.0 AMSA" can be considered as a value with a low likelihood of success while a value of "15.0 AMSA" can be considered as representing a relatively high likelihood of success). Graphical representations can also be employed to present the trending of the AMSA time series data. Positive trending values can be graphically represented in one color (e.g., blue) while relatively flat or negative trending AMSA values can be representing in another eye-catching color (e.g., red). Provided such image cues, rescuers can quickly determine if CPR efforts should continue (since a high likelihood of defibrillation success has not been reached), if CPR efforts should be adjusted (e.g., adjust to deeper and faster compressions based upon negatively trending AMSA values), if CPR can be halted for applying a defibrillation shock, etc. A threshold can be set for desired improvement in AMSA Similar to graphical representations, other types of representations (e.g., audio alerts, guidance messages, etc.) can be employed by a defibrillator (or other type of computing device) to indicate whether chest compressions are occurring (e.g., by using an accelerometer signal) and generate an output indicating that AMSA value should not be calculated or that the user interface should not provide a value for AMSA on the display, e.g., because the chest compressions may introduce artifacts into the calculation of AMSA values that interfere in calculating an accurate AMSA value. Accordingly, when chest compressions are occurring, the system may be configured not to display the current value of AMSA (e.g., due to signal artifacts), and when chest compressions are not detected, the system may then continuously calculate and display the current value of AMSA for the user to make a decision of what type of interventional therapy to provide (e.g., chest compressions, ventilations or defibrillation shock)

Similar to determining the likelihood of defibrillation success, AMSA values can be used to make other determinations such as classifying cardiac rhythm in VF or in asystole, a state of no cardiac electrical activity, as well as identifying treatments for patients classified in VF or in asystole. For example, based upon a threshold defined by an AMSA value, a patient can be identified as being in VF or in a state of no cardiac electrical activity referred to as asystole (colloquially known as flat line). Generally, CPR should be employed (or continued) if a patient is asystolic since shock treatment cannot improve the patient's condition and in some situations can worsen their condition. One study has demonstrated that asystole following defibrillation can produce a worse prognosis than primary asystole or pulseless electrical activity (PEA). By investigating the relationship between pre-shock AMSA values and the appearance of post-shock asystole, one or more determination techniques can be identified for either applying a shock or initiating (or continuing) a non-shock treatment such as administering CPR.

In one investigation, ECG recordings, sampled at 250 Hz, were digitized and data associated with initial shocks at a particular energy level (i.e., 120 Joules) was reviewed. Episodes of approximately two seconds (e.g., 2.05 seconds or 512 data points) that terminated a half second before a shock attempt were analyzed for AMSA values. As illustrated by a chart 100K shown in FIG. 1K, post shock rhythms were annotated as VF, asystole, PEA or tROSC (i.e., an organized rhythm present for a minimum of 32 seconds, started within 60 seconds after that shock, and having a rate of 40 beats per minute or larger). Data from a total of 543 patients with VF was investigated. From the data, for AMSA values of 3 mVHz or less, defibrillation resulted in 77.8% post-shock asystole and 22.2% of other non-perfusing rhythms (with no instances of tROSC). As illustrated in the figure, for AMSA values larger than 3.0 mVHz, asystole levels reported considerable decreases along with corresponding increases in post-shock VF, PEA and tROSC.

One or more conditions can be predefined for determining whether a defibrillation shock should be initiated for treatment. For example, an initial AMSA value can be determined from a patient's ECG, and then the measured AMSA value can be compared to a threshold value (e.g., an AMSA value of 3 mVHz). For measured values equivalent to or exceeding the threshold, defibrillation treatment can be deemed appropriate and initiated. For measured values below the threshold (e.g., below 3 mVHz), asystole (e.g., as predominate post-shock rhythm) can be considered probable and rhythm restoration by defibrillation can prove to be futile. As such, another recommended treatment such as CPR would be initiated or continued (if previously initiated).

Such determinations can be executed by one or multiple system components, for example, the AMSA analyzer 108 (shown in FIG. 1A) can utilize data from the ECG unit 106 (which can be part of a portable defibrillator) to determine if a predefined threshold (e.g., an AMSA value of 3 mVHz) has been met or exceeded. System equipment, modules, etc. described above and below can assist in determining and utilizing this information; for example, equipment can be used to deliver a defibrillating shock to a patient if a determined AMSA value (measure from the patient's ECG data) exceeds the predefined AMSA threshold. Along with different AMSA values (e.g., larger or smaller than 3 mVHz) being used for such determinations, other processing techniques can be employed. For example, multiple values (e.g., current and previous AMSA values) can be employed such that historical trends (hysteresis) factor into VF determinations and whether to use defibrillation or continue CPR.

In the example of FIG. 2, the electrode package 102 is connected to the switch 202 via port on the defibrillator 201 so that different packages can be connected at different times. The electrode package 102 can also be connected through the port to ECG analyzer module 206, and transthoracic impedance module 208.

The compression puck 104 is connected, in this example, to the CPR feedback module 210. In one embodiment, the ECG analyzer module 206 is a component that receives an ECG (e.g., ECG signal 132). Similarly, the trans-thoracic impedance module 208 is a component that receives trans-thoracic impedance (e.g., trans-thoracic impedance signal 110). Other embodiments are also possible.

The patient treatment module 212 is configured to receive an input from each one of the ECG analyzer module 206, trans-thoracic impedance module 208, and CPR feedback module 210. The patient treatment module 212 uses inputs as received from at least the ECG analyzer module 206 and trans-thoracic impedance module 208 to predict whether a defibrillation event can likely terminate an arrhythmic episode. For example, ECG data can be used both to determine AMSA values for a patient, and also determine whether shocks are effective or not so that such information can be saved and used to identify likelihoods that subsequent shocks can be effective). In this manner, the patient treatment module 212 uses information derived from both an ECG signal (both for AMSA and for adjusting the AMSA value) and transthoracic impedance measurement to provide a determination of a likelihood of success for delivering a defibrillating shock to a subject.

The patient treatment module 212 is further configured to provide an input to each one of the speaker 214, display 216, and switch 202. In general, input provided to the speaker 214 and a display 216 corresponds to either a success indication or a failure indication regarding the likelihood of success for delivering a shock to the subject. In one embodiment, the difference between a success indication and a failure indication is binary and based on a threshold. For example, a success indication can be relayed to the display 216 when the chances corresponding to a successful defibrillation event is greater than 75%. In this example, the value "75%" can be rendered on the display 216 indicating a positive likelihood of success. When a positive likelihood of success is indicated, the patient treatment module 212 enables the switch 202 such that a shock can be delivered to a subject.

The patient treatment module 212 can also implement an ECG analyzer for generating an indication of heart rate for the patent, for generating an indication of heart rate variability for the patent, an indication of ECG amplitude for the patent, and/or an indication of a first or second derivative of ECG amplitude for the patient. The indication of ECG amplitude can include an RMS measurement, measured peak-to-peak, peak-to-trough, or an average of peak-to-peak or peak-to-trough over a specified interval. Such indications obtained by the ECG analyzer can be provided to compute an AMSA value for the patient and/or can be used in combination with a computed AMSA value so as to generate some derivative indication regarding whether a subsequent shock is likely or unlikely to be effective (and the degree, e.g., along a percentage scale, of the likelihood).

In another embodiment, likelihood of a successful defibrillation event can be classified into one of many possible groups such as, for example, low, medium, and high likelihood of success. With a "low" likelihood of success (e.g., corresponding to a successful defibrillation event is less than 50%), the patient treatment module 212 disables the switch 202 such that a shock cannot be delivered to a subject. With a "medium" likelihood of success (e.g., corresponding to a successful defibrillation event is greater than 50% but less than 75%), the patient treatment module 212 enables the switch 202 such that a shock can be delivered to a subject, but also renders a warning on the display 216 that the likelihood of success is questionable. With a "high" likelihood of success (e.g., corresponding to a successful defibrillation event is greater than or equal to 75%), the patient treatment module 212 enables the switch 202 such that a shock can be delivered to a subject, and also renders a cue on the display 216 indicating that the likelihood of success is very good. Still other embodiments are possible.

Thus, the system 200 can provide, in a portable electric device (e.g., a battery-operated device) the capability to analyze a number of inputs and to identify a variety of factors from those inputs, where the factors can then be combined to provide a flexible, intelligent determination of likely success.

Figure 3A:
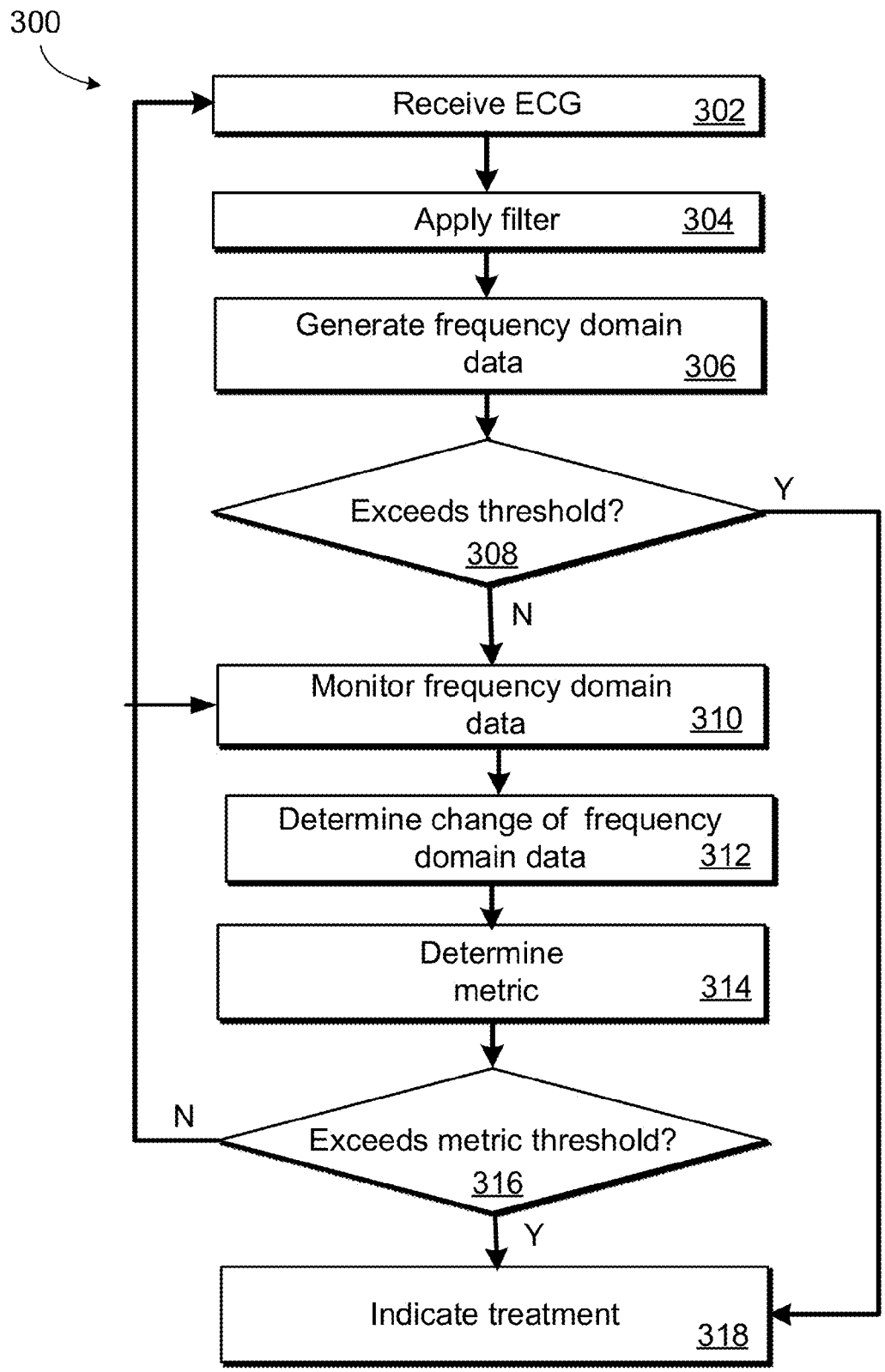
FIG. 3A is a flow chart of an example process for providing guidance to a rescuer.

Referring to FIG. 3A an example flow chart of a process 300 for administering care to a patient requiring cardiac assistance is illustrated. In implementations, the method 300 is implemented by the example defibrillators described herein, for example, in connection with FIGS. 1B and 2. However, other embodiments are possible.

At a step 302, an ECG signal (e.g., ECG signal 132) is monitored. In general, an individual receiving cardiac care includes the patient at any time during a cardiac event, including whether or not patient is receiving active care (e.g., chest compressions).

At a step 304, an optional filter can be applied. For example, a high-pass filter with a desired cutoff frequency (preferably but not limited to be 0.5 Hz) can be applied to remove the baseline drift. At a step 306, a Fast Fourier transform (FFT) is applied to the filtered ECG signal to generate frequency-domain data. The spectral shape can be quantified using a preferred method and a first frequency-domain value can be generated.

At a step 308, a first frequency-domain value is compared to a threshold. In some implementations, the frequency-domain value is directly compared to a predetermined frequency-domain threshold or a frequency-domain value can be converted to a probability of defibrillation success, which is compared to a predetermined defibrillation success threshold. If the first frequency-domain value exceeds the predetermined frequency-domain threshold or if the associated probability of success exceeds the predetermined defibrillation success threshold, the process can continue with step 318 to indicate a treatment (e.g., defibrillating shock and/or other therapeutic intervention). If the first frequency-domain value is below the predetermined frequency-domain threshold, the process continues to step 310.

At step 310, a frequency-domain value is continuously monitored over a first evaluation time period. In some implementations, the first evaluation time period can correspond to a pause in chest compressions and/or can be a preset time period (e.g., 1 minute). At step 312, a second frequency-domain value corresponding to a change in frequency-domain can be determined. In some implementations, the process includes an automatic identification of a steady change in frequency-domain value using a statistical analysis of the frequency-domain values recorded during the first evaluation time period. In some implementations, the change in frequency-domain can be provided as a difference between two frequency-domain values determined during the first evaluation time period. It can be appreciated that the change in frequency-domain can be determined via any suitable method familiar to those of skill in the art. Such values can be determined at any given point (e.g., beginning, middle, or end) of the first evaluation time period. In some implementations, the change in frequency-domain can be defined as a frequency-domain change rate (e.g., difference between two frequency-domain values relative to the first evaluation time period). The two frequency-domain values used to determine frequency-domain change can be absolute, mean or median frequency-domain values. One of the two frequency-domain values can be first frequency-domain value determined at step 306 or a different frequency-domain value determined at a time later than the first time, which corresponds to the beginning of the first evaluation time period.

In some implementations, the frequency-domain data can be subject to a regression analysis. For example, such a regression analysis can involve a statistical model that inputs a first frequency-based value (e.g., AMSA) based on a time-frequency transformation taken over a first evaluation period, and further inputs a second frequency-based value (e.g., overall change in AMSA) that represents a trend based on one or more additional time-frequency transformations taken over a second evaluation period. The first evaluation period can be a period around the initiation of ECG recording (e.g., including initial AMSA) and the second evaluation period can be any time interval subsequent to the first evaluation period, expanding over a duration of few seconds. The second evaluation period can also be continuously updated, to follow a real-time recording of the ECG (e.g., including the most recently acquired and determined data). The output of the regression analysis can be a probability of therapeutic (e.g., defibrillation or other interventional therapy) success. Regression analysis can be used to determine weights that produce improved correlation between the weighted sum and the probability of successful defibrillation (or between the weighted sum and the presence of a physiological condition). In various embodiments, the model for simple linear regression is:

$$Y=a+b*X$$

where Y is the dependent variable, X is the independent variable, and a and b are the regression parameters (the intercept and the slope of the line of best fit).

As noted herein, various forms of statistical estimation in accordance with the present disclosure can take at least two inputs for a statistical model, a frequency-based parameter and a trend of the frequency-based parameter, where the output of the statistical model is a probability of therapeutic success. An example of a suitable statistical model that can be used with embodiments described herein is a multiple linear regression, as generally described below.

The model for multiple linear regression is:

$$Y=a+b_1*X_1+b_2*X_2+ \ldots +b_i*X_i$$

The coefficients, $b_i$, for each input variable, $X_i$, are calculated using statistical methods such as the general linear model to provide a best estimate of the probability of defibrillation success, Y. The variable, Y, can also represent the probability of success of any therapeutic intervention other than defibrillation, for instance chest compressions, ventilations or a metabolic treatment such as epinephrine or aspartate. The variable, Y, can also represent the probability that the patient is in a particular physiological state. The general linear model (GLM) can estimate and test any univariate or multivariate general linear model, including those for multiple regression, analysis of variance or covariance, and other procedures such as discriminant analysis and principal components. With the general linear model, randomized block designs, incomplete block designs, fractional factorial designs, Latin square designs, split plot designs, crossover designs, nesting, can be explored. The model is:

$$Y=XB+e,$$

where Y is a vector or matrix of dependent variables, X is a vector or matrix of independent variables, B is a vector or matrix of regression coefficients, and e is a vector or matrix of random errors.

In multivariate models, Y is a matrix of continuous measures. The X matrix can be either continuous or categorical dummy variables, according to the type of model. For discriminant analysis, X is a matrix of dummy variables, as in analysis of variance. For principal components analysis, X is a constant (e.g., a single column of 1s). For canonical correlation, X is usually a matrix of continuous right-hand variables (and Y is the matrix of left-hand variables).

For some multivariate models, it can be easier to use ANOVA, which can handle models with multiple dependent variables and zero, one, or more categorical independent variables (that is, only the constant is present in the former). ANOVA automatically generates interaction terms for the design factor.

After the parameters of a model have been estimated, they can be tested by any general linear hypothesis of the following form:

$$ABC'=D,$$

where A is a matrix of linear weights on coefficients across the independent variables (the rows of B), C is a matrix of linear weights on the coefficients across dependent variables (the columns of B), B is the matrix of regression coefficients or effects, and D is a null hypothesis matrix (usually a null matrix).

The coefficients, $b_i$, are calculated using ECG or other measured physiological data collected from a statistically varied population of samples to provide a robust database for accurate model generation. Preferably, the resuscitation event is decomposed into multiple therapy states, e.g., arrival at patient's side, pre-shock, post-shock, post-vasopressor, etc., with separate sets of coefficients generated for each therapy state. The state of therapy, e.g., resuscitation, is determined and stored by the defibrillator. For instance when the unit is first turned on and prior to the first shock, the resuscitation is considered in the "arrival at patient's side" (APS) state; if CPR is detected by the defibrillator, it shifts to the "CPR first, no shock state"; after defibrillation, the state machine shifts to the "first shock" state. Subsequent shocks cause the state machine to transition to states for each defibrillation, e.g. "second shock", etc. Coefficients, $b_i$, are calculated for each state and stored on the defibrillator, and used to calculate the most accurate predictor, Y, of therapeutic outcome (or current physiologic state). Therapeutic outcome, Y, can be scaled so as to provide a value from either zero to one or zero to one-hundred, representing on a scale that is understandable to the operator that it is a probability; the value of Y can also be unscaled.

Regression can also be performed using the logistic function:

$$Y = 100\left[1 - \frac{1}{1 + e^{\beta_o + \sum \beta_i x_i}}\right]$$

In some examples, such as for a large data set, multivariate logistic regression can be expressed as following:

$$\pi(X) = \frac{e^{\beta_0+\beta_1 X_1+\beta_2 X_2+\ldots+\beta_p X_p}}{1 + e^{\beta_0+\beta_1 X_1+\beta_2 X_2+\ldots+\beta_p X_p}}$$

The logistic transformation can be derived as following:

$$logit[\pi(X)] = \ln\left[\frac{\pi(X)}{1-\pi(X)}\right]$$

$$= \ln\left[\frac{\frac{e^{\beta_0+\beta_1 X_1+\beta_2 X_2+\ldots+\beta_p X_p}}{1+e^{\beta_0+\beta_1 X_1+\beta_2 X_2+\ldots+\beta_p X_p}}}{1-\frac{e^{\beta_0+\beta_1 X_1+\beta_2 X_2+\ldots+\beta_p X_p}}{1+e^{\beta_0+\beta_1 X_1+\beta_2 X_2+\ldots+\beta_p X_p}}}\right]$$

$$= \ln\left[\frac{\frac{e^{\beta_0+\beta_1 X_1+\beta_2 X_2+\ldots+\beta_p X_p}}{1+e^{\beta_0+\beta_1 X_1+\beta_2 X_2+\ldots+\beta_p X_p}}}{\frac{1}{1+e^{\beta_0+\beta_1 X_1+\beta_2 X_2+\ldots+\beta_p X_p}}}\right]$$

$$= \ln[e^{\beta_0+\beta_1 X_1+\beta_2 X_2+\ldots+\beta_p X_p}]$$

$$= \beta_0 + \beta_1 X_1 + \beta_2 X_2 + \ldots + \beta_p X_p$$

Where $X_1$=$AMSA_1$ and $X_2$=$\Delta AMSA$ and the coefficients are:

$\beta_0$=−5.55612
$\beta_1$=0.3742736
$\beta_2$=0.6358645

At step 314, a metric of defibrillation success can be determined. In some implementations, the metric can be determined using the method described with reference to FIG. 1T. The logistic model is useful in estimating the probability of therapeutic success where the outcome is binomial and dependent on at least one predictive factor, such that certain values of the predictive factor, can be associated with successful defibrillation and other times with unsuccessful defibrillations. The logistic curve is a non-linear transformation that converts the measured predictive factor into a value approximating a probability of success. It provides a reasonable, mathematically tractable approach to minimizing the false negatives and false positives.

A threshold can be chosen to optimize both the false negatives (FN) and false positives (FP) to provide the best sensitivity and specificity for the prediction:

Sensitivity=True Positives (*TP*)/(*TP+FN*)

Specificity=*TP*/(*TP+FN*)

Positive Predictive Value (*PPV*)=*TP*/(*TP+FP*)

Negative Predictive Value (*NPV*)=*TN*/(*TN+FN*)

In some implementations, the metric is provided as a numeric value or as percentage of probability of defibrillation success. Continuing with the provided example for large data sets, based on the multivariate logistic regression, the probability of shock success ($Pr_{ss}$) as a function of $AMSA_1$ and $\Delta AMSA$ can be determined as:

$Pr_{ss}$=1/(1+exp(5.55612−0.3742736*$AMSA_1$−0.6358645*$\Delta AMSA$))).

At step 316, the metric is compared to a second predetermined threshold. If the metric is below the predetermined threshold the process can be repeated from step 312 or 310. If the metric exceeds the predetermined threshold, the process 300 can continue with step 318 to indicate treatment.

In some implementations, the operator can be provided with the probability of defibrillation success indication or with an indication of suggested treatment. For example, the operator can be shown a percentage number, or an intuitive display such as a gauge, bar graph, color indication, etc., that indicates a likelihood in percent that the shock can be successful. Alternatively, or in addition, the operator can be shown a less granular level of an indication, such as a value of "excellent," "good," and "poor" to indicate to the operator what the likelihood of successful defibrillation is. Given this information, the operator is then faced with a decision of whether to administer one or more defibrillation shocks.

In some implementations, a trigger mechanism is enabled on the defibrillator, as discussed above. The trigger mechanism can be enabled whenever a shockable rhythm is observed for a patient. In other circumstances, the enabling can occur only when the combined indication discussed above exceeds a threshold value for indicating that a shock can be successful in defibrillating the patient. For a hybrid defibrillator that is capable of manual and AED modes, the trigger mechanism can operate different depending on what mode the defibrillator is in.

An arrow is shown returning to the top of the process to indicate that the process here is in ways continuous and in ways repeated. In particular, ECG signals are gathered continuously, as are other types of data. And the process repeatedly tries to identify whether a shock can or should be provided, and the order and timing of the steps in that cycling can be dictated by standards as adjusted by a medical director or other appropriate individual responsible for the deployed defibrillator. Thus, for instance, the entire process can be repeated, some portions can be repeated more frequently than others, and some portions can be performed once, while others are repeated.

Figure 3B:
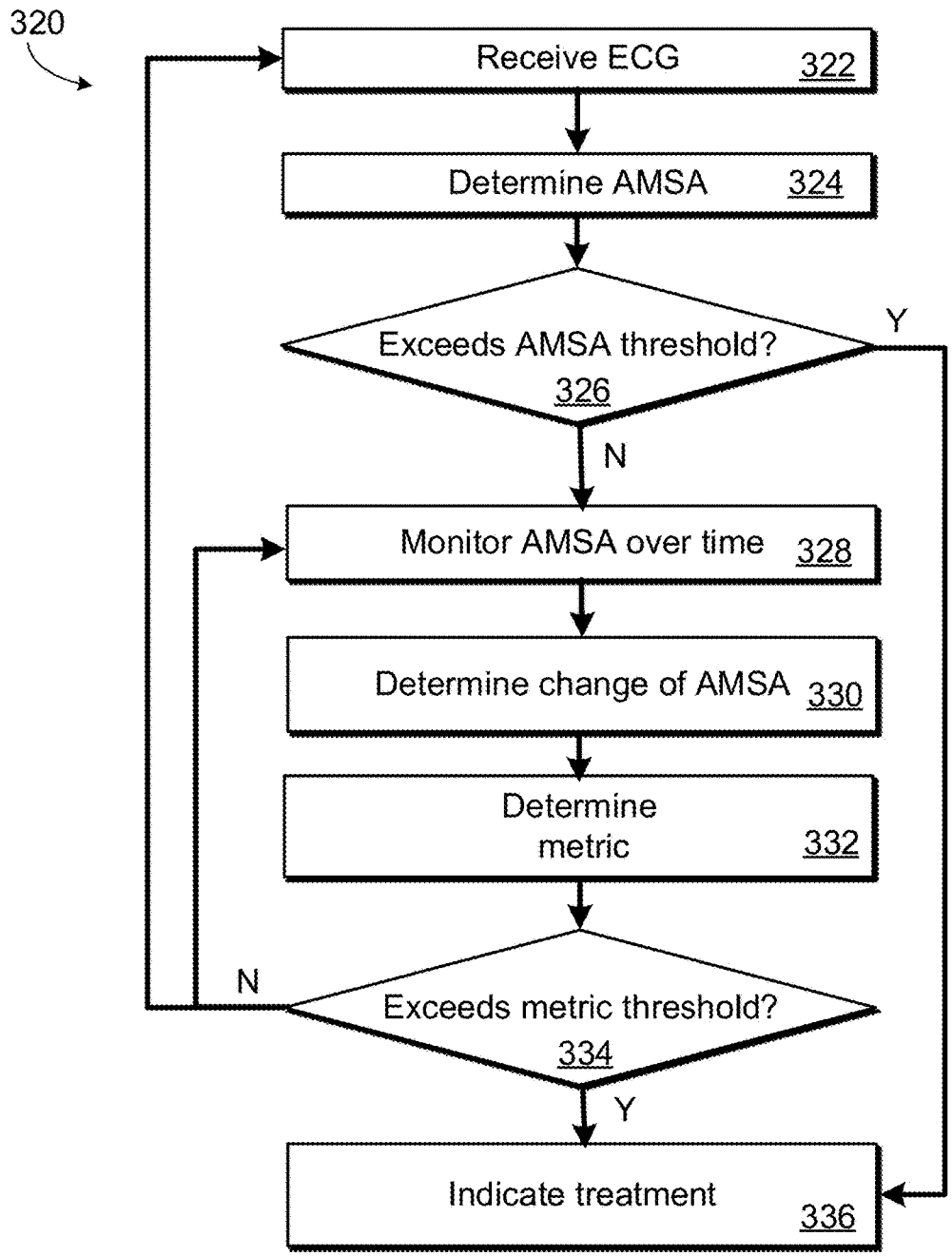
FIG. 3B is a flow chart of another example process for providing guidance to a rescuer.

Referring now to FIG. 3B, another example method 320 is shown for administering care to a patient requiring cardiac assistance. In some implementations, the method 320 is implemented by the example defibrillators described herein, for example, in connection with FIGS. 1B and 2. However, other embodiments are possible.

At a step 322, an ECG signal (e.g., ECG signal 132) is recorded and monitored. In general, continuous ECG monitoring is standard procedure for a patient receiving cardiac care, whether or not the patient is receiving active care (e.g., chest compressions).

At a step 324, a first AMSA value corresponding to a first time point is calculated from the ECG signal, monitored at step 322. The first AMSA value can be determined by integrating the Fourier transform (e.g., FFT) of the ECG signal over a finite frequency range. Example frequency content of an arrhythmic ECG signal generally ranges between about 1 Hz to about 40 Hz, with amplitude of about 50 mV or less. An example of an AMSA value calculated from such a signal ranges between about 5 mVHz to about 20 mVHz.

The AMSA value can be determined from a moving window that moves in time through the incoming ECG data as it arrives (e.g., the raw ECG data can be cached for a period at least as long as the window), where the window can be about one second wide (or more), and it can be measured multiple times each second so that there are overlapping windows. The window can also have a tapered (rather than rectangular) window function so as to improve the accuracy of the AMSA value in predicting defibrillation success. The coefficients for the window can be selected to maximize the accuracy of the calculation. In addition, multiple different AMSA values can be determined (e.g., with different window size, type, and/or coefficients). In some implementations, a single absolute value of the most-accurate AMSA estimate can be provided as output or a composite value can be generated from each of the determined AMSA values.

Additionally, the window size, type, and coefficients can change over time to allow a system to dynamically adjust to a particular VF event. For example, using determinations about the phase in which a VF event is, a system can change such parameters to switch to a window that is determined to better predict defibrillation success. Alternatively, a blend of window techniques can be used and the blend can change over time, while a composite prediction score is determined from the blended techniques.

For example, a system could shift from a symmetric window to an asymmetric window just prior to the end of a CPR interval as it gets closer to the time of a shock. The system can be continuously executing a noise detection process, and if sections of the data in the window are found to have ECG with anomalously high amounts of higher frequency noise compared to ECG in adjacent sections, then those portions of the window can be attenuated via adjusting the window characteristics. If the burst of noise occurs in the middle of the window, then the window function can be composed of two adjacent Tukey or other windows where the null of the superimposed windows is centered at the occurrence of the noise burst. Thus, various dynamic changes can be made to the window as the process occurs so as to adjust to particular activities for a patient.

At a step 326, a first AMSA value is compared to a threshold. In some implementations, the AMSA value is directly compared to a predetermined AMSA threshold or the AMSA value can be converted to a probability of defibrillation success (e.g., by using the methods described with reference to FIG. 1N), which is compared to a predetermined defibrillation success threshold. An example predetermined AMSA threshold can be 12 mVHz and an example probability of defibrillation success threshold can be 50%. If the first AMSA value exceeds the predetermined AMSA threshold or if the associated probability of success exceeds the predetermined defibrillation success threshold, the process can continue with step 336 to indicate a treatment (e.g., defibrillating shock and/or other therapeutic intervention). If the first AMSA value is below the predetermined AMSA threshold, the process continues to step 328.

At step 328, AMSA value is continuously or intermittently monitored over a first time period (e.g., first evaluation period). In some implementations, the first time period can correspond to a chest compression break and/or can be a preset time period (e.g., 1 minute). At step 330, a second AMSA value corresponding to a change in AMSA can be determined. In some implementations, the process includes an automatic identification of a steady change in AMSA value (e.g., median AMSA values are monotonically increasing) using a statistical analysis of the AMSA values recorded during the first time period (e.g., a regression analysis as described with reference to FIG. 3A). In some implementations, the change in AMSA can be defined as a difference between two AMSA values determined during the first time period. In some implementations, the change in AMSA can be defined as an AMSA change rate (e.g., difference between two AMSA values relative to time). The two AMSA values used to determine AMSA change can be absolute values, mean values or median values extracted from the array of AMSA values derived from the frequency domain data or from the output of the regression analysis. One of the two AMSA values can be first AMSA value determined at step 324 or a different AMSA value determined at a time later than the first time, which can correspond to the beginning of the first time period.

At step 332, a metric of defibrillation success can be determined. The metric can be an indicator of myocardial viability. In some implementations, the metric can be determined using the method described with reference to FIGS. 1Q and 1S. In some implementations, the metric is provided as a numeric value or as percentage of probability of defibrillation success. At step 334, the metric is compared to a second predetermined threshold. If the metric is below the predetermined threshold the process can be repeated from step 322 or 328. If the metric exceeds the predetermined threshold, the process 320 can continue with step 336 to indicate treatment.

Similar to that discussed above, in some implementations, the operator can be provided with the probability of defibrillation success indication or with an indication of suggested treatment. For example, the operator can be shown a percentage number that indicates a likelihood in percent that the shock can be successful. Alternatively, or in addition, the operator can be shown a less granular level of an indication, such as a value of "excellent," "good," and "poor" to indicate to the operator what the likelihood of successful defibrillation is.

In some implementations, a trigger mechanism is enabled on the defibrillator, as discussed above. The trigger mechanism can be enabled whenever a shockable rhythm is observed for a patient. In other circumstances, the enabling can occur only when the combined indication discussed above exceeds a threshold value for indicating that a shock can be successful in defibrillating the patient. For a hybrid defibrillator that is capable of manual and AED modes, the trigger mechanism can operate different depending on what mode the defibrillator is in.

An arrow is shown returning to the top of the process to indicate that at least parts of the process can be continuous performed during cardiac patient care and at least parts of the process can be repeated. In particular, ECG signals are gathered continuously, as are other types of data. Process 320 can be implemented as a loop function designed to repeatedly identify whether a shock can or should be provided. The order and the timing of the steps of the process 320 can be dictated by different medical standards or they can be adjusted by a medical director or other appropriate individual responsible for the deployed defibrillator. Thus, for instance, the entire process 320 can be repeated, some portions of the process can be repeated more frequently than others, and some portions of the process can be performed once, while others are repeated.

Figure 4A:
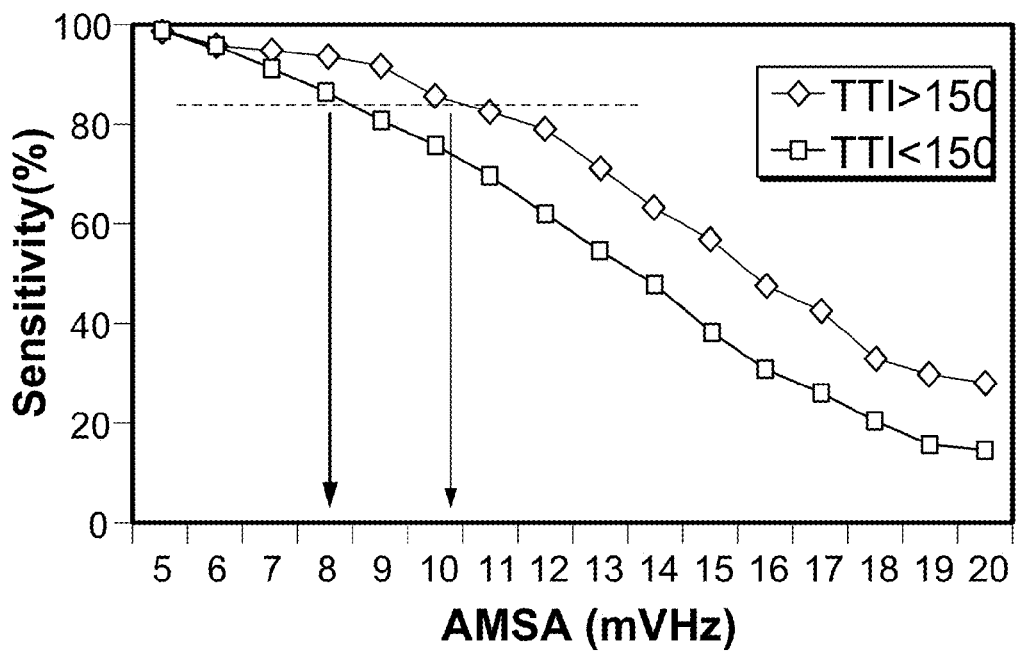
FIGS. 4A and 4B are graphs showing relationships between patient outcome and AMSA threshold values for groups of patients having different trans-thoracic impedance values.

FIG. 4A shows a plot of positive predictive value (%) versus AMSA threshold (mVHz) for a first set of subjects having a trans-thoracic impedance measured greater than 150 ohms and a second set of subjects having a trans-thoracic impedance measured less than 150 ohms. As shown by the comparative data, the first set of subjects generally has a greater positive predictive value for a given AMSA threshold. In both cases, positive predictive value generally increases with increasing AMSA threshold. Thus, an indication of success for a patient having a low impedance can be provided when the AMSA value is lower, than for a comparable AMSA value from a high impedance patient. Or, where a percentage likelihood of success is shown, the displayed percentage for a particular AMSA value can be higher for a low impedance patient as compared to a high impedance patient—at least with the range of AMSA values from 5-20 mVHz.

Figure 4B:
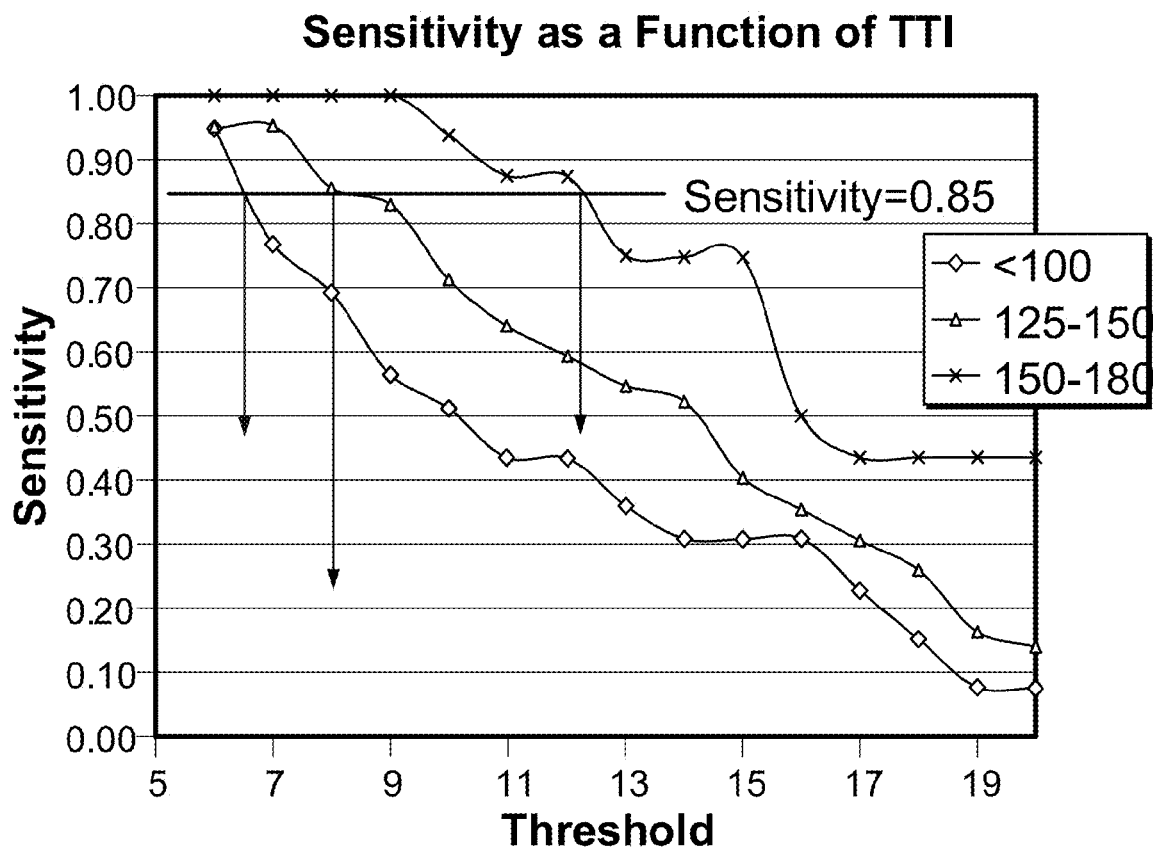

FIG. 4B shows a plot of sensitivity (unit-less) versus AMSA threshold (mVHz) for a first set of subjects having a trans-thoracic impedance measured less than 100 ohms, a second set of subjects having a trans-thoracic impedance measured between 125 ohms and 150 ohms, and a third set of subjects having a trans-thoracic impedance measured between 150 ohms and 180 ohms. As shown by the comparative data, AMSA threshold generally increases, for a given specificity, with increasing trans-thoracic impedance.

Figure 5A:
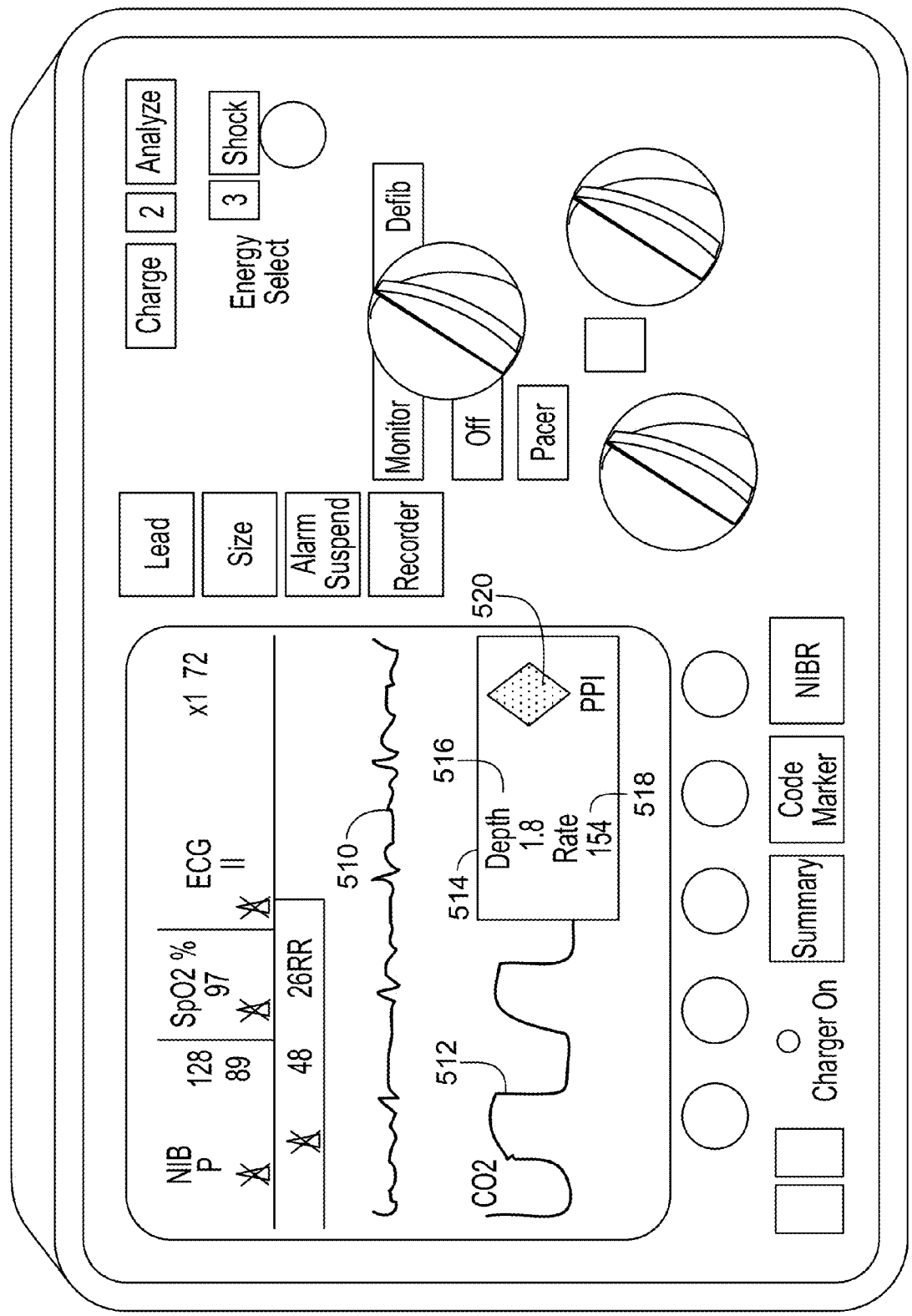
FIGS. 5A and 5B illustrate a defibrillator showing examples of information that can be displayed to a rescuer.

FIG. 5A shows a defibrillator showing examples of information that can be displayed to a rescuer. In the figure, a defibrillation device 500 with a display portion 502 provides information about patient status and CPR administration quality during the use of the defibrillator device. As shown on display 502, during the administration of chest compressions, the device 500 displays information about the chest compressions in box 514 on the same display as is displayed a filtered ECG waveform 510 and a $CO_2$ waveform 512 (alternatively, an $SpO_2$ waveform can be displayed).

During chest compressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled "Method and Apparatus for Enhancement of Chest Compressions During Chest Compressions," the contents of which are hereby incorporated by reference in their entirety.

Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

The CPR information in box 514 is automatically displayed when compressions are detected by a defibrillator. The information about the chest compressions that is displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 514 also includes a perfusion performance indicator (PPI) 520. The PPI 520 is a shape (e.g., a diamond) with the amount of fill that is in the shape differing over time to provide feedback about both the rate and depth of the compressions. When CPR is being performed adequately, for example, at a rate of about 100 compressions per minute (CPM) with the depth of each compression greater than 1.5 inches, the entire indicator can be filled. As the rate and/or depth decreases below acceptable limits, the amount of fill lessens. The PPI 520 provides a visual indication of the quality of the CPR such that the rescuer can aim to keep the PPI 520 completely filled.

As shown in display 500, the filtered ECG waveform 510 is a full-length waveform that fills the entire span of the display device, while the second waveform (e.g., the $CO_2$ waveform 512) is a partial-length waveform and fills only a portion of the display. A portion of the display beside the second waveform provides the CPR information in box 514. For example, the display splits the horizontal area for the second waveform in half, displaying waveform 512 on left, and CPR information on the right in box 514.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 521 regarding "release" in performing chest compression. Specifically, a fatigued rescuer can begin leaning forward on the chest of a victim and not release pressure on the sternum of the victim at the top of each compression. This can reduce the perfusion and circulation accomplished by the chest compressions. The reminder 521 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication can be accompanied by additional visual feedback near the rescuer's hands, and by a spoken or tonal audible feedback, including a sound that differs sufficiently from other audible feedback so that the rescuer can understand that release (or more specifically, lack of release) is the target of the feedback.

Figure 5B:
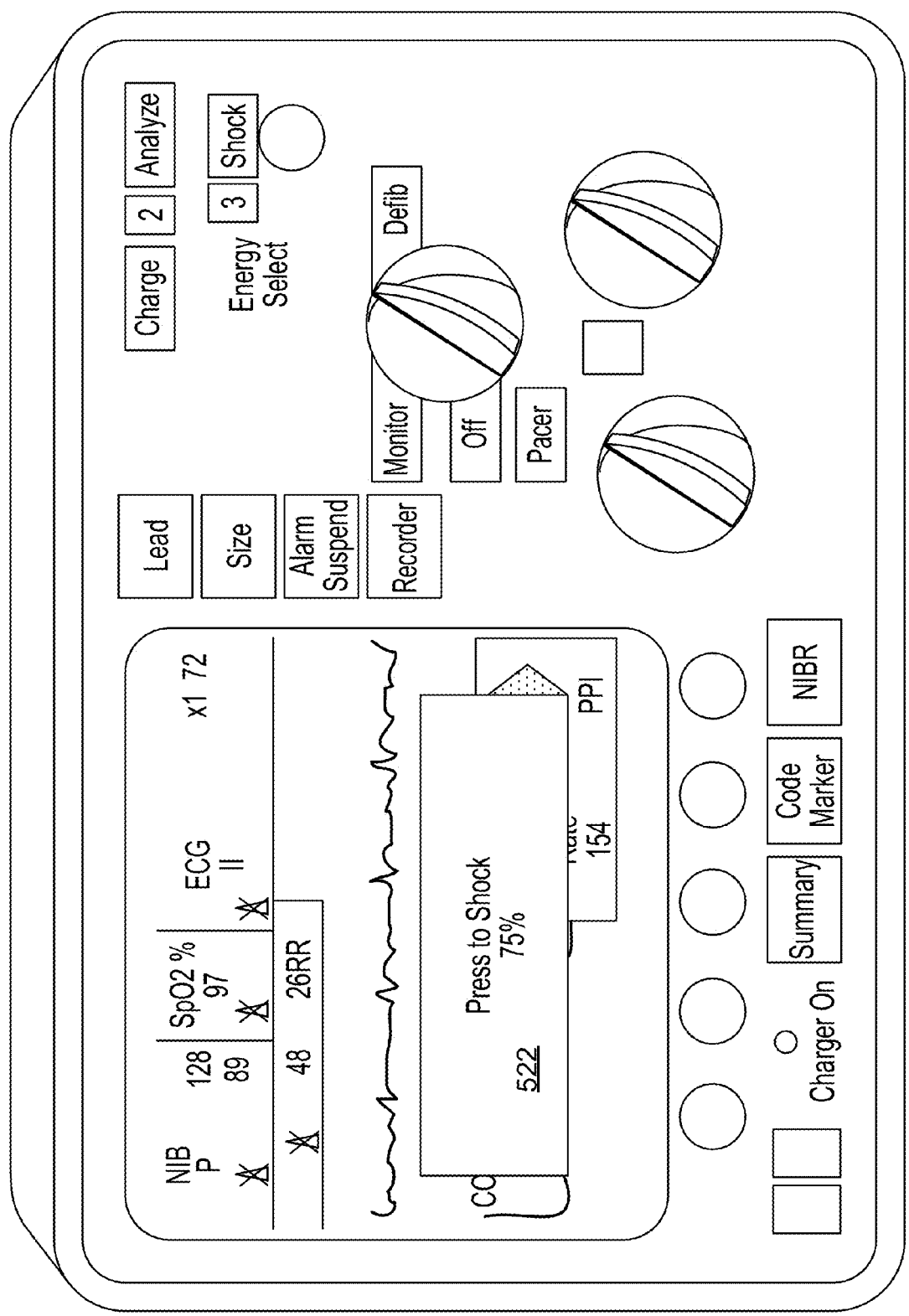

FIG. 5B shows the same defibrillator, but with an indicator box 522 now shown across the bottom half of the display and over the top of information that was previously displayed to display a success indication of "75%." Similar to the display 216 as described above, the indicator box 522 can generally convey a success indication or a failure indication regarding the likelihood of success for delivering a shock to a subject. The success indication can be generated using any combination of the techniques discussed above, including AMSA values, measures of prior effectiveness or ineffectiveness of prior defibrillating shocks, and trans-thoracic impedance.

In some implementations, one or more of the inputs used for determining a likelihood that a future shock can be successful, cannot be available. For example, at times it cannot be possible to calculate AMSA accurately when CPR compressions are occurring. Or perhaps a system is receiving values for trans-thoracic impedance that are not possible, which would indicate a problem with the sensors measuring such impedance or other similar problems. In such situations, the score that is generated to indicate a likelihood of success can be switched to a score that depends only on n−1 inputs (where n is the optimal number of inputs, and n−1 represents the removal of one of the inputs). Thus, the system can be adaptive to problems with particular ones of the inputs that indicate a likelihood of success, yet the system can still determine a likelihood of success that is as accurate as possible given the inputs that are available.

In the example shown, the success indication is textual; however the success indication (and/or failure indication)

can generally be implemented as any type of perceptible feedback. For example, tone, color, and/or other perceptible visual effects can be rendered or otherwise displayed to a user via the indicator box. For example, the characters "75%" can be highlighted or otherwise distinguished in a bold color, and the phrase "Press to Shock" can blink at least intermittently to convey a sense of urgency with respect to a pending shock. Other embodiments are possible.

Figure 6A:
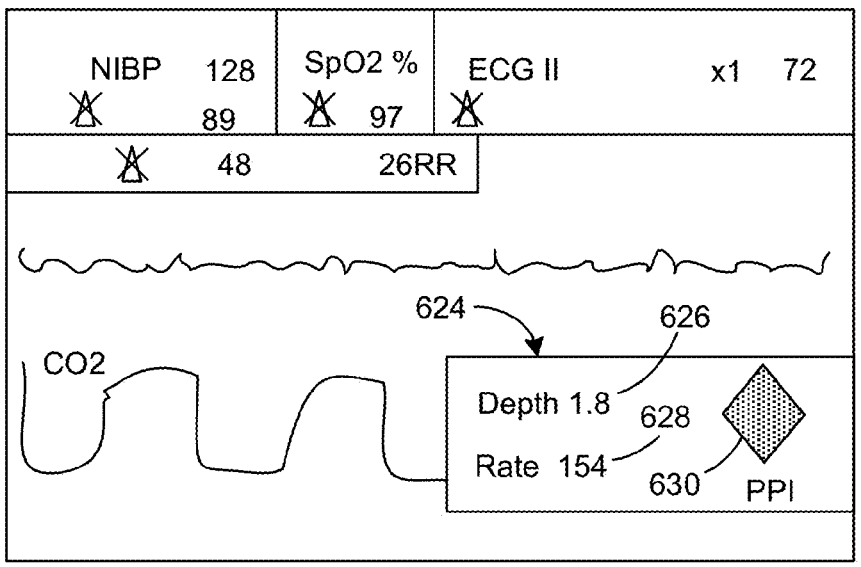
FIGS. 6A-6C show screenshots of a defibrillator display that provides feedback concerning chest compressions performed on a victim.
Figure 6B:
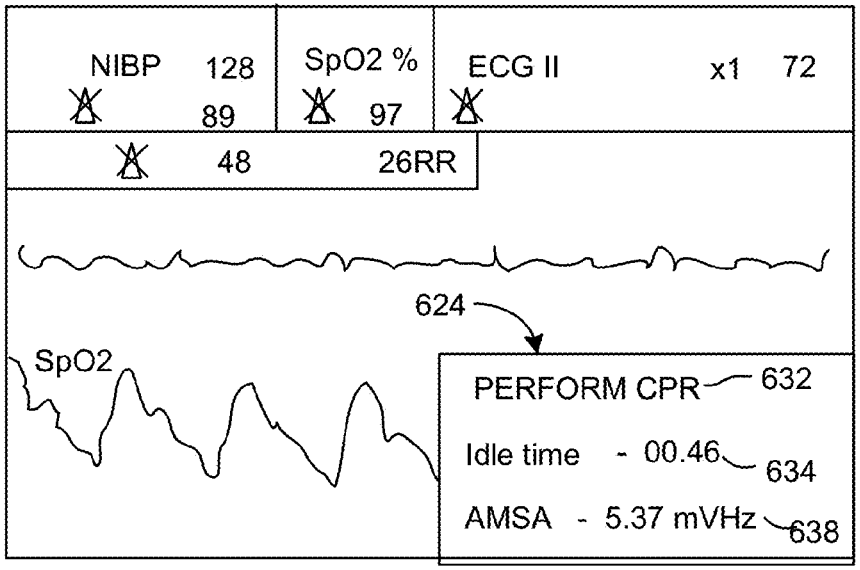
Figure 6C:
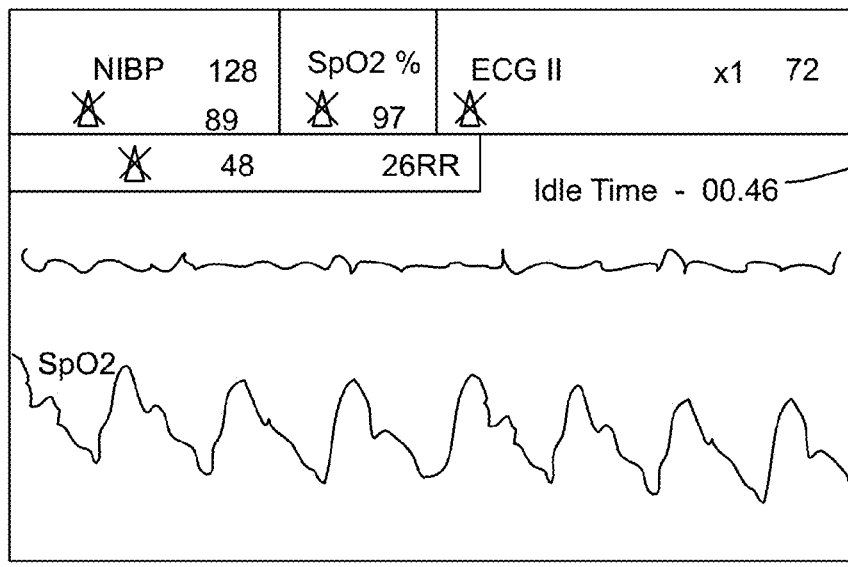

FIGS. 6A-6C show example screens that can be displayed to a rescuer on a defibrillator. Each of the displays can be supplemented with an indicator-like box 522 in FIG. 5B when the defibrillator makes a determination as to the likelihood of success for delivering a shock to a subject.

FIG. 6A shows exemplary information displayed during the administration of CPR chest compressions, while FIGS. 6B and 6C show exemplary information displayed when CPR chest compressions are not being sensed by the defibrillator. The defibrillator automatically switches the information presented based on whether chest compressions are detected. An exemplary modification of the information presented on the display can include automatically switching one or more waveforms that the defibrillator displays. In one example, the type of measurement displayed can be modified based on the presence or absence of chest compressions. For example, $CO_2$ or depth of chest compressions can be displayed (e.g., a $CO_2$ waveform 620 is displayed in FIG. 6A) during CPR administration, and upon detection of the cessation of chest compressions, the waveform can be switched to display AMSA and a $SpO_2$ or pulse waveform (e.g., a $SpO_2$ waveform 622 is displayed in FIG. 6B).

Another exemplary modification of the information presented on the display can include automatically adding/removing AMSA and CPR information from the display upon detection of the presence or absence of chest compressions. As shown in FIG. 6A, when chest compressions are detected, a portion 624 of the display includes information about the CPR such as depth 626, rate 628, and PPI 630. As shown in FIG. 6B, when CPR is halted and the system detects the absence of CPR chest compressions, the defibrillator can calculate AMSA values 638 and change the CPR information in the portion 624 of the display, to include an indication 632 that the rescuer should resume CPR, an indication 634 of the idle time since chest compressions were last detected and determined AMSA values 638. In a similar manner, when the defibrillator determines that rescuers should change, the label 632 can change to a message such as "Change Who is Administering CPR." In other examples, as shown in FIG. 6C, when CPR is halted, the defibrillation device can remove the portion of the display 624 previously showing CPR data and can display a full view of the second waveform. Additionally, information about the idle time 636 can be presented on another portion of the display.

Figure 7A:
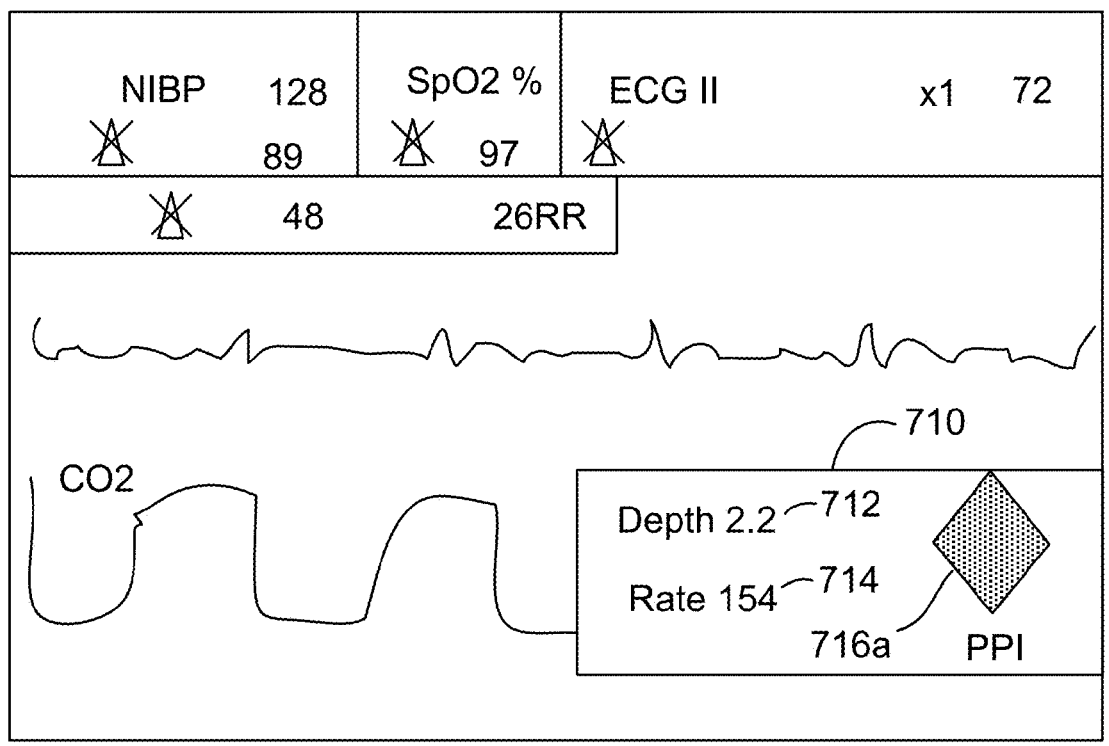
FIGS. 7A and 7B show screenshots providing feedback regarding a perfusion index created from chest compressions.
Figure 7B:
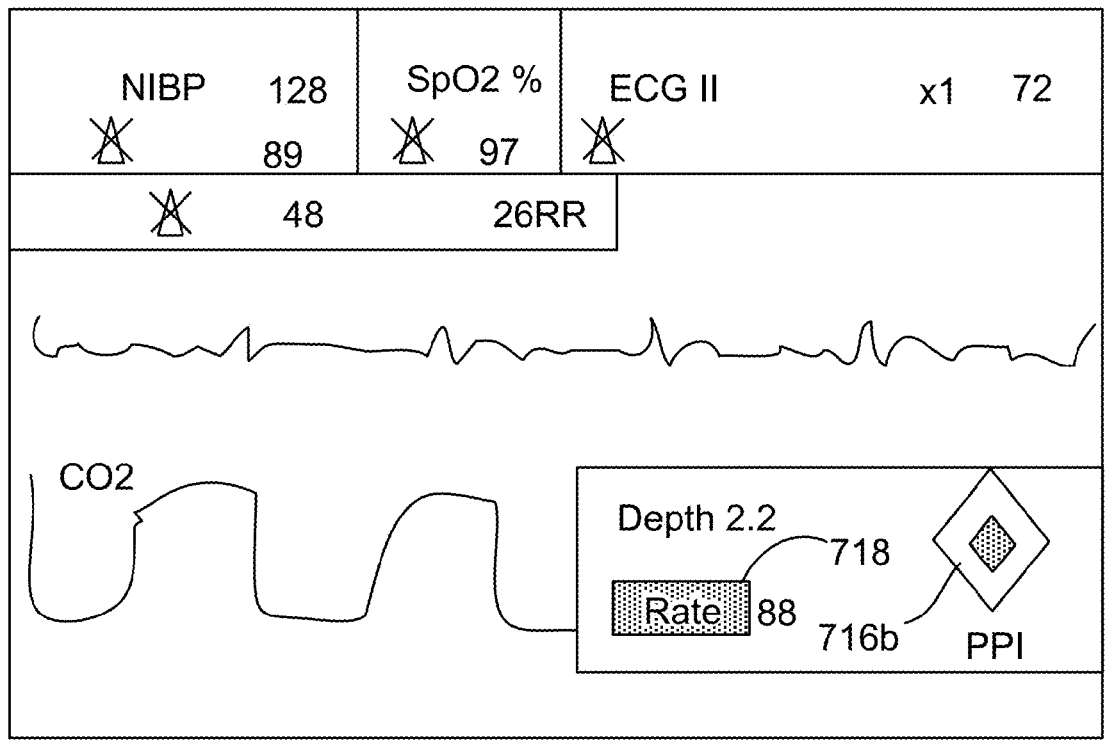

FIGS. 7A and 7B show defibrillator displays that indicate to a rescuer levels of perfusion being obtained by chest compressions that the rescuer is performing. FIG. 7A shows exemplary data displayed during the administration of CPR chest compressions when the CPR quality is within acceptable ranges, while FIG. 7B shows modifications to the display when the CPR quality is outside of the acceptable range.

In the example shown in FIG. 7B, the rate of chest compressions has dropped from 154 compressions per minute (FIG. 7A) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 718 to emphasize the rate information. In this example, the visual indication 718 is a highlighting of the rate information. Similar visual indications can be provided based on depth measurements when the depth of the compressions is shallower or deeper than an acceptable range of depths. Also, when the change in rate or depth indicates that a rescuer is becoming fatigued, the system can display a message to switch who is performing the chest compressions, and can also emit aural or haptic feedback to the same effect.

In the examples shown in FIGS. 7A and 7B, a perfusion performance indicator (PPI) 716 provides additional information about the quality of chest compressions during CPR. The PPI 716 includes a shape (e.g., a diamond) with the amount of fill in the shape differing based on the measured rate and depth of the compressions. In FIG. 7A, the depth and rate decrease within the acceptable ranges (e.g., at least 100 compressions/minute (CPM) and the depth of each compression is greater than 1.5 inches) so the PPI indicator 716a shows a fully filled shape. In contrast, in FIG. 7B, when the rate has fallen below the acceptable range, the amount of fill in the indicator 716b is lessened such that only a portion of the indicator is filled. The partially filled PPI 716b provides a visual indication of the quality of the CPR is below an acceptable range.

As noted above with respect to FIG. 5A, in addition to measuring information about the rate and depth of CPR chest compressions, in some examples the defibrillator provides information about whether the rescuer is fully releasing his/her hands at the end of a chest compression. For example, as a rescuer tires, the rescuer can begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial. In addition, such factors can be included in a determination of whether the rescuer's performance has deteriorated to a level that the rescuer should be instructed to permit someone else perform the chest compressions, and such information can be conveyed in the various manners discussed above.

Figure 8A:
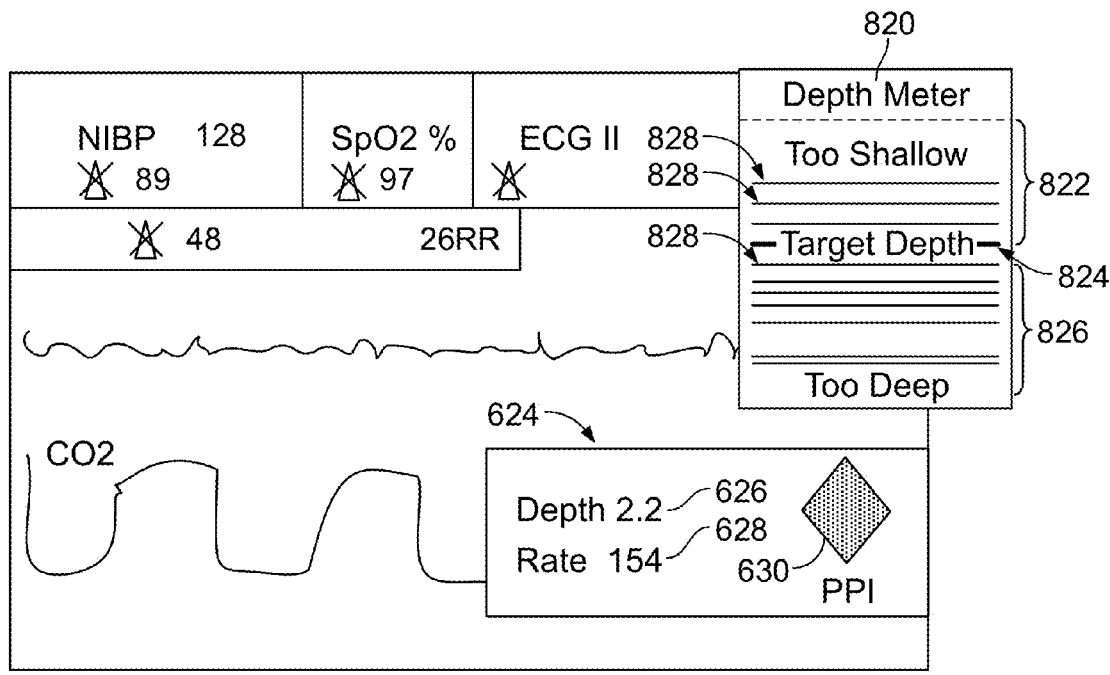
FIGS. 8A and 8B show screenshots with gradiated scales indicating target chest compression depths.

As shown in FIG. 8A, a visual representation of CPR quality can include an indicator of CPR compression depth such as a CPR depth meter 820. The CPR depth meter 820 can be automatically displayed upon detection of CPR chest compressions.

On the CPR depth meter 820, depth bars 828 visually indicate the depth of the administered CPR compressions relative to a target depth 824. As such, the relative location of the depth bars 828 in relation to the target depth 824 can serve as a guide to a rescuer for controlling the depth of CPR compressions. For example, depth bars 828 located in a region 822 above the target depth bar 824 indicate that the compressions were shallower than the target depth, and depth bars 828 located in a region 826 below the target depth bar 824 indicate that the compressions were deeper than the target depth. Again, then depth is inadequate (along with perhaps other factors) for a sufficient time to indicate that the rescuer is fatiguing, an indicator to switch rescuers can be provided in the manners discussed above.

Figure 8B:
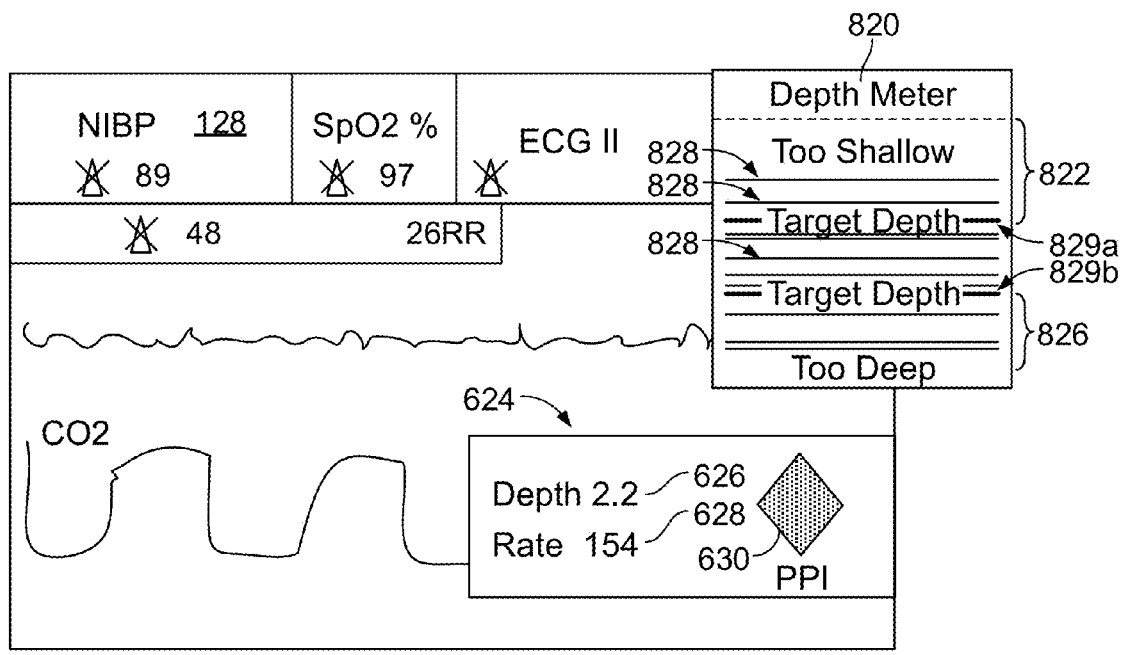

While the example shown in FIG. 8A displayed the target depth 824 as a single bar, in some additional examples, the target depth can be displayed as a range of preferred depths. For example, two bars 829a and 829b can be included on the depth meter 820 providing an acceptable range of compression depths (e.g., as shown in FIG. 8B). Additionally, in some examples, compressions that have depths outside of an acceptable range can be highlighted in a different color than compressions that have depths within the acceptable range of compression depths.

The depth bars 828 displayed on the CPR depth meter 820 can represent the compression depths of the most recent CPR compressions administered by the rescuer. For example, the CPR depth meter 820 can display depth bars 828 for the most recent 10-20 CPR compressions (e.g., the most recent 10 CPR compressions, the most recent 15 compressions, the most recent 20 CPR compressions). In another example, CPR depth meter 820 can display depth bars 828 for CPR compressions administered during a particular time interval (e.g., the previous 10 seconds, the previous 20 seconds).

In some additional embodiments, physiological information (e.g., physiological information such as end-tidal CO2 information, arterial pressure information, volumetric CO2, pulse oximetry (presence of amplitude of waveform possibly), and carotid blood flow (measured by Doppler) can be used to provide feedback on the effectiveness of the CPR delivered at a particular target depth. Based on the physiological information, the system can automatically determine a target CPR compression depth (e.g., calculate or look-up a new CPR compression target depth) and provide feedback to a rescuer to increase or decrease the depth of the CPR compressions. Thus, the system can provide both feedback related to how consistently a rescuer is administering CPR compressions at a target depth, and feedback related to whether the target depth should be adjusted based on measured physiological parameters. If the rescuers does not respond to such feedback and continues performed sub-optimal CPR, the system can then display an additional message to switch out the person performing CPR chest compressions.

In some examples, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, can determine whether to make further adjustments to the target compression depth.

And again, the actual performance of the rescuer against the revised target can be continually monitored to determine when the rescuer's performance has fallen below an acceptable level, so that the rescuer and perhaps others can be notified to change who is performing the chest compressions. Also, each of the relevant parameters of patient condition discussed above with respect to the various screenshots can be made one of multiple inputs to a process for determining when rescuers who are performing one component of a rescue technique should be switched out with another rescuer, such as for reasons of apparent fatigue on the part of the first rescuer.

The particular devices and displays shown in FIGS. 5A-8B can be implemented, as noted above, with a system that uses particular techniques to improve the accuracy of a prediction that an applied shock can be a success and that uses AMSA or other SPA values in making such a prediction. For instance, the feedback provided by the displays in the figures can be determined by selecting an appropriate ECG window size for calculating AMSA (e.g., one second or slightly longer, such as 1.5 seconds or 2 seconds), a window type (e.g., Tukey), and particular coefficients for the window. Such factors can also be changed over the time of a VF event, as discussed above, so as to maintain a most accurate predictor of defibrillation success.

While at least some of the embodiments described above describe techniques and displays used during manual human-delivered chest compressions, similar techniques and displays can be used with automated chest compression devices such as the AUTOPULSE device manufactured by ZOLL Medical Corporation of Chelmsford, Mass.

Figure 9:
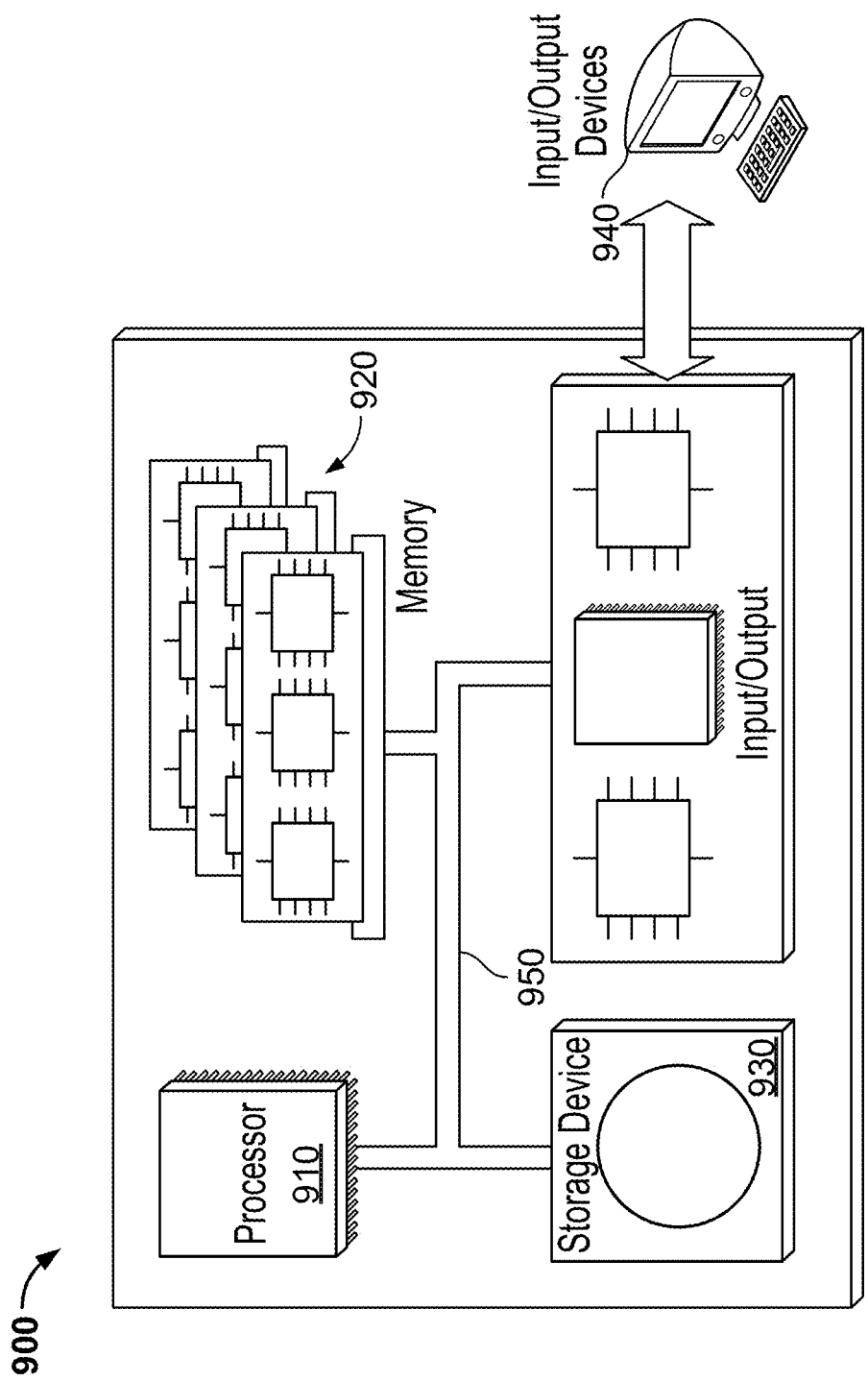
FIG. 9 shows a general computer system that can provide interactivity with a user of a medical device, such as feedback to a user in the performance of CPR.

The particular techniques described here can be assisted by the use of a computer-implemented medical device, such as a defibrillator that includes computing capability. Such defibrillator or other device is shown in FIG. 9, and can communicate with and/or incorporate a computer system 900 in performing the operations discussed above, including operations for computing the quality of one or more components of CPR provided to a victim and generating feedback to rescuers, including feedback to change rescuers who are performing particular components of the CPR. The system 900 can be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives can store operating systems and other applications. The USB flash drives can include input/output components, such as a wireless transmitter or USB connector that can be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor can be designed using any of a number of architectures. For example, the processor 910 can be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 900. In one implementation, the storage device 930 is a computer-readable medium. In various different implementations, the storage device 930 can be a floppy disk device, a hard disk device, an optical disk device, or a tape device.

The input/output device 940 provides input/output operations for the system 900. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a particular activity or to generate a particular result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor can receive instructions and data from a read-only memory or a random access memory or both. The essential elements of a computer are a processor for executing instructions and one or more memories for storing instructions and data. Generally, a computer can also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described can be employed, and can be encompassed by the following claims.

What is claimed is:

1. A system comprising:
   one or more electronic ports for receiving signals from sensors for obtaining a time domain electrocardiogram (ECG) of a patient;
   a patient treatment module comprising an ECG analyzer and a non-transitory computer-readable storage medium encoded with a computer program comprising instructions that, when executed, cause one or more processors to perform operations comprising:
      performing at least one transformation of at least a portion of a time domain ECG signal from the patient into frequency domain data,
      determining a first frequency-based value over a first evaluation period based on the at least one transformation,
      determining a second frequency-based value representing an upward trend over a second evaluation period based on the at least one transformation, and
      determining a probability of therapeutic success based at least in part on the first frequency-based value and the second frequency-based value; and
   an output device for presenting an indication of the probability of therapeutic success.

2. The system of claim 1, wherein the first frequency-based value comprises an amplitude spectral area (AMSA) value and the second frequency-based value comprises an AMSA trend.

3. The system of claim 2, the operations comprising:
   applying a first threshold to the first frequency-based value;
   determining that the first frequency-based value is below the first threshold; and
   in response, determining the probability of therapeutic success at least in part based on the second frequency-based value.

4. The system of claim 3, wherein the first predetermined threshold is 12 mVHz.

5. The system of claim 3, wherein determining the probability of therapeutic success comprises:
   comparing the probability of therapeutic success to a second threshold;
   determining that the probability of therapeutic success exceeds the second threshold; and
   in response, indicating the probability of therapeutic success.

6. The system of claim 2, wherein the change of the AMSA value is determined as a difference between two AMSA values corresponding to two time points within the first evaluation period.

7. The system of claim 6, wherein each unit of the difference corresponds to a predetermined increase of defibrillation shock success.

8. The system of claim 6, wherein an end of the first evaluation period and a beginning of the second evaluation period are defined by a preset time interval.

9. The system of claim 8, wherein the preset time interval comprises approximately 2 minutes.

10. The system of claim 6, wherein at least one of the two AMSA values comprises at least one of a mean AMSA value, a median AMSA value, a center AMSA value, and a peak AMSA value determined around a first time point and during the first evaluation period.

11. The system of claim 6, wherein determining the change of the AMSA value comprises determining a third AMSA value corresponding to a second time period that is subsequent to the first evaluation period.

12. The system of claim 11, the operations comprising determining whether the metabolic state of the myocardium of the patient is continuously improving.

13. The system of claim 2, wherein the AMSA trend comprises a rate of change of the AMSA value over time.

14. The system of claim 1, wherein the treatment comprises delivering a defibrillating shock.

15. The system of claim 1, wherein the treatment comprises at least one of introduction of a thrombolytic agent, introduction of a metabolite, introduction of a metabolic enhancing agent, and application of electromagnetic energy to stimulate cardiac tissue at energy levels below those sufficient for defibrillation.

16. The system of claim 1, wherein indicating the administration of the treatment to the patient comprises displaying a treatment recommendation on a display of the patient treatment module.

17. The system of claim 1, wherein determining a probability of therapeutic success is based on a regression analysis.

18. The system of claim 17, wherein the regression analysis comprises a statistical model that inputs the first frequency-based value and the second frequency-based value and outputs the probability of therapeutic success.

19. The system of claim 18, wherein the statistical model inputs a first AMSA value and a second trend in AMSA values and outputs a probability of therapeutic success.

20. The system of claim 1, wherein providing an indication of the probability of therapeutic success comprises sending a signal to display the indication of the probability of therapeutic success to a user.

21. The system of claim 1, wherein the indication of the probability of therapeutic success comprises one or both of audible and visual information.

* * * * *